United States Patent
Urakabe

(10) Patent No.: US 9,463,081 B2
(45) Date of Patent: Oct. 11, 2016

(54) INTRAORAL VIDEO CAMERA AND DISPLAY SYSTEM

(75) Inventor: Nobuchika Urakabe, Tokyo (JP)

(73) Assignee: Kabushiki Kaisya Advance, Tokyo (JP)

( * ) Notice: Subject to any disclaimer, the term of this patent is extended or adjusted under 35 U.S.C. 154(b) by 284 days.

(21) Appl. No.: 13/978,939

(22) PCT Filed: Jan. 11, 2012

(86) PCT No.: PCT/JP2012/050394
§ 371 (c)(1),
(2), (4) Date: Jul. 10, 2013

(87) PCT Pub. No.: WO2012/096312
PCT Pub. Date: Jul. 19, 2012

(65) Prior Publication Data
US 2013/0286174 A1    Oct. 31, 2013

(30) Foreign Application Priority Data

Jan. 11, 2011 (JP) ................. 2011-015764
Jan. 12, 2011 (JP) ................. 2011-017192
Jan. 13, 2011 (JP) ................. 2011-020197
Jun. 16, 2011 (JP) ................. 2011-134633

(51) Int. Cl.
A61B 1/04     (2006.01)
A61C 19/04    (2006.01)
A61B 1/00     (2006.01)
(Continued)

(52) U.S. Cl.
CPC ............ *A61C 19/04* (2013.01); *A61B 1/0005* (2013.01); *A61B 1/00009* (2013.01); *A61B 1/04* (2013.01); *A61B 1/24* (2013.01); *A61B 1/247* (2013.01); *A61C 9/0053* (2013.01); *A61B 1/00087* (2013.01); *A61B 1/00101* (2013.01); *A61B 1/0607* (2013.01)

(58) Field of Classification Search
None
See application file for complete search history.

(56) References Cited

U.S. PATENT DOCUMENTS

2004/0136580 A1    7/2004  Matsumiya et al.
2006/0001740 A1*   1/2006  Fujie et al. .................. 348/66
(Continued)

FOREIGN PATENT DOCUMENTS

EP    1120081 A2     8/2001
JP    2001-333898 A  12/2001
(Continued)

OTHER PUBLICATIONS

Kikumoto, Rikiya, "The mobile type teleradiology system contributes to a medical scene," Gekkan Shin Iryo, The August issue, Jul. 23, 2010, pp. 58-61.

*Primary Examiner* — Kevin McInnish
(74) *Attorney, Agent, or Firm* — Foley & Lardner LLP

(57) ABSTRACT

A system for capturing and displaying an image of an entire oral cavity includes a handheld intraoral camera and a computer processor. Each of left and right panoramic tooth row images is generated by combining a first digital still image including the center of the front teeth with a second digital still image taken adjacent to the first digital still image and having an overlapping portion with the first digital still image, to form a first combined image. This step is repeated until a last digital still image positioned at the back tooth of the respective row is combined with a last combined image, forming the left or right panoramic tooth row image. The left and right panoramic tooth row images are superposed in an area of the center of the front teeth to form the full panoramic tooth row image.

8 Claims, 29 Drawing Sheets

(51) Int. Cl.
*A61B 1/247* (2006.01)
*A61B 1/24* (2006.01)
*A61C 9/00* (2006.01)
*A61B 1/06* (2006.01)

(56) References Cited

U.S. PATENT DOCUMENTS

2008/0038688 A1 2/2008 Kopelman et al.
2011/0017619 A1* 1/2011 Motoyama ............... A61B 6/14
    206/305
2011/0212420 A1* 9/2011 Vuillemot .................... 433/215
2011/0270583 A1* 11/2011 Getto et al. ...................... 703/1

FOREIGN PATENT DOCUMENTS

| | | |
|---|---|---|
| JP | 2003-299677 A | 10/2003 |
| JP | 2004-202069 A | 7/2004 |
| JP | 2008-125719 A | 6/2008 |
| JP | 2008-132336 A | 6/2008 |
| JP | 2010-214055 A | 9/2010 |
| WO | WO 0008415 A1 * | 2/2000 ............... A61B 1/24 |

* cited by examiner

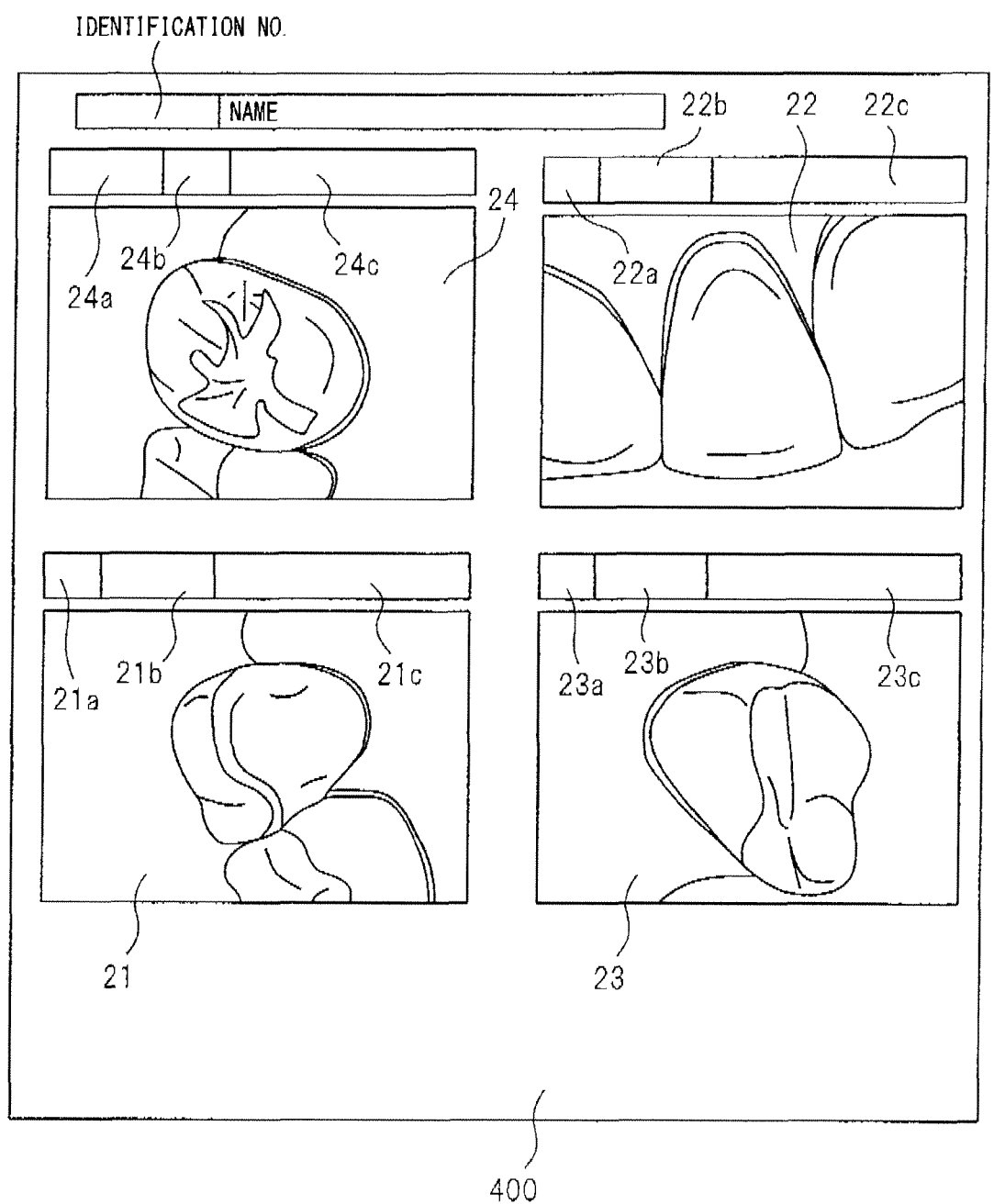

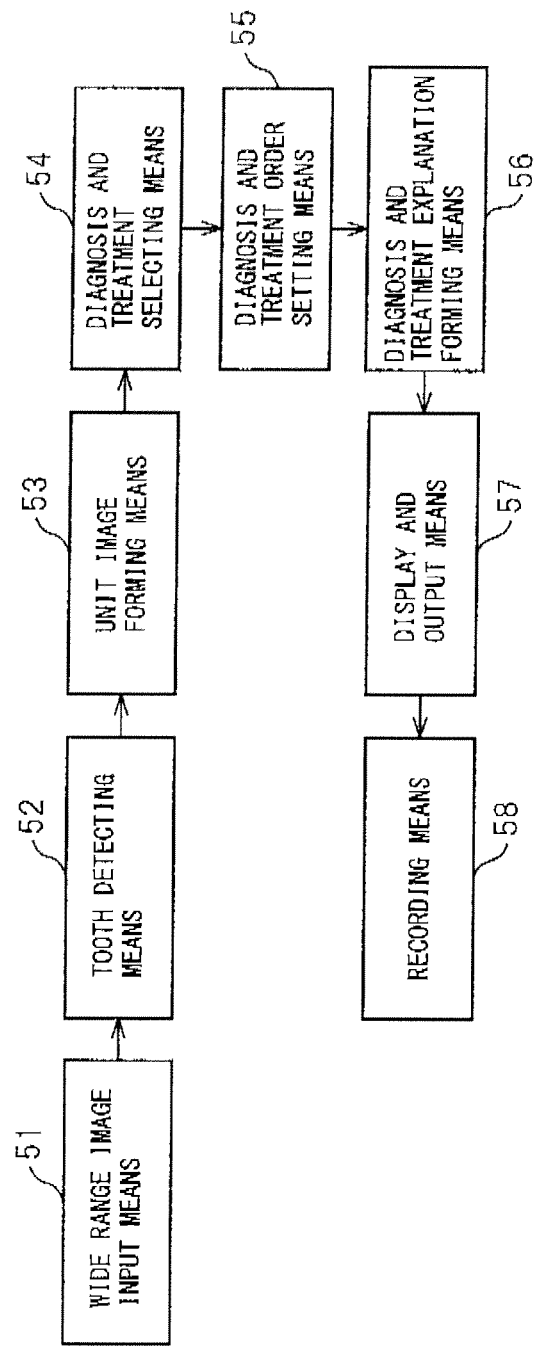

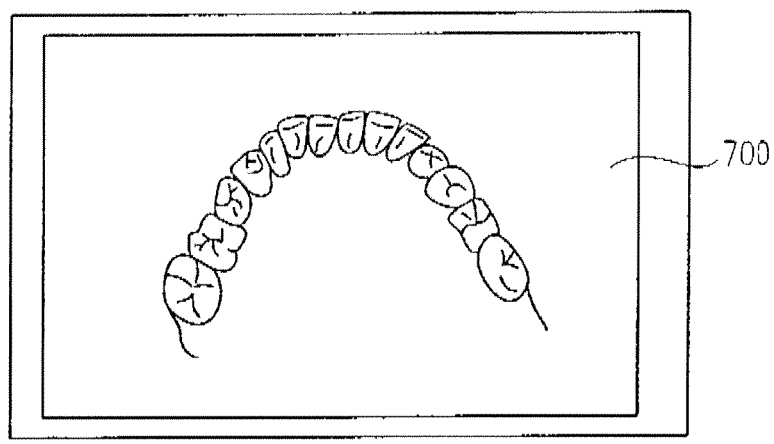
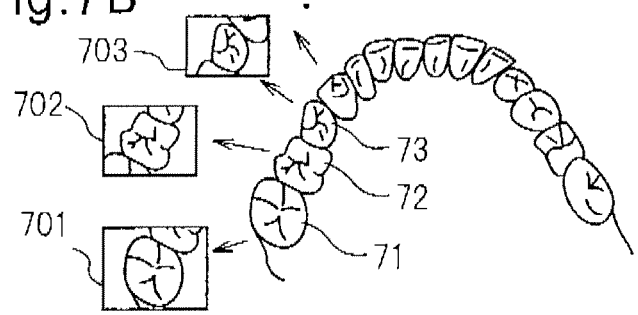
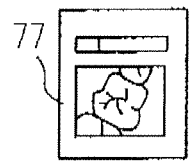
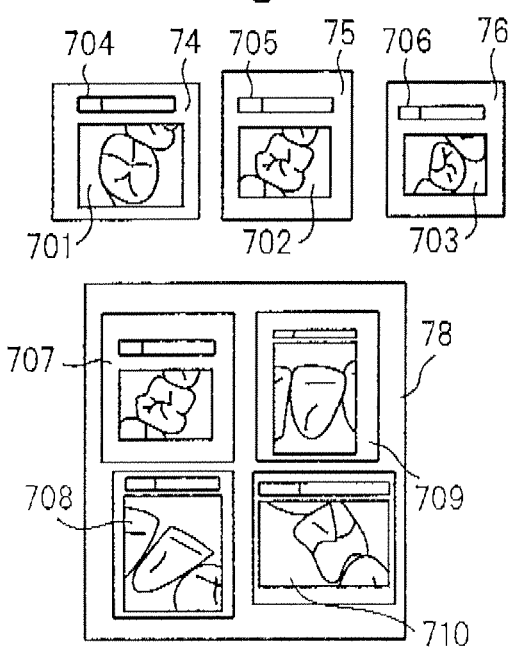
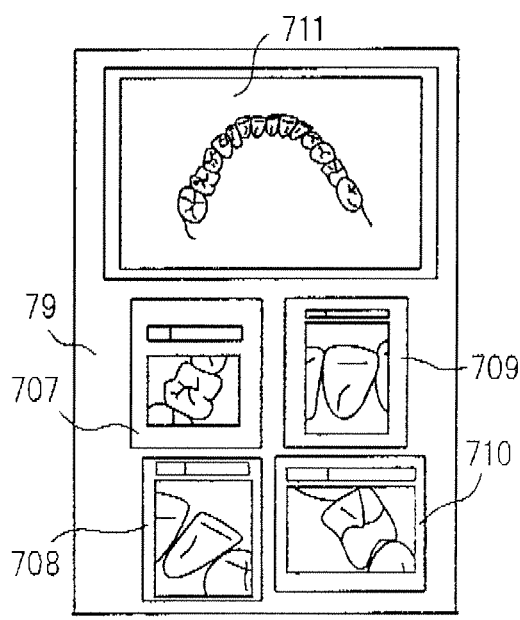

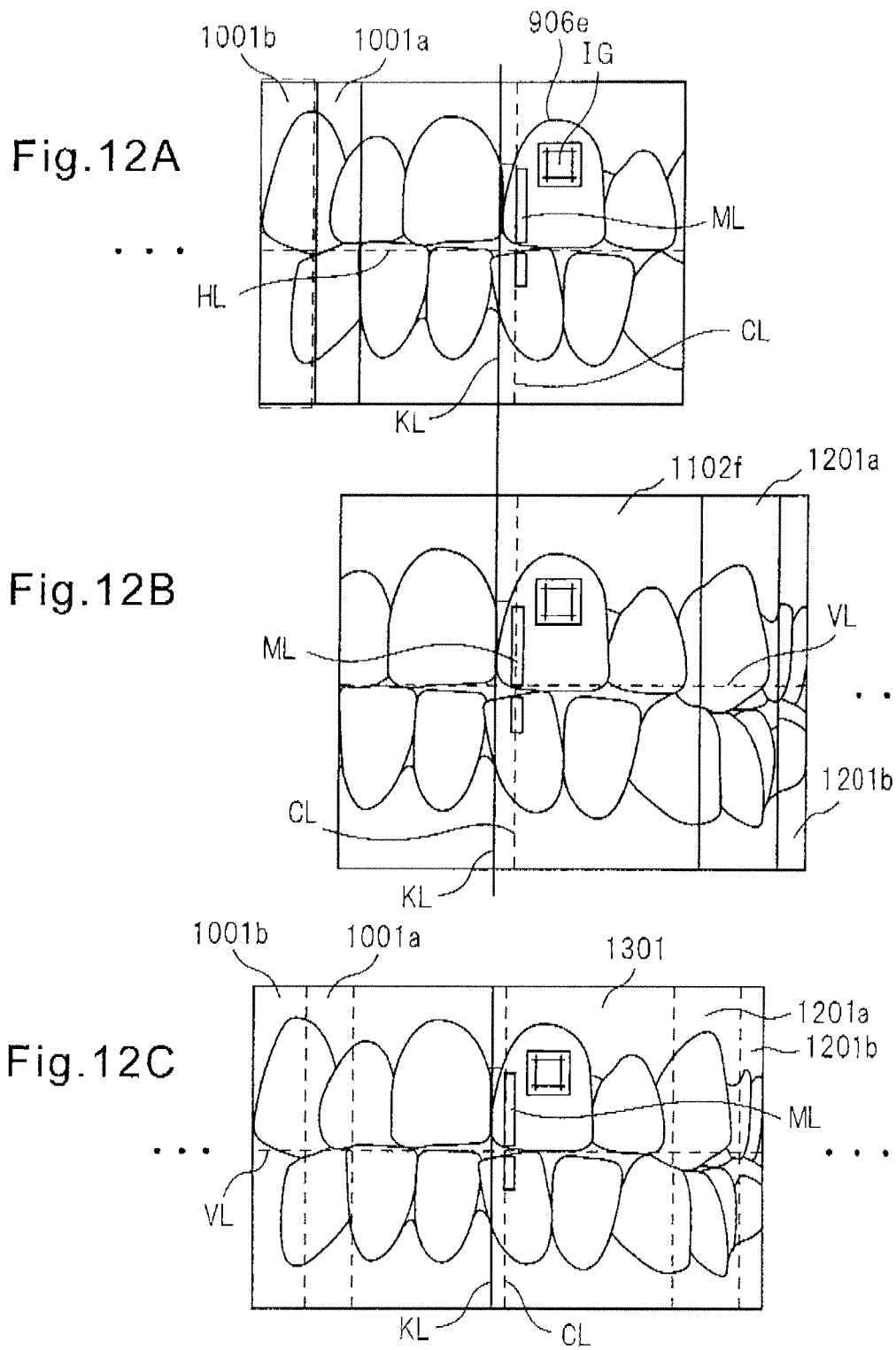

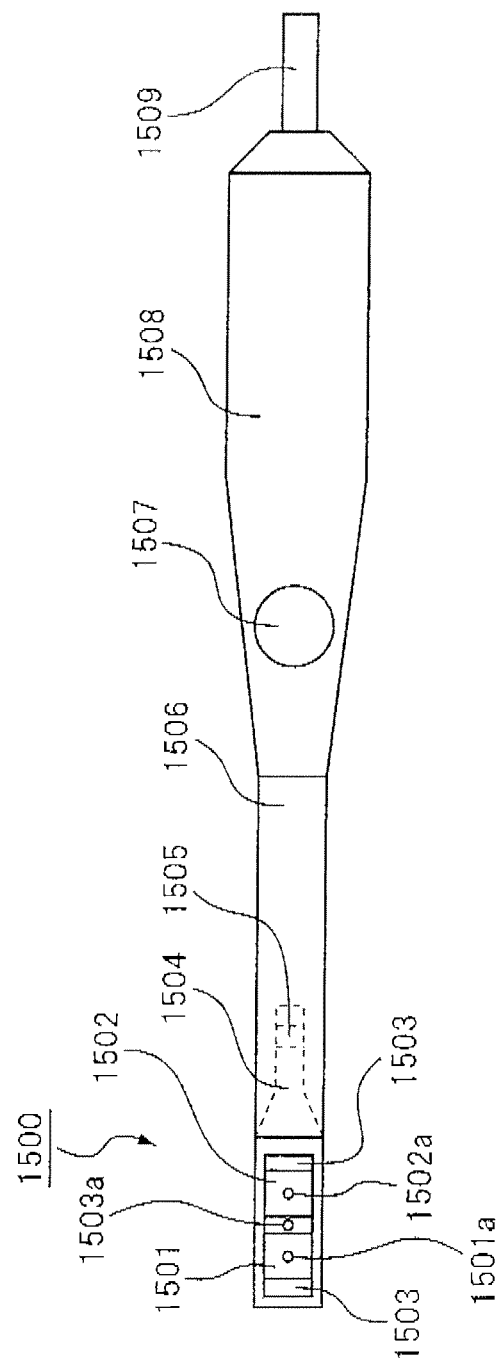

INTRAORAL VIDEO CAMERA AND DISPLAY SYSTEM

TECHNICAL FIELD

The present invention relates to a system which captures an image of the entire oral cavity and displays a panoramic image.

BACKGROUND ART

In the treatment of tooth cavities and other intraoral diseases, when the target treatment ends, the visits to the clinic usually also end. Treatment of tooth decay usually starts when the patient becomes aware of tooth pain, discomfort, or other symptoms. When the treatment ends, the visits to the clinic also end. This is the usual pattern. Therefore, even if there is other tooth decay, if there are no noticeable symptoms, in many cases it is left alone—the clinic is visited only after the tooth decay advances. Further, with such one-time visits to the clinic, a healthy oral cavity is not secured. Staining, swelling, loss, tartar, wear, salivary calculus, mismatch, and other issues for which there are no subjective symptoms, but which can be seen from the outside after often unnoticed by the person in question.

For the business operations of a dental practice as well, one-time treatment sometimes cannot by any means be said to be good in terms of profitability, but there were no means found which were suitable for dealing with this. For example, PLT 1 discloses a configuration of an electronic patient chart in which the entire rows of teeth are displayed on a computer monitor and which the individual teeth are colored so as to enable easy viewing from the patient side. Ease of viewing the rows of teeth is a requirement which is sought in informed consent, but even if parts of the entire rows of teeth are easy to view, for use for explanations of treatment, greater enlargement and configuration for enabling understanding of the purpose of treatment are required.

Further, PLT 2 describes a configuration in which a plurality of sets of intraoral image data which is captured in advance are displayed on a monitor screen of a computer. Furthermore, PLT 3 discloses a method of presentation by display of moving images and still images using a computer to as to improve the understanding of specialized terminology etc. as a tool for obtaining informed consent. Further, it is described that such a presentation method may be used for educational purposes in elementary schools, junior high schools, various businesses, retirement homes, etc. Furthermore, PLT 4 discloses fluorescent film which enables visualization of an X-ray image and a configuration which reflects an image rendered visible by a prism for capture by a camera.

As other patent literature relating to dental medicine, for example, the following such literature may be mentioned: PLT 5: Oral Cavity Washer Fitted With Videoscope; PLT 6: Intraoral Camera Apparatus and Method; PLT 7: Handpiece for Dental Examination and Diagnosis; PLT 8: Hand Switch for Intraoral Camera, PLT 9: Intraoral Camera With Built-in Display; PLT 10: Intraoral Camera Apparatus and Dental Mirror; PLT 11: Dental Camera Apparatus; PLT 12: Instrument for Periodontal Examination Use; PLT 13: Regular Examination Method and System; PLT 14: Apparatus Used in Dental Medicine Environment; and, further, PLT 15: X-Ray Image Detection System for Medical Use.

CITATIONS LIST

Patent Literature

PLT 1: Japanese Patent Publication No. 10-97404A
PLT 2: Japanese Patent Publication No. 2005-334426A
PLT 3: Japanese Patent Publication No. 10-97405A
PLT 4: Japanese Patent Publication No. 10-201757A
PLT 5: Japanese Patent Publication No. 2001-212161A
PLT 6: Japanese Patent Publication No. 2005-144171A
PLT 7: Japanese Patent Publication No. 62-246347A
PLT 8: Japanese Patent Publication No. 2001-29315A
PLT 9: Japanese Patent Publication No. 2002-355262A
PLT 10: Japanese Patent Publication No. 2005-304600A
PLT 11: Japanese Utility Model Publication No. 5-304025
PLT 12: Japanese Utility Model Registration No. 3131408U
PLT 13: U.S. Pat. No. 5,752,527
PLT 14: Japanese Patent Publication No. 2009-516555A
PLT 15: Japanese Patent Publication No. 5-130991A

SUMMARY OF INVENTION

Technical Problem

Numerous proposals have been made for examination of the oral cavity by using image displays. In the final analysis, these just provide information to patients by conventional one-time local treatment systems. They do not reach the level of systems designed for ensuring health of the teeth in the oral cavity as a whole.

Further, when a dentist explains treatment to a patient, sometimes he or she will use an intraoral image or X-ray image obtained by a dental camera, but the image itself is hard to interpret.

Furthermore, images and data easily understandable by the patient can be expected to help the dentist explain diagnosis and treatment to the patient, increase interest of the patient in intraoral health, and provide incentive for self health management, but such equipment, image displays, etc. fulfilling this promise have still not been proposed.

The dental practice has had to pay more attention to business operations along with the increase in the number of clinics. In order to stabilize business operations, entry into new dental diagnosis and treatment areas, reduction of costs, securing patients who regularly visit the clinics, and streamlining of the dental field have become necessary. For example, a handheld terminal such as described in the previously cited Japanese Utility Model Registration No. 3131408U has also been proposed.

Solution to Problem

In consideration of the above, the present invention proposes to provide a continuously captured image sequence forming means for continuously capturing side surfaces of rows of teeth to form an image sequence, a side surface tooth row image forming means for combining sequences of images which were formed by the continuously captured image sequence forming means as partial tooth row images from images forming the centers of overall composites so as to form a plurality of partial tooth row images, and a side surface tooth row image combining means for linking and combining a plurality of partial tooth row images which were formed by the side surface tooth row image forming means based on an image forming the center of the overall composite so as to form overall rows of teeth. By configuration in this way, according to the present invention, it is possible to use a handheld type of intraoral camera to form a clear panoramic image of the rows of teeth. Furthermore, it is possible to display an X-ray panoramic image of the rows of teeth and a panoramic image of the rows of teeth which have been virtual straightened or virtually beautified and colored side by side or display them superposed so as to broaden the range of diagnosis and treatment in the dental practice.

Furthermore, the present invention proposes a combination comprised of a unit image forming means for forming an image of the oral cavity for each diagnosis and treatment and care unit, a setting means for setting diagnosis and treatment and care order information for images captured by unit image formation by the unit image forming means, a display means for displaying images, with the diagnosis and treatment and care order information attached, based on the diagnosis and treatment and care order information so as to be able to be displayed in a list form, and a display medium which displays and records display information which is obtained by the display means. By configuration in this way, according to the present invention, it becomes possible to raise self awareness of the patient about treatment so as to promote intraoral health and encourage regular visits by patients and thereby realize an improvement of the efficiency of business operations of the dental field.

Furthermore, in addition, the present invention proposes preparing data for using a monitor of a computer etc. to explain details of treatment using the above-mentioned method etc. to the patient, manage attendance of dental employees, manage fees for diagnosis and treatment, and otherwise have a dental employee process data using a computer by a compact mobile terminal which is provided with a processor, memory, communicating means, inputting means, and display means. By using such a compact mobile terminal, in the present invention, greater efficiency in the dental practice is realized.

The image which is referred to in the present invention in the final analysis indicates a digital image. Either a moving image or a still image may be used. Further, the "image forming the center of the overall composite" in the present invention refers to for example an image common to two partial panoramic images when combining the two. "Overall" does not refer to only the final overall panoramic image of rows of teeth. For example, it also includes the case of a panoramic image of rows of teeth in the process of combination which is obtained by first combining two partial panoramic images of rows of teeth when forming three or more partial images of rows of teeth. "Combining . . . from an image forming the center of the overall composites" means, for example, combining a plurality of still images which were obtained by continuously capturing rows of teeth in the back tooth direction from images where part of teeth at the center of the surface of the front teeth becomes the center so as to form a left side partial tooth row panoramic image and a right side partial tooth row panoramic image. "Linking and combining" means, for example, combining a left side partial tooth row panoramic image and a right side partial tooth row panoramic image at portions common to both or combining them by connection based on linkable portions.

The present invention sometimes sets a mark at an image including a part forming the center of combination. This "mark" indicates, for example, one which will not easily dissolve in saliva, water, etc. and which has an elongated rectangular shape or a seal which has a short rectangular shape and, for example, is coated on its back surface with a binder, adhesive, etc. and can be peeled off or another such deposit. Further, the invention is not limited to a deposit. It is also possible to draw a mark on the teeth by a pen which can give a removable color which can be clearly captured such as green, red, etc.

The portion where the mark is made is preferably arranged so as to span an upper tooth and lower tooth, but, for example, when capturing the image of only one of the upper jaw or lower jaw, it may be arranged at only the one to be captured. Further, the "predetermined position on the rows of teeth for making a mark" indicates, for example, an image becoming the center of combination at a position where a change in the capturing direction of the camera, the way it is held, etc. would cause the image capture to stop and the movement to stop.

The mark may be formed by a color (green, blue, etc.) and shape which can be easily discerned in the captured image. The material and color are suitably selected. Further, when obtaining a 3D image, it is possible to use a mark with provides a characteristic 3D property. The mark need only be one which is shown on the surface of the teeth and which clearly displays a position in the captured image, so for example it is also possible to provide a means which fires a laser sighting beam giving a shape of known dimensions on the tooth surface or to arrange a means such as a spotlight where there is correspondence between the lighting distance and area of the emitted light so as to enable light to be shone from the intraoral camera toward the teeth.

The mark need only be one enabling start of combination from the image where the mark is captured at a predetermined position. The capturing direction need not always be from the back teeth. The capturing direction and the combining direction need not be opposite. At the time of combination, sometimes the parts are combined from an image where a mark is displayed at a predetermined position to the left and right and finally the images are combined as a whole based on an image at which the mark is displayed at a predetermined position. The "predetermined position of the mark for starting combination" includes the illustrated case where, for example, the mark is at the center of the captured image, but the invention is not limited to this. It may be at any portion where combination is easy in partial combination and overall combination.

Sometimes, for example, in the case of partial combination of the three right, center, and left side surfaces of the rows of teeth such as the back side surfaces of the teeth, marks are required at the tooth between the right side surface and the center side surface and two teeth at the center side surface and right side surface, that is, sometimes a plurality of marks may be provided. The "side surface of the rows of teeth" referred to in the present invention is not limited to the front side. The back side and bite surfaces are sometimes also included. "Continuous capture" indicates automatic image capture at a rate of up to 30 images per second or less.

"Combine" is the method, of combination of the panoramic images. For the method at the time of combination, existing methods may be selectively used. Simple combination, simple alignment, block matching, the Lucas-Kanade method and other optical flow estimation methods and other automatic or manual methods of combination can be utilized, but it is preferable to use an affine transform or other image adjusting means in advance and use the common parts between images as the basis to adjust the slant, magnification, etc.

The characterizing portion in the present invention is a line shape, dot shape, graphic shape, or 3D shape when combining panoramic images of partial rows of teeth, for example, when combining two side panoramic images, the center front teeth and the boundary lines of the front teeth, but the invention is not limited to this. One of the characterizing teeth of the front teeth or front end of the gums or other portions are also included.

The "oral cavity" in the unit image forming means for forming an image of the oral cavity for each unit of diagnosis and treatment and care indicates the teeth, rows of teeth, gums, alveolar bone, lips, hard palate, soft palate, uvula, and other regions.

"Diagnosis and treatment" includes diagnosis and treatment together and diagnosis by a dentist and treatment by a specialized medical institution.

The "diagnosis and treatment and care unit" indicates the range of one diagnosis and treatment procedure of tooth decay, periodontal disease, tongue cancer, gum cancer, etc. and sometimes also indicates stain removal, straightening, or other care, preventive treatment, and quasi-diagnosis and treatment.

"Care" indicates something of the extent which can be handled by brushing or application of fluorine or a mouthwash etc. and preventive care such as coating the teeth with fluorine, cleaning, coating with a preventive agent against periodontal disease, and other actions.

"Image forming" indicates conversion to image data which can be output to and displayed on a computer monitor (display) device or mobile phone display and also a state printed on paper or other state displayed two-dimensionally or three-dimensionally.

The diagnosis and treatment and care order information of the setting means for setting diagnosis and treatment and care order information for an image processed by unit image-forming by the unit image forming means includes symbols, codes, numerals, etc. indicating the order of diagnosis and treatment, prevention, and care and, in addition, includes the date and time of diagnosis and treatment, the state of advance of disease, predictions on the advance of disease, and other data. It need only be enough to enable determination of the order of diagnosis and treatment and care for at least a plurality of unit images. It may be content which can be directly visually confirmed and may be parameters for computation which can be confirmed after computer processing.

"Displayed in a list form" means at least a list of the order of diagnosis and treatment and care which, if in a state able to be easily viewed as a whole, is printed on several sheets of paper or is displayed as several images able to be changed by scrolling.

The "display medium" which displays and records the display information which is obtained at the display means indicates a state displayed by being printed on one or more sheets of paper or booklets or a state of image data of the JPEG, GIF, BMP, or other format displayed in a portable manner. The "display medium" includes a sheet or booklet of paper, a USE memory, SD card, memory, or other recording device provided in a display device, mobile phone, etc., but indicates at least printed matter or an electronic image etc. which a patient can carry and use to view his or her oral cavity. Alternatively, it includes the case of viewing one's own intraoral data on a homepage on the Internet. Therefore, the display medium includes a desktop type or notebook type of personal computer.

The present invention utilizes a reflecting mirror, so the path of the sighting beam is relatively long. By using an LED or other sighting beam source with a spread based on the directional angle, it is possible to clarify the image capture position and the image capture range.

Further, the present invention provides an intraoral camera which utilizes a reflecting mirror wherein the dentist etc. can clearly understand the image capturing position even with an image which is captured through this reflecting mirror.

Furthermore, the present invention measures the posture of an intraoral camera which moves vertically and horizontally by a gyro sensor so as to obtain angle information of the body, derives the angle of the mirror from the angle of this body, and obtains a grasp of what kind of state the camera is in. By adjusting the posture of the image from the captured state, regardless of the state of the vertically and horizontally moving camera, it is possible to realize display of an image in a readily viewable state at all times.

In the present invention, an angular acceleration sensor (gyro sensor), acceleration sensor, or other position sensor is used. Specifically, rate gyros which output angular acceleration, rate integrating gyros which output angle, posture gyros, MEMS (micro electro mechanical systems) type and other mechanical type, optical type, and other angular acceleration sensors, piezoresistance type, electrostatic capacity type, and heat sensing type MEMS sensors, and other acceleration sensors can be mentioned.

The color of the sighting beam in the present invention may be any color which can be discriminated from the color of illumination light. If the illumination light is white, the sighting beam may be red, green, etc. Alternatively, as the timing of firing the sighting beam, a timing right before the user starts an image capture operation is preferable, but the beam may also be fired in a short time during the image capture as well in some cases.

Furthermore, the present invention provides a mobile terminal which can be worn on the body. By arranging inside it a storing means, computer, modulating and demodulating means for communication with the outside, and display means and enabling input and output for the dental practice as a whole, it is possible to manage dental employees, access electronic patient charts, calculate diagnosis and treatment fees, etc. at one's fingertips and to share, display, and synchronize this information so that even a handful of people can administer the dental office work and perform administrative processing for diagnosis and treatment in a dispersed manner. This enables the work of the dental practice to be streamlined.

The present invention preferably arranges an operating interface at a position which can be operated at the time of treatment, but depending on the operator, the method of operation will differ or the fingers will not reach the interface. Due to such physical factors, an adjusting means is provided for giving a time lag by the method of operation of the interface between operation of the operating interface and the actual operation performed in accordance with the state of inability of operation or the state of explanation to the patient (for example, when an interval is necessary between the oral explanation and screen display).

For example, when the operating interface is a switch, if the switch is successively pressed twice, the operation is performed after 2 seconds. In this way, it is possible to adjust the delay time by the number of times pressed or adjust the timing of display by the display means by the number of times pressed, the pressed time, etc. for a GUI-like operation.

Furthermore, the present invention provides a means for fetching an X-ray image and superposing it over an actual image or, for example, splicing together X-ray images for the different teeth to form a panoramic image and superposing it over an actual image obtained by capturing and combining images in the same way so as to enable a panoramic comparison from the side surfaces of the rows of teeth. By superposing, aligning, etc. this actual image and X-ray images on a display means, much greater understanding of treatment by the patient is realized.

Furthermore, the present invention forms a terminal which connects with a computer terminal wirelessly or by cable, is sometimes provided with a liquid crystal display, tenkeys, etc., and can be worn at the user arm, leg, or other part so as to enable input and output of patient information etc. with the computer terminal at one's fingertips, enable the dentist to obtain past data necessary for treatment and background information for when explaining treatment to individual patients in a manner not visible to the patients, and enable accurate diagnosis and treatment and explanation of treatment to the patients.

That is, a dental diagnosis and treatment system may be formed comprised of a mobile terminal which is provided with an input part for inputting dental related information and a display part for displaying dental related information, a host terminal which is provided with a recording means for temporarily or continuously recording dental related information and a processing means for processing dental related information based on a predetermined algorithm, and an information transmitting means for transmitting information between the mobile terminal and a center terminal wirelessly or by cable. In this case, the mobile terminal may be carried by being worn by the dental employee on his arm, leg, upper torso, lower torso, or other part of the body. All or part of the dental employees can therefore share the information which is displayed.

The present system may be configured to be portable as explained above and may be used as a tablet type or a desktop type PC. In this case as well, centralized management of dental information is possible.

A mobile terminal is a terminal which enables input and output and enables information processing, so enables centralized management of intraoral information, dental diagnosis and treatment information, dental office information, dental employee information, and other dental practice related information. Specifically, it displays information from corresponding software, an intraoral camera or other peripheral device, etc., adds new data, corrects data, deletes it, and otherwise processes input and stores data, shares data with other mobile terminals and host terminals and displays and processes input in synchronization with the same, but the invention is not limited to this. It is sufficient that the required dental information can be displayed, recorded, input, and processed from the mobile terminal.

On the computer monitor screen, for example, on the screen of the mobile terminal, a menu is displayed. In addition, various information is displayed by switching of the screen each time the user selects it by a mouse etc. Alternatively, a single screen displays all information of a specific patient as an individual window screen.

The user follows the displayed content of the screen to select, newly add, correct, delete, and otherwise input information. Input is performed by using the attached tenkeys or virtual tenkeys or by selecting preset input text by a mouse, tenkeys, etc.

Further, attendance of the dental employees can, for example, be input by the individual employees using their own mobile terminals and the host terminal or an attendance-keeping staff can newly add, correct, delete, or otherwise process input from his or her own mobile terminal or the host terminal. If the dental employees have their own mobile terminals and only the staff concerned should perform processing through them, it is also possible to set passwords for the staff concerned.

"Centralized management" means, for example, the case where a single terminal is used for input, output, and display of intraoral information, dental diagnosis and treatment information, dental office information, dental employee information, and other information related to the dental practice, but the invention is not limited to this. Even only part of that information is included if sufficient for the intended management.

The present invention further forms a dental treatment menu by combining partial subdivided images obtained by subdivision in advance and enables formation of still images, slide like moving images, moving images, or other explanatory images in accordance with the treatment for the individual patients.

The subdivided images are, for example, preferably images of tooth extraction, images of bridging actions of facing teeth, images explaining dental work, etc. prepared in advance as CG images and moving images. These are selected and combined by the dentist, dental hygienist, etc. based on the patient or are selected and combined by the patient from a display of a treatment menu including treatment by implants, treatment by prosthetics, etc.

The selection may be performed by selecting the individual subdivided images and running them consecutively on a computer. Further, it is also possible to prepare several existing moving images selected in advance to enable the dental employee or patient to view them as combined moving images for explanation of treatment and see the states before treatment, after treatment, and sometimes during treatment.

These linked images can be formed to content tailored to the state of treatment of the patient himself or herself, so the effect of greater understanding and promotion of efforts for prevention of tooth decay etc. can be expected. Such partial moving images and images of the patient captured by camera means may be converted to the same image format for use. A treatment system which is easy for the patient to understand and which is easy for the dentist or other user to use is therefore provided.

Advantageous Effects of Invention

The present invention enables the display of part or all of rows of teeth by a clear panoramic image using the actual image and further, sometimes, enables display of an X-ray image superposed or in parallel, so that display can be used to explain to a patient the diagnosis and treatment in an easily understandable manner.

Further, the present invention enables the image capturing position of an intraoral camera which uses a reflecting mirror to be accurately displayed and enables the capturing posture of the camera unit being moved up and down in the oral cavity to be learned and adjusted to a state facilitating viewing of the captured image.

A patient can constantly check the situation in his or her own oral cavity and the necessity of diagnosis and treatment by a portable display means by which these are displayed on paper or in a recording medium in a list format. Due to this, the possibility of on-going diagnosis and treatment and care for maintaining intraoral health becomes higher and the profits in the dental practice can be increased and other facets of business can be improved.

The present invention further enables all processing in the dental practice to be handled using a mobile terminal able to process digital data and therefore enables rationalization of work and reduction of costs.

BRIEF DESCRIPTION OF DRAWINGS

FIG. 4 is a schematic view for explaining an embodiment.
FIG. 5 is a block diagram for showing another embodiment of the present invention.
FIG. 7 is a schematic view for explaining an embodiment.
FIG. 12 is a schematic view for explaining en embodiment.
FIG. 14 is a schematic view for explaining an embodiment.

DESCRIPTION OF EMBODIMENTS

Figure 1A:
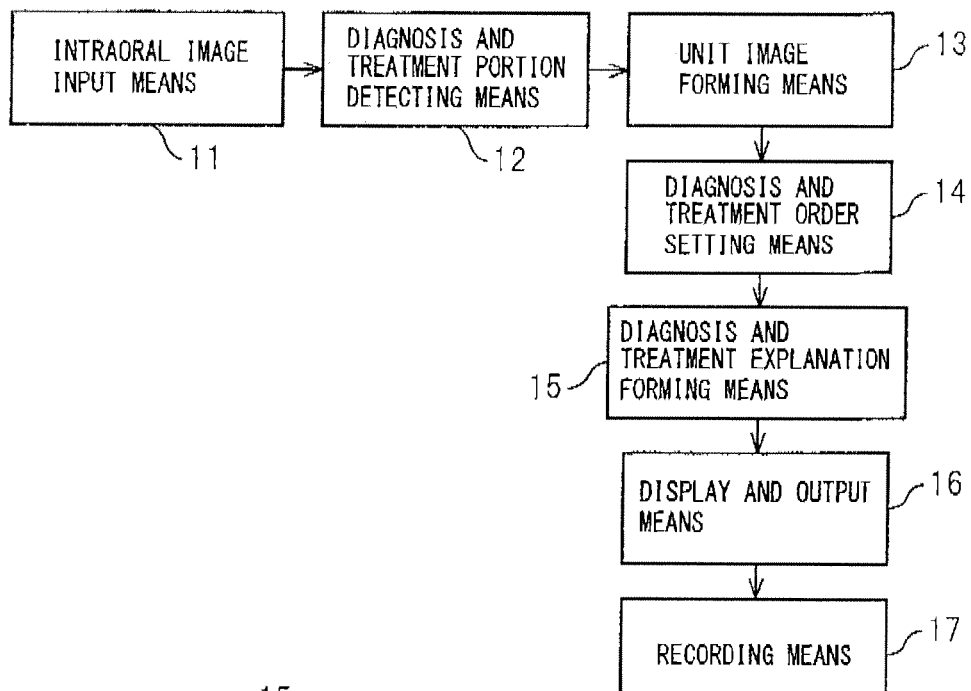
FIG. 1 is a block diagram for showing an embodiment of the present invention.

Next, various aspects and embodiments for working the present invention will be explained in detail while referring to the drawings. However, the present invention is not limited to only the aspects described below. It should be understood that various changes and improvements may be made within the scope of the present invention.

The present invention continuously captures images of rows of teeth, uses panoramic image combination to form partial panoramic images, and combines these partial panoramic images to form an overall panoramic image of the rows of teeth. Preferably, marks are provided at the combined parts. By doing this, it is possible to easily form a panoramic image of rows of teeth by a handheld camera.

The present invention acquires a unit image corresponding to diagnosis and treatment or care from intraoral images which are captured at the time of dental diagnosis and treatment or examination and diagnosis by using an intraoral camera or X-ray camera system and intraoral images captured at the home. This unit image is for example shown on a computer monitor (display) device which enables viewing together with the patient. The patient views the state inside the oral cavity. While doing this, he or she works with the dentist to enter the order of diagnosis and treatment, the period of start of treatment, the degree of necessity of diagnosis and treatment, etc. The obtained diagnosis and treatment and care order information and unit image are printed out on a single sheet of paper or stored in a mobile phone which is provided with a storage medium and displayed on the monitor of the mobile phone. Alternatively, it is uploaded to a homepage of the dentist and displayed on an individual's own screen.

The present invention provides a portable, wearable mobile terminal which includes inside it a storing means, computer, modem means for communication with the outside, and display means so as to enable input/output and data processing for the dental practice as a whole. Using this, it is possible to manage attendance of dental employees, make entries into electronic patient charts, calculate diagnosis and treatment fees, and have dental employees perform other work at their handheld terminals and share this information. The mobile terminal is connected with a host terminal wirelessly by infrared, light, or other media or is connected by a cable. Alternatively, the mobile terminal may be connected through a wireless LAN, wired LAN, etc. to a cloud computing computer network by designing it to have computer specifications.

First Embodiment

FIG. 1A is a view which, shows an embodiment of the present invention. In the figure, reference numeral 11 indicates an intraoral image inputting means, for example, a device which uses a camera for capturing images of all teeth of the upper jaw and lower jaw so as to obtain digital image data.

Figure 3A:
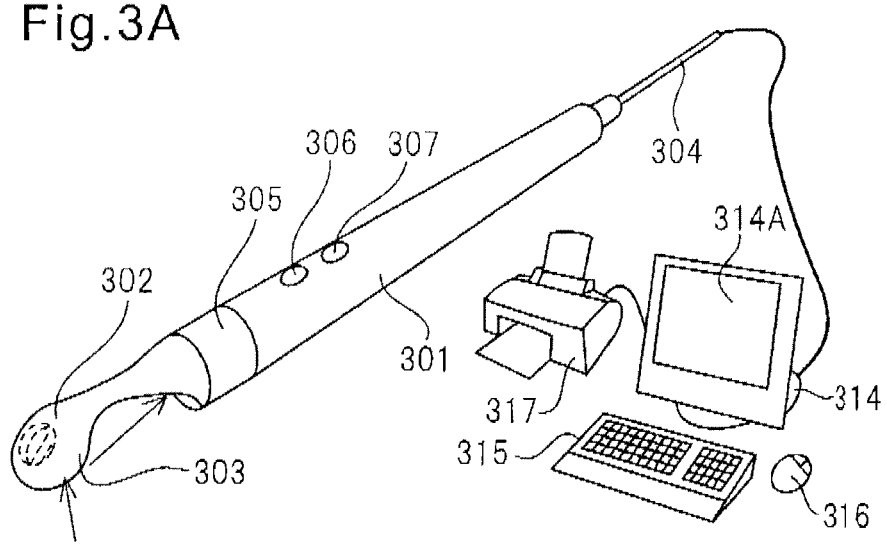
FIG. 3 is a schematic view for explaining an embodiment.
Figure 3B:
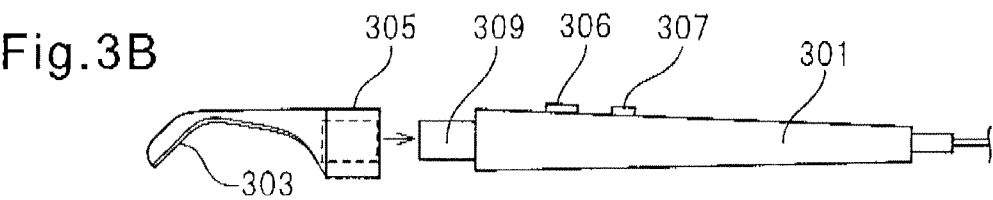
Figure 3C:
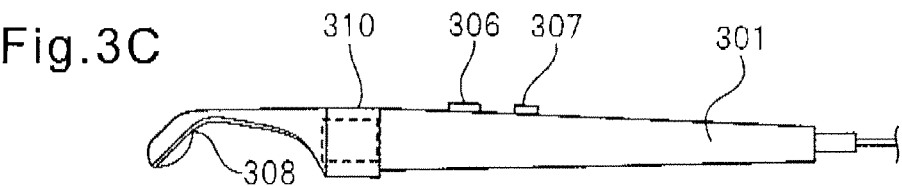
Figure 6A:
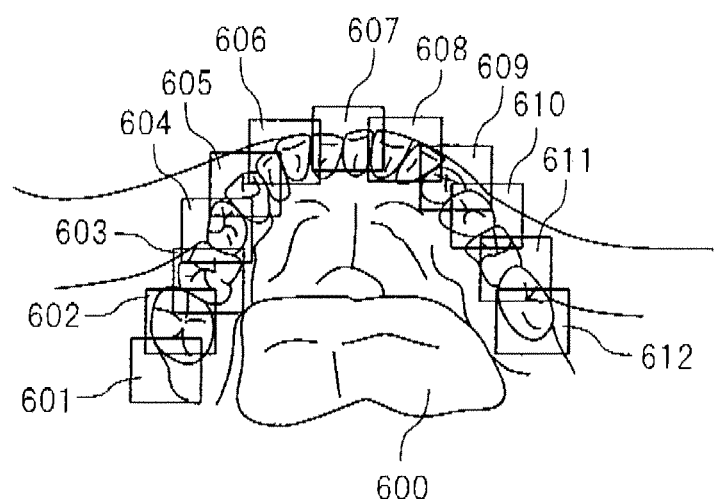
FIG. 6 is a schematic view for explaining an embodiment.
Figure 6B:
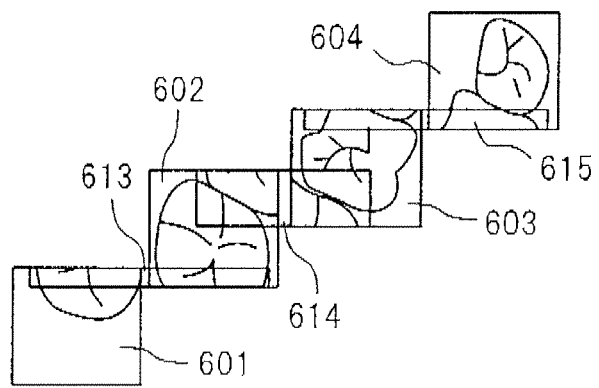

The intraoral image inputting means 11 is, for example, a reflection type of dental camera which uses a convex mirror such as shown in FIG. 3C or another camera for capturing an image of the oral cavity using a fisheye's lens and outputs a digital image of all teeth. Alternatively, as shown in FIGS. 6A and 6B, it is possible to use an ordinary intraoral camera to capture images of the individual teeth, extract contours from the individually captured images, connect the contours at the shared parts, and combine the images to obtain an overall image of the teeth.

Reference numeral 12 indicates a diagnosis and treatment portion detecting means. This, for example, is for setting a tooth for diagnosis and treatment or for care and a predetermined range of that tooth. This cuts out and extracts a tooth from a broad range intraoral image, which has been input by an intraoral image inputting means 11, by visual inspection while using graphics software. Further, it extracts and finds the contour of the tooth by software processing, assumes the extracted contour to be a circle and, finds its center, and extracts an image of a radius 10% to 20% larger than the radius of the contour from that center.

Reference numeral 13 indicates a unit image forming means. This processes the image for diagnosis and treatment, which was obtained by the diagnosis and treatment portion detecting means 12, for display use. This is for forming an image with a region for entry of the diagnosis and treatment order and comments. The unit image forming means 13 automatically creates and displays templates by designation of the diagnosis and treatment portion by the above-mentioned diagnosis and treatment portion detecting means 12 by operating icons by software.

The image which is shown is sometimes just a designated range of the image which was input by the intraoral image inputting means 11. It may also be a separately prepared template for unit image display which the user himself or herself designates. The image may further be one which is displayed after being captured by a suitable camera which uses a reflecting mirror which is shown in FIG. 3 at the time when the unit image is displayed. The image may also be initially displayed as a moving image in the unit image area and then confirmed and displayed as a still image by pressing a confirmation button.

Reference numeral 14 is a diagnosis and treatment order setting means. For example, the state of advance of tooth decay or the degree of diagnosis and treatment and care may be used as the basis for the dentist to determine the order on his or her own or in consultation with the patient or by automatic measurement of the state of advance of tooth decay or degree of deformation of shape. For automatic determination of the order, it is possible to convert the difference in color of the teeth to a numerical value for comparison with a certain threshold value or determine when a degree of deformation has exceeded a basic shape of a tooth by a certain extent or more or when the size of a spectral component based on the wavelength to an illumination light source of the tooth decay detection wavelength is a predetermined value or more so as to determine the order. The order of the images may be changed on the screen of the monitor (display) device.

The above mentioned changes are talked over with the patient, then the order of treatment and diagnosis is determined, so by pushing the confirmation button after determining the order, the order of unit images which are placed on the screen is automatically changed and the result printed out for patient use, so the diagnosis and treatment time can be streamlined.

Reference numeral 15 indicates a diagnosis explanation forming means. In the same way as the diagnosis and treatment order setting means 14, this is a means for entering the time of start of diagnosis and treatment, the urgency of diagnosis and treatment, the diagnosis and treatment technique, and other content which the patient believes necessary as data. This may be entered by input from a keyboard of a computer (for example, 315 of FIG. 3), selection of set explanations by operation using a mouse (for example, 316 of FIG. 3), or input by connecting operating buttons of the intraoral camera which is shown in FIG. 3 with the input interface of the computer and in that state operating the buttons attached to the camera body.

The diagnosis explanation forming means 15 has the date of start of diagnosis and treatment or scheduled date of diagnosis and treatment entered from the cells 21b to 23b which are shown in FIG. 2⊖ to FIG. 2F, but it is also possible that the earliest date enabling diagnosis and treatment be automatically displayed for that date.

The earliest date enabling start of diagnosis and treatment may also be set by a function of calling up the diagnosis and treatment scheduled start date entry fields from the database of patients recorded and stored in the recording means 17 and displaying the earliest date among the dates with no entries.

The specific configuration is shown in FIG. 15. This is part of the configuration of the diagnosis explanation forming means. The rest is omitted. Reference numeral 151 indicates a patient database callup means. This is a database in which the image data which is shown in FIG. 2, the order data, data on the date of start of treatment (including time), and explanatory data are recorded. This is managed as is general practice, so related data is recorded in a temporary recording region. This may be configured so that when the stored data is voluminous, data is called up to the database for each examination.

The earliest diagnosis and treatment date searching means 152 calls up the diagnosis and treatment start date data from this and searches for a date where no diagnosis and treatment start date is entered from this starting from the search start date. When there is data which does not match it, this is output as the earliest diagnosis and treatment date.

Reference numeral 153 indicates an earliest diagnosis and treatment date display means which displays a date searched for and detected by the earliest diagnosis and treatment date searching means 152 on the display part of the unit image.

Reference numeral 154 indicates an open diagnosis and treatment date display means which displays the open dates and times of diagnosis and treatment in an easily understandable format. For example, an analog clock and calendar can be schematically displayed or otherwise a computer monitor can be made to display units of months, units of several months, or units of years.

Reference numeral 155 indicates a decision input means for input of the consent of the patient and recordal of it in the database.

Reference numeral 156 is a recording means for recording to a database. This recording means 156 is the same as the recording means 17. Input may be recorded as finalized in the recording means 17, but the date and time of diagnosis and treatment have to be quickly recorded in the database since there is a possibility of another dentist simultaneously setting up a schedule like that of the patient. Therefore, as soon as the decision is made, it is preferably recorded in the database.

Returning again to FIG. 1A, 16 is a display and output means for editing and displaying images comprised of unit images, diagnosis and treatment orders, and diagnosis and treatment explanations on a screen of a computer monitor (display) device or using a printer (for example, 317 of FIG. 3) to print edited images on paper.

Reference numeral 17 is a recording means for recording the edited image data. It records it as part of an electronic patient chart stored by the dentist or records it in a patient mobile phone or computer through a storage medium. The recording means 17 includes a database which stores data of all of the patients from data of the individual patients.

Next, one example of an intraoral camera will be shown by FIG. 3 and explained.

Reference numeral 301 is a housing for holding use. It is shaped as a tube so as to form a pencil type intraoral camera. Inside, a circuit board, a USB connection circuit for connection with the outside, and a USB socket are contained.

At the front end, a camera unit 309 is integrally connected. For example, as shown in FIG. 3E, the camera unit 309 has for example a COD camera arranged at its center and has white LEDs and other color LEDs and other illumination devices 312 arranged around it in a concentric circle at equal intervals.

Reference numeral 302 is a reflecting mirror unit. At its front end, a flat mirror 303 which is arranged at a for example 45 degree angle is connected. At its back end, a tubular part 305 is formed in a state enabling insertion into the outer circumference of the camera unit 309 and enabling replacement. The outer shape of the camera unit 309 and the inner shape of the tubular part 305 of the reflecting mirror unit 302 are preferably made elliptical so that the parts will not rotate when fastened by insertion with each other.

The reflecting mirror unit 302 can be suitably replaced. FIG. 36 shows the state where a reflecting mirror unit provided with a flat mirror 303 is attached, while FIG. 3C shows the state where a reflecting mirror unit 310 where a spherical surface shape convex mirror 308 is attached is inserted into and joined with the camera unit 309.

When capturing all of the teeth in this way, the reflecting mirror unit 310 which has the convex mirror 308 of FIG. 3C connected to it is used. The convex reflected video of the convex mirror 308 is captured by the camera 313 of the camera unit 309. The output light of the illumination device 312 is reflected through the convex mirror 308 to light up the observed portion of the oral cavity. The camera 313 is illustrated as a CCD type, C-MOS type, etc. For the resolution, a higher image quality is preferable, but when mainly capturing a moving image, the image quality may be kept low in use.

In the case of normal image capture, the tubular part 305 of the reflecting mirror unit to which the flat mirror 303 which is shown in FIG. 36 is attached is inserted into the outer circumference of the camera unit 309 to join it for use.

Reference numeral 304 is a lead line such as a dedicated electrical lead line or a general use USB cable etc.

Reference numerals 306 and 307 are operating buttons. These are one or more push type, rotary type, composite type, or other buttons. In the present embodiment, two are shown. In addition to turning the power on or off or otherwise operating the camera, sometimes a selection and operation use display window which is displayed on a monitor 314A of a computer 314 which is connected through a lead line 304 is operated by pressing this operating button 307 in a GUI (graphical unit interface) function. For example, the operating buttons 306 and 307 can be operated when automatically rearranging the unit images in order after the order has been determined.

For example, reference numeral 306 may be made a button corresponding to the left click function of a mouse and 307 may be made a button corresponding to the right click function.

Reference numeral 314 indicates a computer which is formed integrally with a monitor (display) 314A as one example. In addition, it may also be combined as a dedicated device.

Reference numeral 315 indicates a keyboard, while 316 indicates a mouse for a computer. Both are used for operating the computer. Furthermore, they may also double as switches for operating the intraoral camera.

Reference numeral 317 indicates a printer. It is formed by an ink jet type or laser type color printer etc. and is used when printing out a patient's own intraoral image to give to the patient.

Figure 3D:
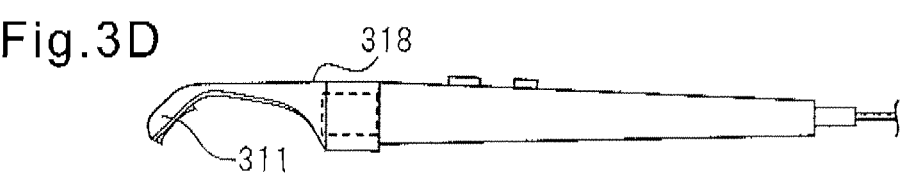
Figure 3E:
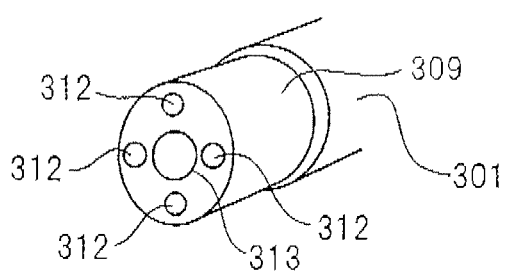

FIG. 3D shows a reflecting mirror unit 318 which uses a concave mirror 311 as a reflecting mirror. For example, this is used when an enlarged image is required. Alternatively, in the case of an oral cavity, when capturing enlarged only the inside of the rows of teeth, sometimes the curvature of the concave mirror 311 is adjusted to a direction close to a flat mirror and the rows of teeth are captured from a location somewhat separated from it so as to obtain a wide range image shown in the present invention.

In the present invention, sometimes not just the rows of teeth but also the tongue, lips, gums, etc. included in a wide range image are handled as a unit image. For example, the present invention can be suitably utilized in the case of displaying a polyp, which can be a manifestation of tongue cancer, as a unit image and explaining diagnosis and treatment.

Next, the present invention will be explained while referring to FIG. 6 which shows one example for forming an overall tooth image. The camera which is used is one using the reflecting mirror unit 302 using a flat mirror 303 such as shown in FIG. 3B, alternatively, the image may be captured as a still digital or may be captured as a digital moving image. Furthermore, when obtaining a plurality of still images from a digital moving image, since this is for capturing a moving image, the number of pixels becomes relatively small, therefore it is preferable to capture still images by an auto catcher while moving.

All of the teeth of the lower jaw 600 which is shown in FIG. 6A are captured while making the flat mirror 303 of the reflecting mirror unit 302 move in the direction from the capture planes 601 to 612. When capturing a digital moving image, the result is similar to the case of inputting still images at a rate of about 30/sec, so if the reflecting mirror part of an intraoral camera for capturing a digital moving image is made to move along a path from the image capture planes 601 to 612 of FIG. 6A, a large number of still images can be found. Further, continuous capture of still images gives a greater number of pixels and a higher resolution than acquisition of still images by capture of a moving image, so this is a preferable mode when acquiring images of individual teeth from this overall tooth image.

FIG. 6B shows parts of the individual images when performing a capture operation which is shown in FIG. 6A. Reference numeral 613 indicates an image of a common part of the images 601 and 602, 614 indicates an image of a common part of the images 602 and 603, and 615 indicates an image of a common part of the images 603 and 604. In addition, the capture operation is performed so that images of common parts are obtained for 604 and 605, 605 and 606, 606 and 607, 607 and 608, 608 and 609, 609 and 610, 610 and 611, and 611 and 612.

For example, these images are digitalized to obtain the contours, then are superposed so that the contours of the common parts match between images. Furthermore, the images 605, 606, 607, 608, 609, 610, 611, and 612 are successively captured and these images are linked based on their mutually common parts to obtain an overall tooth image. A panoramic type image of the bite plane can be formed by known panoramic image combining software, but when there is the effect of shaking due to holding the camera by the hand, the images are corrected before combination, so sometimes processing by affine transformation is preferable.

Next, the operation of the above embodiment will be explained in detail while referring to FIG. 2.

Figure 2A:
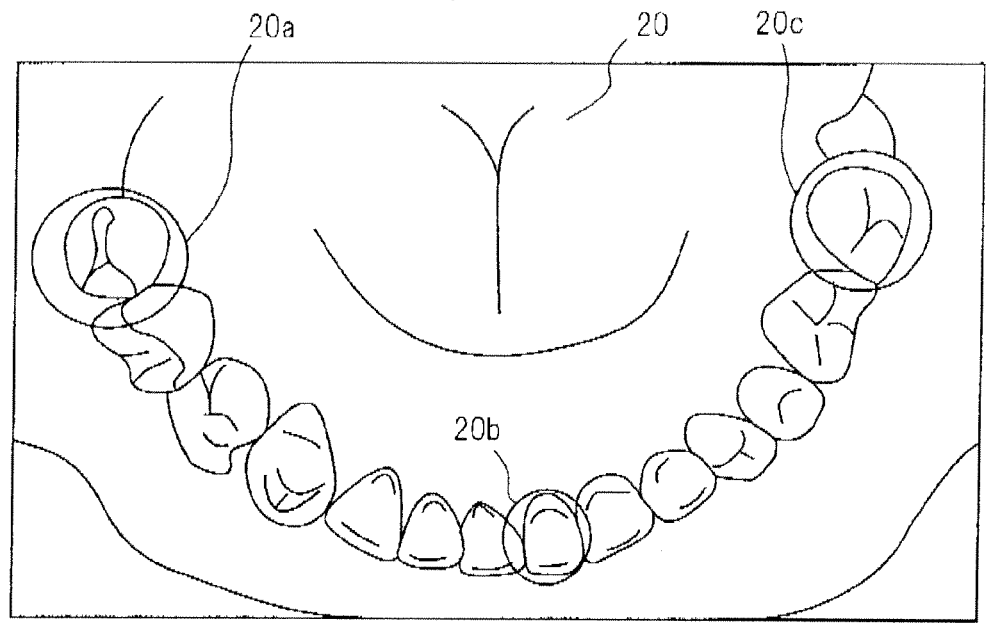
FIG. 2 is a schematic view for explaining an embodiment.

The intraoral image inputting means 11 is used to capture an image of for example the entire teeth of the upper jaw in the oral cavity. The position of the captured image is shown in FIG. 2A. The intraoral image inputting means 11 need only obtain an image which includes the tooth which the dentist is diagnosing and treating and which enables to which part in the oral cavity this corresponds to be understood.

The image which is shown in FIG. 2A, for example, is captured by the intraoral camera unit which is shown in FIG. 3C which is shown in FIG. 3C. Furthermore, it is possible to calibrate this so as to correct for distortion. Alternatively, the intraoral image inputting means 11 does not necessarily capture all of the teeth. It may also capture part of the teeth or a single tooth. FIG. 2A shows the upper jaw 20 and captures all of the teeth and the hard palate part. This portion is sometimes both diagnosed and treated.

Next, the diagnosis and treatment portion detecting means 12 is used to automatically or manually extract a portion requiring diagnosis and treatment or care. If extracting it manually, in the same way as graphic software, a mouse is used to designate this portion by a circle or square, then the portion is copied, cut, etc. and furthermore pasted. In FIG. 2A, 20a, 20b, and 20c indicate the state of using graphic software to manually or automatically designate and display a tooth to be covered by a conspicuous color circle.

"Manually designate and display" is to operate a mouse or keyboard which is for example attached to a computer so as to draw a circle, square, or other contour etc. and process the inside, while "automatically designate and display" is to for example use a mouse to Move a point to a designated portion on the screen and press a button so as to display a circle of a predetermined radius or a square of a predetermined area and process the inside.

Figure 20:
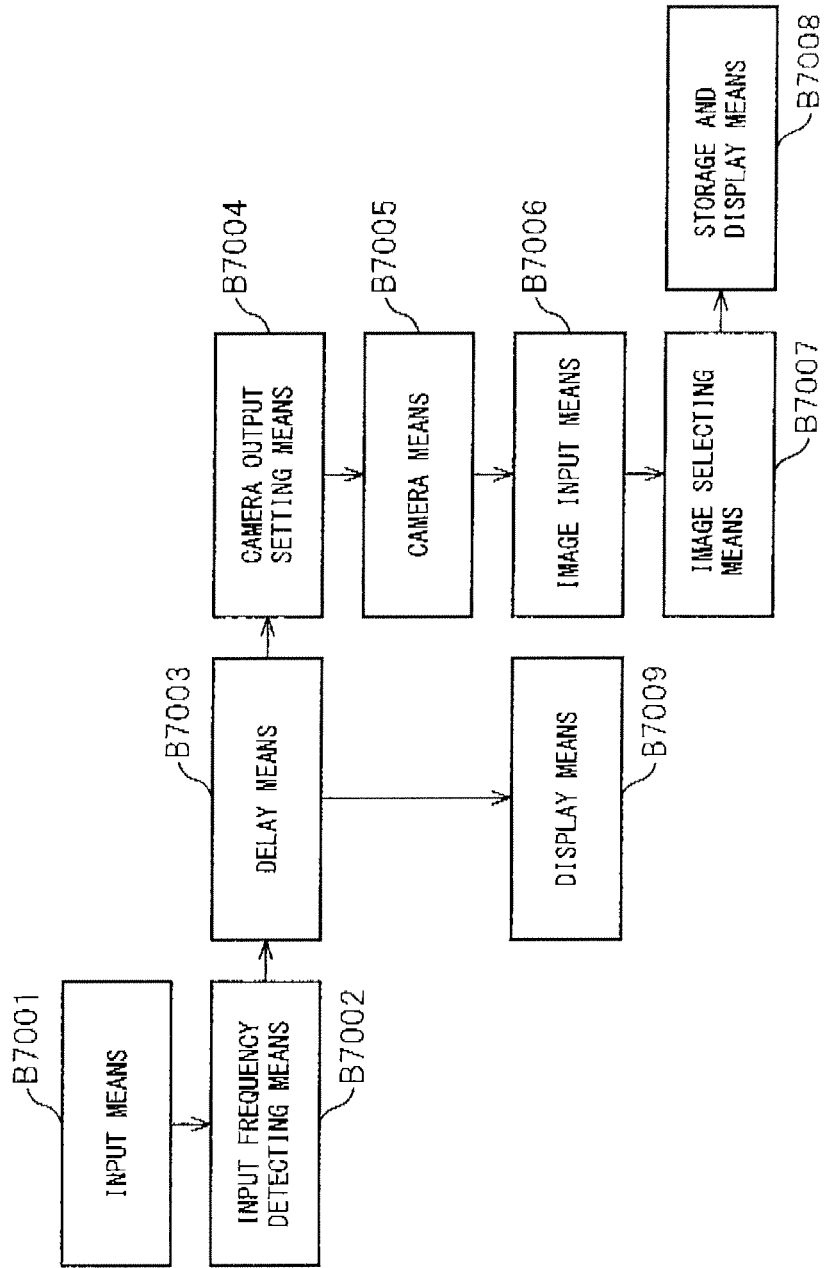
FIG. 20 is a block diagram for explaining an embodiment of the present invention.

Next, the unit image forming means 13 adjusts the designated tooth 20a which is shown in FIG. 20 to a unit image 21. At that time, for example, an order field 21a in which the order of treatment is entered after the order is determined, a diagnosis and treatment start date field 21b in which for example the start of treatment is entered after it is determined, and an explanatory field 21c in which what kind of diagnosis and treatment are to be performed is entered are additionally set. This earliest diagnosis and treatment date is, for example, displayed in the diagnosis and treatment start date field 21b of the unit image earliest in order in FIG. 2. If the patient consents to this date, the operation shifts to the decision input means 155 which decides on this date and records it in the patient database by the recording means 156.

If the patient does not consent, the open diagnosis and treatment date display means 154 displays the open diagnosis and treatment dates in a 2D form like a calendar format. This display may be of a list type, a page flipping type, or other type employing display of a schedule. It is sufficient that it at least be a display which the patient can easily understand.

Note that, not only the date, but also the time is required, so the time is also preferably displayed simultaneously. If agreement is reached on the date of start of diagnosis and treatment based on this display, the decision input means 155 is used to input that date and time and the recording means 156 is used to record them in the database.

The next unit image in order is shifted to and a similar date of start of diagnosis and treatment is decided and entered.

This scheduling operation of the diagnosis and treatment date is effective for clarification of the schedule since when the present invention sets a plurality of scheduled diagnosis and treatment dates, it is necessary to avoid conflicts with schedules of other patients—which does not occur with single-instance diagnosis and treatment.

Note that, the ID number may be entered in any field for each tooth. This field is for example an input use box display used in the database. The diagnosis and treatment date can be automatically determined, as a date which is open in view of the diagnosis and treatment schedules of other patients, so when a unit image is displayed, the open time slots may also be displayed from the data of patients. The content which is displayed in a window may be the image before treatment with fields in which at least the order of treatment is displayed or in which ID codes are attached.

Figure 2B:
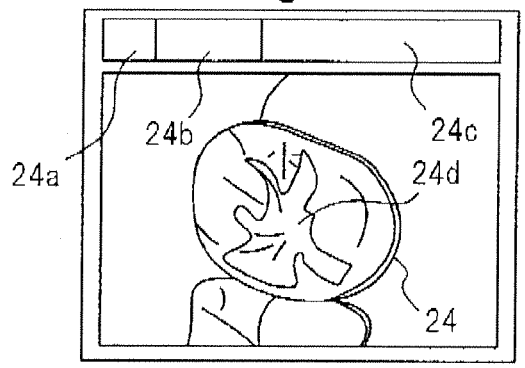
Figure 2D:
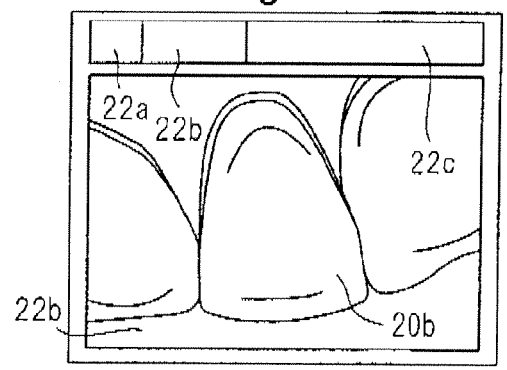
Figure 2C:
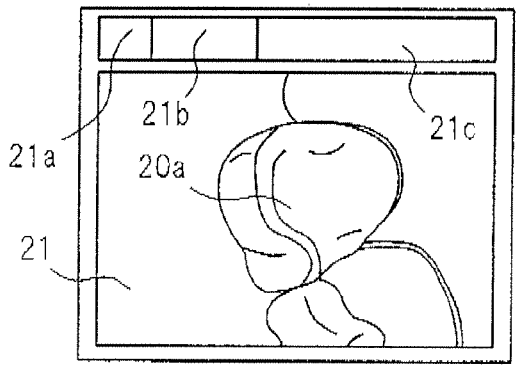
Figure 2E:
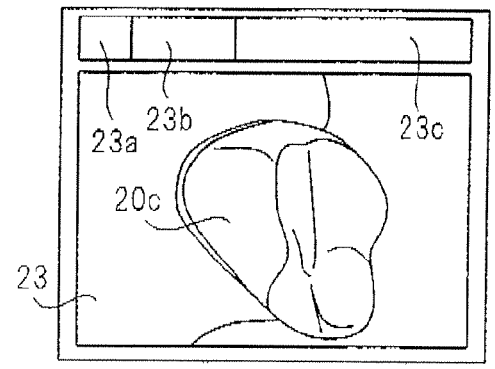

FIG. 2D shows a unit image 22 which shows a tooth 20b for diagnosis and treatment of FIG. 2A, while FIG. 2E shows a unit image 23 which shows a tooth 20c for diagnosis and treatment of FIG. 2A.

The unit image 22 displays an order field 22a, diagnosis and treatment start date field 22b, and explanation field 22c all together. FIG. 2E similarly shows a unit image 23 which shows an order field 23a, diagnosis and treatment start date field 23b, and explanation field 23c all together. Note that, when finalized, a confirm button (including a virtual button which is displayed on the screen) is pressed. By pressing the confirm button, the display may be rearranged along the numbers in the order entry fields. By automating this work, in the final analysis, the time for preparing the paperwork to be handed over to the patient can be shortened.

The view which is shown in FIG. 2 sometimes is shown in its entirety on a single computer monitor. In this case, this sometimes doubles as the operating range of the display and output means 16.

In the diagnosis and treatment order setting means 14, the order in the order field 22a is determined and entered by the dentist alone or by the dentist and patient in consultation. Similarly, the diagnosis explanation forming means 15 is used to make entries into the diagnosis and treatment start date field 22b and the explanation field 22c. These entries include considerable specialized matter, so sometimes are made by the dentist alone in advance.

The display and output means 16 forms and displays on the computer screen the finalized plurality of unit images and state including all tooth images. The display and output means 16 preferably displays any dental diagnosis and treatment which are performed on the same screen when they are performed.

Figure 1B:
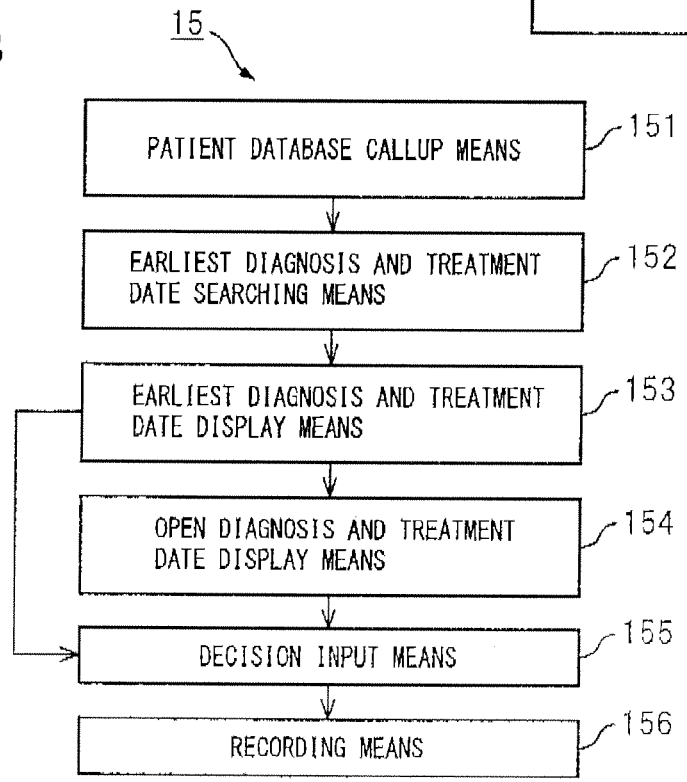

However, when there are many unit images, they may be displayed by scrolling or may, if necessary, be reduced in size or shown by thumbnails. Furthermore, the finalized image at the display and output means 16 may be printed by a printer on paper to be given to the patient. The patient can keep the image of his or her own oral cavity. This is expected to lead to regular visits to the clinic to maintain oral cavity health. Further, after diagnosis and treatment end, the image of the oral cavity is again captured as shown in FIG. 1.

The tooth 20a of the same portion is displayed as a unit image 24 as shown in FIG. 2B. Reference numeral 24d indicates the diagnosis and treatment portion, while 24a displays the order when, for example, the diagnosis and treatment order setting means 14 is used to search for the same image data from image data for which the diagnosis and treatment order has been set in advance and that order is shown. For example, the diagnosis explanation forming means 15 is used to describe the recorded matter etc. in advance at the time of diagnosis and treatment.

Further, the unit images after diagnosis and treatment which are shown in FIG. 2A can be displayed at locations adjoining the same unit images before diagnosis and treatment so as to increase the trust in the dentist and keep the patient aware of the timing for visits to the clinic for maintenance of the diagnosed and treated teeth. Reference numeral 24c indicates the explanation field for example after diagnosis and treatment. This is more preferably an explanatory field for consultation with the patient over the start of the next diagnosis and treatment.

Further, the display and output means 16 uses a printer to print out on a single sheet of paper for example the four images which are shown in 400 of FIG. 4. This is handled to the patient to impress on the patient the need, for continuous diagnosis and treatment. Note that, 400 does not show the intraoral wide range image which is shown in FIG. 2A, but preferably shows the wide range image so as to clarify the diagnosis and treatment portion and thereby obtain the further understanding of the patient.

The display fields of FIG. 2 and FIG. 4 are an example. The number of display fields per unit image and the displayed content are suitably selected in accordance with the purpose of the treatment, schedule, etc.

Second Embodiment

Next, another embodiment will be shown in FIG. 5 and explained. In the figure, reference numeral 51 indicates a wide range image inputting means. This is a means for capturing an image of all teeth of the upper jaw and all teeth of the lower jaw of the oral cavity. For example, it is possible to capture all teeth which are reflected in the convex mirror which is shown in FIG. 30 by a camera so as to obtain a wide range image or to continuously capture images shown in FIG. 6 and combine common parts from the still images forming the digital moving image so as to form a complete tooth image.

Reference numeral 52 indicates a tooth detecting means which extracts image data of respective teeth from the rows of teeth obtained by the wide range image inputting means 51. The extraction may, for example, be performed by a means using a contour extraction program to extract the peripheral sides in just a predetermined range to form an image of a single tooth and also by a means which uses the flat mirror which is shown in FIG. 3E to capture the individual teeth and form a single image, but the method of cutting out unit images from the overall tooth image and intraoral wide range image so as to form images of single teeth is both rational and preferable in some cases.

Reference numeral 53 indicates a unit image forming means which adds to the individual images obtained by the tooth detecting means 52 the respective order entry fields, diagnosis and treatment explanation entry fields, etc. to form the display use images. Furthermore, it is preferable to form a tooth database and attach unique codes to manage the teeth.

Reference numeral 54 indicates a diagnosis and treatment image selecting means for selecting a tooth for diagnosis and treatment of tooth decay, loss, etc. The dentist can visually, or through a comparison with previously registered data which is read out, select a tooth for diagnosis and treatment based on the differences in color, shape, etc.

Reference numeral 55 indicates a diagnosis and treatment order setting means by which the dentist decides on the order of the teeth for diagnosis and treatment on his or her own or by which the dentist and patient decide on this by discussion based on images displayed on a computer monitor (for example, monitor 314A of FIG. 3A) or printed images.

Reference numeral 56 indicates a diagnosis explanation forming means by which the period of diagnosis and treatment, date of start, and details of the diagnosis and treatment and the necessity of care etc. may be entered by the dentist alone or by consultation with the patient and by which explanations recorded in advance based on comparison with previous data may be displayed according to the magnitude of the differences.

Reference numeral 57 indicates a display and output means by which the display image for diagnosis and treatment may be displayed on a single sheet of paper or may be displayed on a computer monitor (for example, 314A of FIG. 3A) for use for explanations for obtaining patient consent and understanding. Alternatively, an image which is printed out on paper may be provided to the patient and used for scheduling future diagnosis and treatment so as to realize on-going dental diagnosis and treatment.

Reference numeral 58 indicates a recording means by which information may be recorded as a patient chart or database or by which information is uploaded to a storage area exclusively for the patient in a server. Tooth image data may also be recorded at the recording part of a mobile phone of a patient.

Next, the operation of the embodiment which is shown in FIG. 5 will be explained with reference to FIG. 7. In the present embodiment, a wide range image inputting means 51 is used to capture an image of all of the teeth from the oral cavity of a patient so as to form image data 700 of all teeth comprised of a single or multiple images (see FIG. 7A). The image data 700 which shows all teeth can be formed by linking the still images which are shown in FIG. 6 as one example. From the obtained, wide range image data 700, the tooth detecting means 52 manually or automatically forms tooth images.

As the technique for automatically detecting teeth, the intraoral image data may be processed by a contour extraction program to extract contours and detect the contours of the teeth. In this case, if the contours are incomplete, several points are detected and a virtual circle which passes through these points is formed. This virtual circle can be deemed as the position of one tooth, so the radius from the envisioned center can be enlarged by exactly a predetermined value and a square surface can be extracted as an image of one tooth.

The extracted images become, for example, as shown in FIG. 7B, the tooth image 701 for the tooth 71, the tooth image 702 for the tooth 72, and the tooth image 703 for the tooth 73.

Next, the unit image forming means 53 is used to link the images of these teeth with identifiers and other patient information for unit image formation (see FIG. 7C). A unit image 74 includes a tooth image 701 and a display field 704 for entering the diagnosis and treatment order etc. The unit image 75 includes a tooth image 702 and a display field 705, while the unit image 76 includes a tooth image 703 and a display field 706. These unit images are recorded in a preset patient database and form an upper and lower intraoral data list of the patient.

The diagnosis and treatment image selecting means 54 visually or automatically extracts from the unit images a unit image 77 which shows an image of a tooth for diagnosis and treatment or care (see FIG. 7D).

In the diagnosis and treatment order setting means 55 and diagnosis explanation forming means 56, which have configurations similar to FIG. 1 and perform similar operations, the dentist enters the diagnosis and treatment order etc. alone or preferably while viewing the unit tooth images displayed on a computer monitor together with the patient.

Further, when the diagnosis and treatment order has been determined and the date of start of diagnosis and treatment etc. has been entered, the display and output means 57 may also display on the computer monitor 78, for example, an array of unit images displayed in sequence as shown in FIG. 7E or, as shown in FIG. 7F, a wide range image further included in an edited state. It is therefore possible to create a situation where the patient confirms diagnosis and treatment and gives consent for on-going diagnosis and treatment.

The unit images 707, 708, 709, and 710 are preferably arranged in order of start of treatment. FIG. 7F shows, for example, a screen display including the entire tooth image data 711 or tooth data 79 printed out to enable the patient to carry it.

The recording means 58 records these unit images in the database and is suitably used for adjusting the schedule with other patients.

Further, the present invention may form a single image by combining the technique of using a convex mirror shown in FIG. 3 when obtaining a wide area image or the technique of making the reflecting mirror move along the rows of teeth and combining the still images. That is, by making only the rows of teeth a still image, capturing the tongue portion by using a convex reflecting mirror, and combining the images, an intraoral wide area image provided with distortion-free rows of teeth is obtained.

Furthermore, one example of a panoramic tooth row image forming technique which combines panoramic images of rows of teeth in a state with the teeth engaged so as to form a clear image is shown from FIG. 8 to FIG. 12.

As shown in FIG. 8, the technique is adopted of using a camera to capture images from the left back up to near the center, then changing the orientation of the intraoral camera to then capture images from the right back to near the center. In this case, the direction of the camera is changed once, so the capture operation is interrupted. Therefore, the left and right tooth row images often cannot be accurately combined and end up deviating from each other.

Further, when manually moving and operating a camera, for example, when capturing an image of the back teeth, the intraoral camera is made to move in a state arranged between the cheek at the inside of the oral cavity and the side surfaces of the teeth and pushing aside the cheek or a state of contact is formed with the side surfaces of the teeth. Therefore, the cheek and the side surfaces of the teeth are in a state where they support the reflecting mirror of the intraoral camera or the image capturing portion of the camera, but if the intraoral camera is made to move in the direction of the front teeth, the camera is released from the pinched state with the cheek etc. and becomes held only by the hand whereby the operating camera becomes unstable in position and the images easily become disturbed. In particular, the distance between the camera and the captured object, that is, the side surfaces of the teeth, fluctuates and shaking occurs in the image capturing direction whereby the captured objects, that is, the teeth, fluctuate in size or the images become distorted.

The intraoral camera 901 which uses the reflecting mirror which is shown in FIG. 8 is configured as shown in FIG. 3 as one example, that is, is configured by a modular CCD camera or CMOS camera around which a plurality of light source LEDs are arranged. The oral cavity is lighted by the light source LEDs through the reflecting mirror and images of the rows of teeth in the oral cavity etc. are continuously captured. Stable capture is possible from the back teeth, but the invention is not limited to this. It may also use a camera for direct image capture not using a reflecting mirror in some cases.

The intraoral camera 901 which is used here is illustrated as one which is configured with a reflecting mirror unit 903 (302 of FIG. 3) which is provided with a flat type reflecting mirror 902 (303 of FIG. 3) attached interchangeably at the front end of a body 904 (301 of FIG. 3). The body 904 is provided at its front end with a camera unit 905 (309 of FIG. 3) which combines a CCD camera, CMOS camera, or other camera and four to eight light emitting diodes arranged around the camera.

The camera unit 905 is illustrated as one which outputs still digital images by using the continuous capture technique so as to obtain a range of for example 10 to 30 still images per second.

Before starting the continuous capture, first a mark ML is attached near the center of the rows of teeth 900a in the state with the upper and lower teeth engaged with each other. The mark ML is preferably made by temporary adhesion of a colored seal, marking by a colored pen giving a color that can be removed, or use of another means giving a mark which can be clearly displayed in the image captured by the camera. "Near the center" when attaching the mark ML for example near the center of the rows of teeth indicates a location serving as a reference when continuously capturing the left and right tooth rows, then combining the images. In addition, it is also possible to detect a characterizing portion in image processing near the center of a captured image and set that portion as the mark in the image. The mark ML is preferably arranged so as to span an upper tooth and lower tooth.

This continuous capture operation is performed from the back tooth position, for example, the state of 906a, along the tooth surfaces like 906h and 906c, preferably separated by the same distance from the surfaces of the rows of teeth, while the body 904 is held by the hand and the reflecting mirror 902 is moved.

"IG" indicates a correction use indicator. This is comprised of an adhesive member which is attached to a tooth surface in a manner enabling it to be peeled off later. On this, a graphic for image correction use such as a box, square, triangle, or checkerboard may be displayed to enable correction of distortion of the image or correction of the relative size of images based on the distance between the camera and tooth side surfaces. Alternatively, the correction use indicator IG may be colored green or another color which can be discerned in image processing, but it is not limited to green.

This adhesive member may be attached at the center of a tooth such as shown in, for example, FIG. 8 and FIG. 10, at the surface of the tooth where the mark ML is made. Alternatively, the tooth attached to is not limited to a single tooth. A plurality of teeth may have the adhesive member attached for image capture. The adhesive member may sometimes also be attached to another tooth in the oral cavity where the teeth are to be captured by hand with no other support.

The means for attaching the correction use indicator IG to a tooth surface may utilize a similar technique to that of the mark ML. An indicator which will not dissolve and will not run in saliva etc. may be used as an example. This is preferable when correcting for distortion and size of and combining a partial panoramic image of the left rows of teeth and a partial panoramic image of the right rows of teeth based on the correction use indicator IG which is captured in common to the two. Note that, when combining three partial panoramic images of the left rows of teeth, the center rows of teeth, and the right rows of teeth, the teeth common to the partial panoramic images may be provided with auxiliary use indicators IG.

Individual captured still images may also be corrected. For example, based on a reference auxiliary use indicator IG in the continuously obtained images or using as a reference one of the auxiliary use indicators IG captured in a group of images and detected by the block matching method or the template matching method etc., the auxiliary use indicator IG captured in another image is detected, then compared with the reference image to detect distortion, tilt, and differences in size, then correction is performed using affine transformation which performs enlargement, reduction, rotation, and adjustment of movement. At the time of image capture by hand where shaking is unavoidable, the auxiliary use indicator IG may be attached to a tooth so as to enable stable combination for forming a panoramic tooth row image.

The above-mentioned such correction of an image using the correction use indicator IC may, for example, be performed by the method of Zhang (IEEE Transactions on Pattern Analysis and Machine Intelligence, 22(11); 1330-1334, 2000) and other techniques used, in calibration of camera images. Further, the correction use indicator TG sometimes is not essential depending on the captured state, affine transformation, or other processing.

Figure 8A:
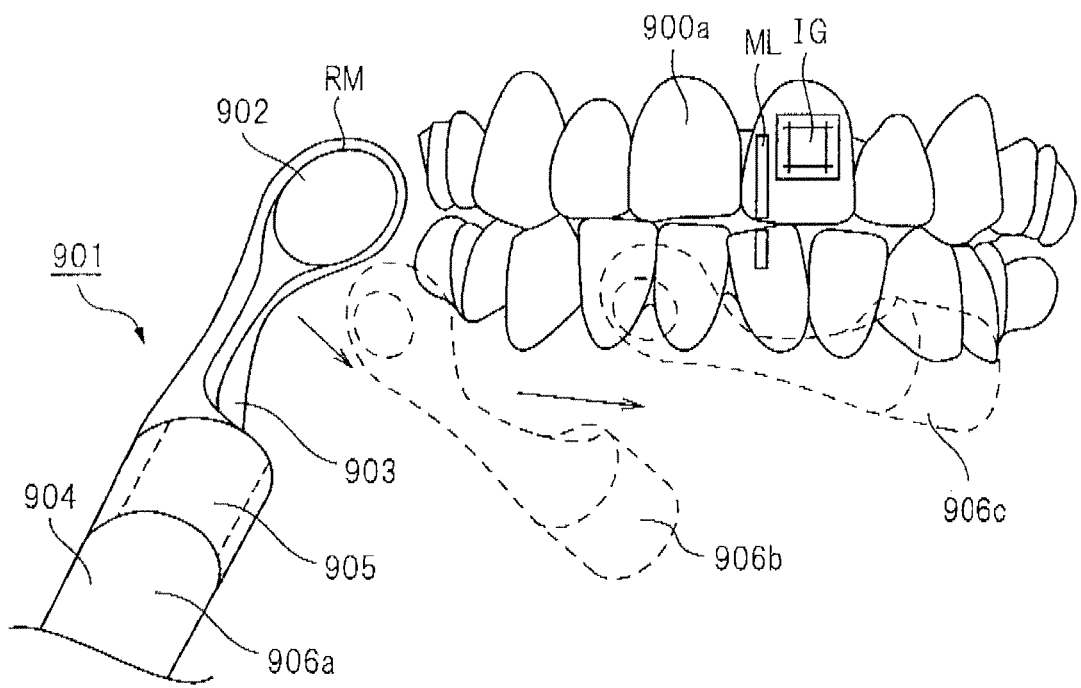
FIG. 8 is a schematic view for explaining an embodiment.
Figure 8B:
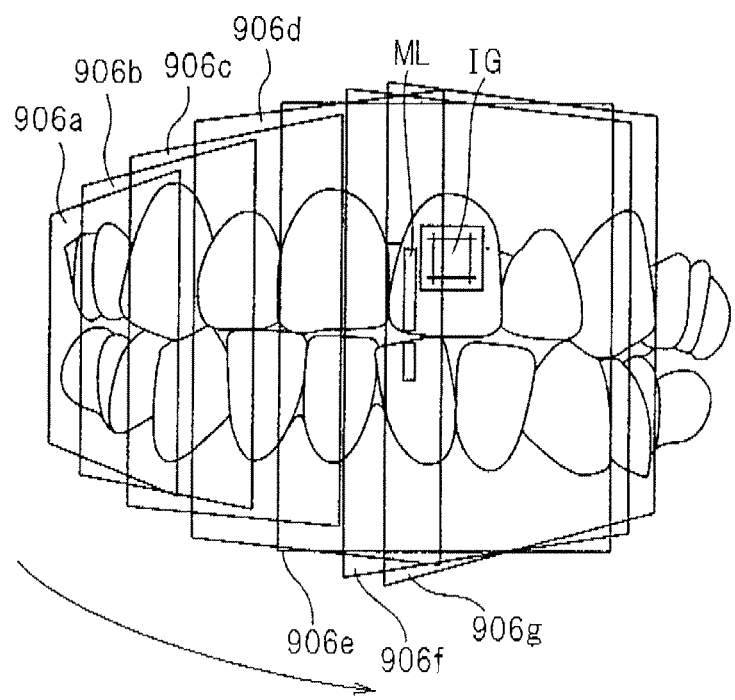

FIG. 8B schematically shows one image capture range when continuously capturing images from the back teeth. The reflecting mirror part of the intraoral camera is made to move along with the elapse of time such as by 906a→906b→906c→906d→906e→906f→906g while obtaining continuously captured images as still images.

The intraoral camera 901 is configured provided with a reflecting mirror 902 at the front end at a predetermined angle, so if capturing the surfaces of the row of teeth from the left back teeth in the figure, the direction of the body 904 is changed near the center and then the surfaces are captured in order from the right back teeth in the figure. Therefore, the surfaces of 906e to 906g shown in FIG. 8 are captured, then the intraoral camera 901 is reversed and starts to capture images from the right back teeth.

The speed of continuous capture is made capture of a slightly great 20 to 30 images per second since the body 904 is moved by hand and therefore the effects of hand shaking and other shaking should be considered. Continuous capture with enough extra leeway to delete images which are out of focus due to hand shaking is preferable.

This continuous capture is preferably performed until the mark ML reaches the center of the capture screen or the reflecting mirror, but sometimes it is performed until a portion exceeding that by a certain extent. After that, the captured images may be picked and discarded.

Since the camera is operated manually, before combination, sometimes, the common portions of the images are used as the basis for affine transformation so as to match the images in state. For example, using the image first becoming the center of combination as a reference, block matching is performed with a comparative image to detect a plurality of common points. Based on this plurality of common points, the next image is processed by affine transformation. For example, a plurality of pixel coordinates (xb, yb) of the next image corresponding to the pixel coordinates (xa, ye) of the reference image at the common part are selected and entered into the following formula to obtain the coefficient values "a" to "f". In the state entering the coefficient values into the following formula, the next image is processed by affine transformation to straighten out the images or the images are straightened out while combining panoramic images.

$$\begin{pmatrix} xa \\ y_a \end{pmatrix} = \begin{pmatrix} a & b \\ c & d \end{pmatrix} \begin{pmatrix} x_b \\ yb \end{pmatrix} + \begin{pmatrix} e \\ f \end{pmatrix} \quad \text{[Formula 1]}$$

Part of the images which are obtained by continuous capture from the left back to near the front surface in the figure in the rows of teeth 900a are shown in FIG. 9. Jointly using FIG. 8, the capture operation of an intraoral camera based on this embodiment will be explained.

FIG. 9A to FIG. 9E show one example of the sequence of captured image data when performing continuous capture near the centers 907c to 907e in the captured image data of the rows of teeth which are shown in FIG. 8B. Note that, the intraoral camera utilizes the reflecting mirror 902 to obtain a tooth row image, so the captured image is inverted left to right, but is shown in FIG. 9 and FIG. 11 in a non-inverted state so as to facilitate understanding.

Figure 9A:
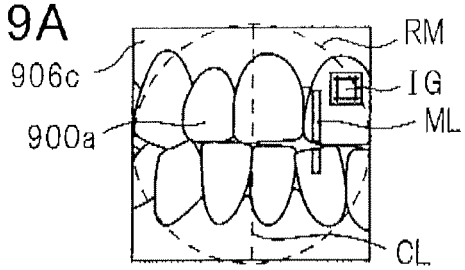
FIG. 9 is a schematic view for explaining an embodiment of the present invention.
Figure 9B:
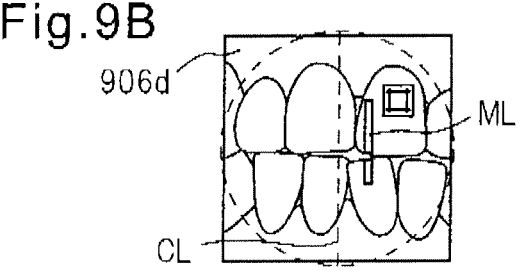
Figure 9C:
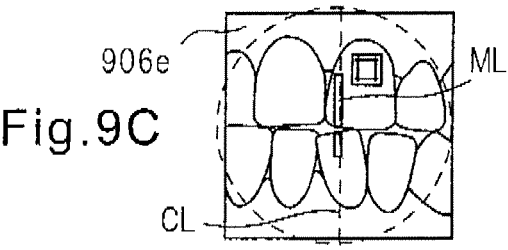
Figure 9D:
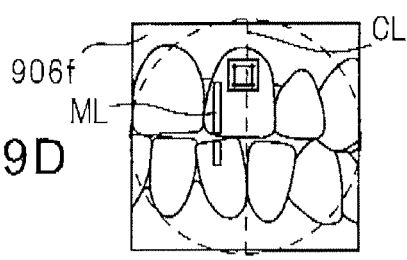
Figure 9E:
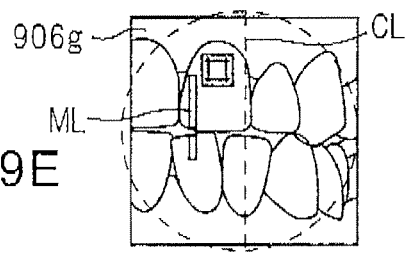

FIG. 9A is an image which captures the area near 906c of FIG. 8B, FIG. 9B is an image which captures the area near 906d, FIG. 9C is an image which captures the area near 906e, FIG. 9D is an image which captures the area near 906f, and further FIG. 9E is an image which captures the area near 906g. Note that, since the capture is performed manually, the captured images often cannot be captured in the same state at all times. Therefore, when the images are tilted etc., it is preferable to perform correction for matching states using affine transformation at parts for example overlapping with the states of other teeth. FIG. 9 shows the view after correction. At the time of correction, as portions serving as reference, in addition to the mark ML, the vertical centerline CL and horizontal centerline HL which are set in advance at the reflecting mirror surface at which the reflecting mirror 902 is captured may be used.

The vertical centerline CL and the horizontal centerline HL are not necessarily displayed at the image. Further, at the edges of the reflecting mirror, it is also possible to provide projections or other marks at portions corresponding to the starting points and end points of the vertical centerline and horizontal centerline. These marks are sometimes used as the basis for virtual display.

Further, it is also possible to simultaneously perform processing for correcting distortion caused by a CCD camera lens by software.

RM is the contour of a mirror. The actually captured image becomes a circular image in the contour RM, but is displayed as a square image so as to facilitate the explanation of the range.

The captured image sometimes differs in the distance between the teeth and camera since the camera is held by the hand. In this case, an image where the mark ML and the vertical centerline CL approximately match may be used as a reference to correct the size of another captured image. Note that, sometimes the front end of the reflecting mirror 902 is made to lightly contact the tooth surface while continuously capturing images so it is possible to stabilize the obtained images.

As shown in FIG. 8, the reflecting mirror 902 of the body 904 is arranged from the front surface to the back teeth of the left side and then is made to move in the direction of the front surface for continuous capture so as to obtain, for example, the images of FIG. 9A to FIG. 9E. In this case, the images which are obtained by capture at timings where the mark ML matches the vertical centerline (CL) of the reflecting mirror 902 (up to FIG. 9C (are supposedly employed as images for combination. If using FIG. 9O on, at the time of combination, sometimes these will cause deviation, so it is preferable not to use these for combination.

The image which is shown in FIG. 9C is corrected for tilt of the image etc. in accordance with need with reference to the mark ML used as the reference image. That is, the image may be corrected based on the long sides and short sides of the mark ML to obtain the reference image. One example of the combination operation will be explained below.

Figure 9F:
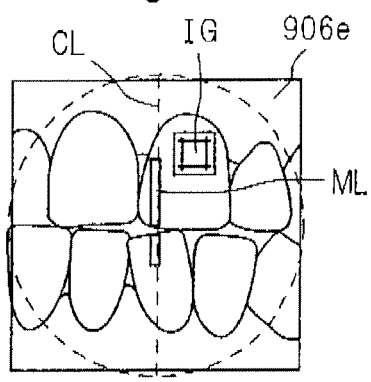

The images which are used for combination are shown in FIG. 9F on. FIG. 9F corresponds to the image which is shown in FIG. 9C, FIG. 9G corresponds to FIG. 9B, and FIG. 9E corresponds to FIG. 9A.

Figure 9G:
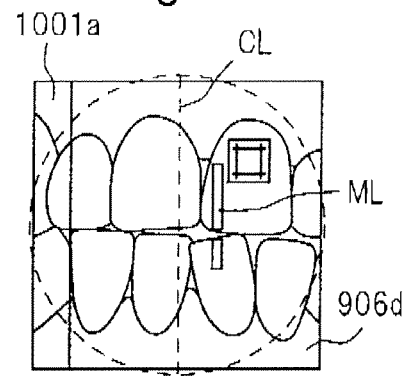
Figure 9H:
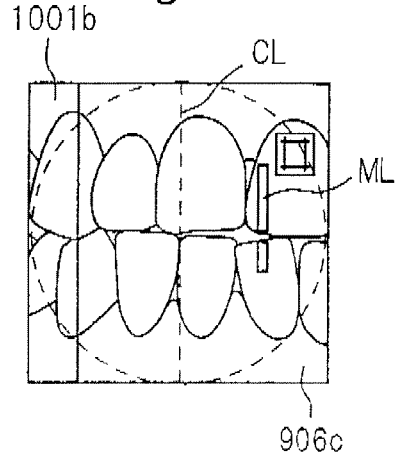

The image 906e which is shown, in FIG. 9F and the image 906d which is shown in FIG. 9G are combined by superposition based on common parts where the shape of the image of the image 905d matches or approximates the image 906e as a reference.

The part which sticks out in the left direction of FIG. 9G when superposed based on FIG. 9F is shown by 1001a. 1001a becomes the image in the back tooth direction.

Next, the combined image which is shown in FIG. 9G and the image 906c which is shown in FIG. 9A are superposed visually or by an image processing technique at parts of common shape etc. with reference to the combined image of FIG. 9G. In the superposed image, the part protruding in the left direction from FIG. 9G is indicated by 1001b. 1001b is an image in the back tooth direction.

The above operation is next performed between the next adjoining images. Furthermore, the next adjoining images are superposed at the common part. Due to this, the images from the image where the mark is at a predetermined position to the deep tooth direction are combined panoramically to form the left side rows of teeth.

In addition, the technique of splicing together the parts 1001a, 1001b . . . which protrude from the center image shown in FIG. 9F to form a left half panoramic image may be illustrated.

Further, the protruding parts are detected by, for example, extracting the protruding parts between 906e of FIGS. 9C and 906d of FIG. 9B, extracting the protruding parts between 906d of FIGS. 9B and 906c of FIG. 9A, furthermore collecting the protruding parts between the next adjoining images, and finally making the reference image the image shown in FIG. 9F and splicing together the protruding parts to form a panoramic image. The images of the protruding parts are sometimes preferably obtained by using an image from the center as a reference and superposing the adjoining images from it.

Note that, even when, not completely superposed and matching or approximate, if the marker part is present in common, that part may be superposed for similar combination. Further, since the operation is manual, there is a proximity feeling in the obtained still images and the tilt sometimes differs. In this case, it is preferable to use affine transformation etc. for automatic correction to enlarge or reduce the image for adjustment.

The combined state is shown in FIG. 12A. As shown in FIG. 12A, it is possible to form the left half of the panoramic image of the rows of teeth.

Figure 10A:
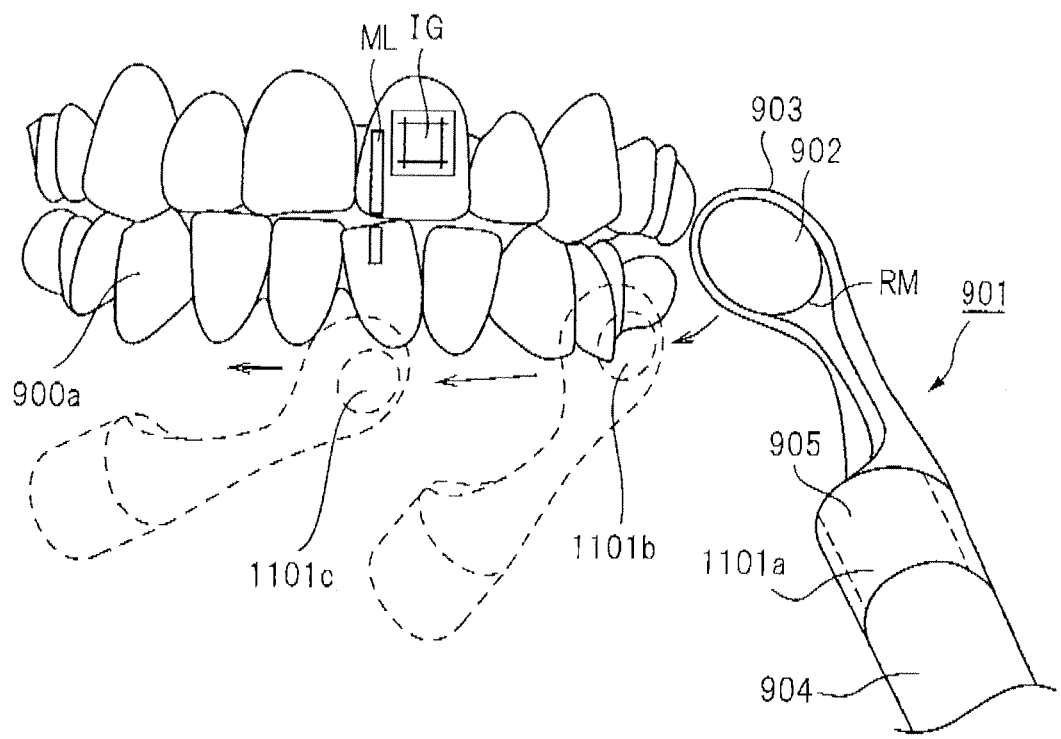
FIG. 10 is a schematic view for explaining an embodiment.

Next, as shown in FIG. 10A, the reflecting mirror 104 of the body 103d is arranged at the right back of the rows of teeth 900a in the state with the top and bottom engaged. In that state, while holding a certain distance from the surface of the rows of teeth 900a as much as possible, continuous capture is performed by still images at 1101a→1101b→1101c in a direction approaching the center. FIG. 102 schematically shows the positional relationship between the captured still images and the rows of teeth 900a.

The user holds the intraoral camera 901 in his or her hand while making it move in the direction of 1102a→1102b→1102c→1102d→1102e→1102f to capture images and obtain continuously captured still images. The present example is of a handheld type, so the captured image will tilt or shift to the left or right and in the back direction, but a step may be provided which utilizes affine transformation to rotate or move the image based on the common parts present between adjoining images obtained by continuous capture so as to adjust the image.

The intraoral camera 901 which is shown in FIG. 10A is the one of FIG. 8 used as it is, so the same reference notations are assigned and explanations are omitted.

In FIG. 11A to FIG. 11E, typical images are shown in the range of 1102a to 1102f of FIG. 102. Configurations which are common to FIG. 11 and FIG. 9 are assigned the same the same reference numerals as the reference numerals which are shown in FIG. 9.

Figure 10B:
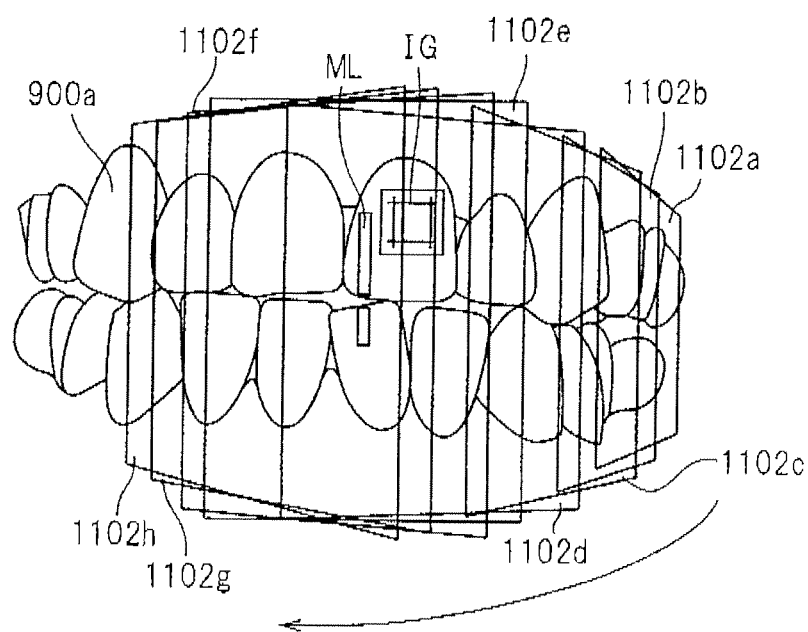
Figure 11A:
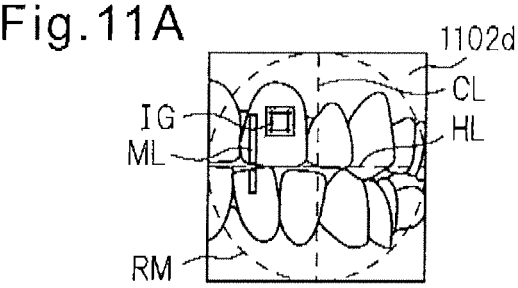
FIG. 11 is a schematic view for explaining an embodiment.
Figure 11B:
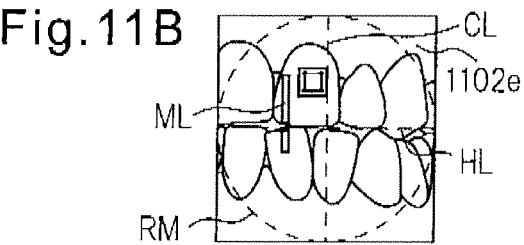
Figure 11C:
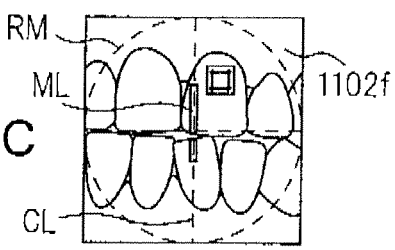

In FIG. 11, FIG. 11A shows the area near the image of 1102d of FIG. 102, FIG. 112 shows the area near the image of 1102e of FIG. 102, and FIG. 11C shows the area near the image of 1102f of FIG. 10B. Further, FIG. 112 shows the area near the image of 1102g of FIG. 10B, and FIG. 11E shows the area near the image of 1102h of FIG. 10B.

Figure 11D:
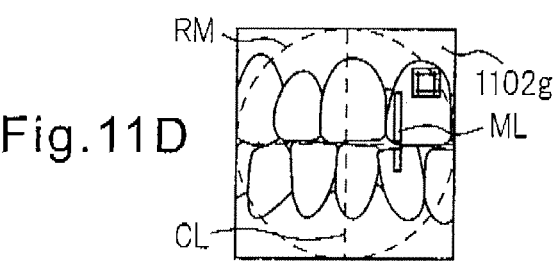
Figure 11E:
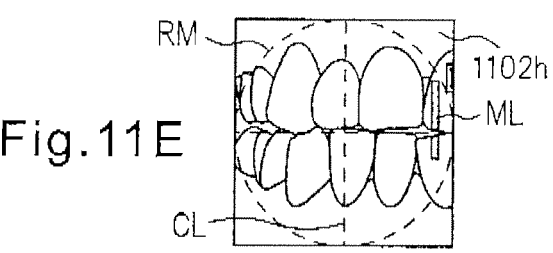

Note that, FIG. 11D and FIG. 11E are images of photos when the vertical centerline CL and the mark ML match, then the reflecting mirror 104 is made to move further in the left direction. If employing these images, the superposed parts of the images captured from the left and, right directions will become greater and the images will deviate, so these are not employed. FIG. 11A to FIG. 110 are employed.

Figure 11F:
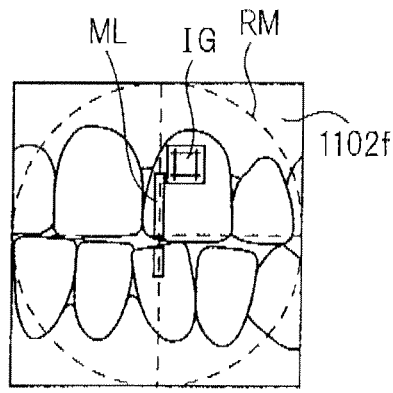
Figure 11G:
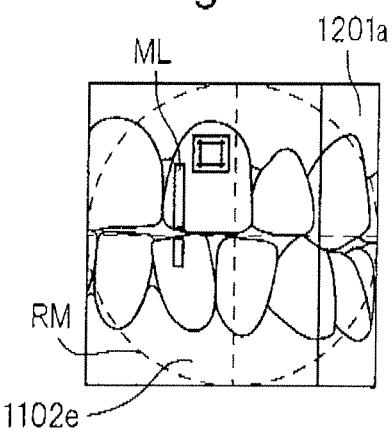
Figure 11H:
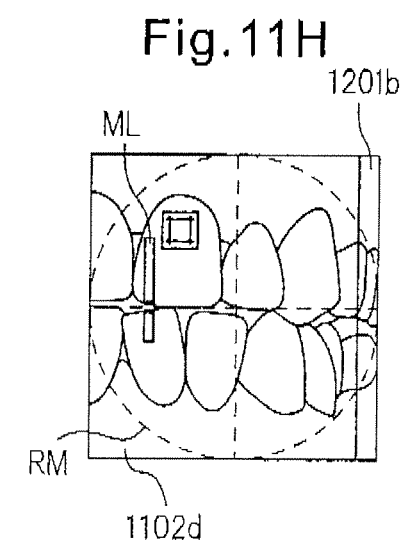

In the above images, the one using the image where the mark ML and the vertical centerline CL match (1102f of FIG. 11C) as a reference is shown in FIG. 11F. Next, the common portions of the images 1102e and 1102f shown in FIG. 11B are superposed.

In the state where the image 1102f is used as a reference and the image 1102e is superposed from above in a matching or similar range of shape, the protruding part is 1201a.

Next, this superposed image and the image 1201b which is shown in FIG. 11B are superposed with reference to the superposed image using pattern matching etc. at portions matching or substantially matching in shape.

The part which protrudes in the superposed state is 1201b. In this way, the adjoining images are superposed to form the right side rows of teeth. As another method of combination, the reference image 906e and images 1201a and 1201b may be combined as shown in FIG. 12B in some cases. Note that, when superposing front and back images, if there is some deviation, it is sometimes also possible to delete one of the superposed locations.

By using the above routine to combine continuously captured still images and superposing the center image 906e when combining the images of the left rows of teeth and the center image 1102f when combining the images of the right rows of teeth to make them match or substantially match, the panoramic image of the rows of teeth which is shown in FIG. 12C is formed.

The superposition is, for example, preferably performed by connecting and combining the left and right panoramic images of the rows of teeth based on the boundary part (KL) of teeth at the center. Note that, to deal with the case where the boundaries of teeth differ between the upper jaw and the lower jaw, the boundary part of teeth of the upper jaw or lower jaw may be used as the boundary for the combination.

The combination at that time may also consist of respectively combining the panoramic image of the row of teeth of only the upper jaw and the panoramic image of the row of teeth of the lower jaw and finally combining the upper jaw and the lower jaw. At this time as well, when there is some deviation between the center images, it is also possible to delete one of the images in the superposed range.

Further, it is not necessarily required to superpose the center image 906e and the center image 1102f in advance. In some cases it is possible to employ one of the center images 1301. In this case, when for example employing the center image 906e, sometimes the sizes of 1201a and 1201b are corrected somewhat. When employing the center image 1102f, sometimes the sizes of 1001a and 1001b are corrected. In this way, in addition to the technique of splicing together the protruding parts between images, when not extracting the protruding parts and superposing images as they are at the common parts, sometimes the center images are superposed while adjusting them in size.

By, in this way, combining the left and right rows of teeth from the center images to form left side combined rows of teeth and right side combined rows of teeth and combining these based on their respective center images, it is possible to form a panoramic image of rows of teeth kept down in deviation.

For combination based on the center images, for example, it is preferable to use the contact line (edge) between teeth at the center so as to combine the left side combined rows of teeth and the right side combined rows of teeth. Furthermore, the mark does not necessarily have to be provided at the center teeth. It may sometimes be a portion of a tooth which is captured at a timing when changing the direction of the camera at the time of capture. In addition, the position of the mark is suitably selected based on the objective etc.

The characterizing portion is also not particularly limited so long as a portion which, in the same way as a mark, enables positioning at the time of combining images. Further, by applying a mark to the rows of teeth being captured in advance or providing a portion corresponding to a mark from the images, more accurate combination becomes possible.

Note that, the above explanation of operation is for the case of using graphic software to perform operations on a plurality of images which are displayed on a computer monitor such as copying and pasting them, dragging and dropping them, enlarging or reducing images, or correcting tilt visually and by mouse operation. Sometimes the known automatic panoramic image photo composing software such as Photoshop Elements 7® (made by Adobe), Photo Stitch® (made by Canon), etc. may be utilized.

[Preparation of 3D Panoramic Tooth Row Image]

A row of teeth is shaped bent into a bow in the bite plane. When trying to obtain a realistic grasp of it as a whole, with a 2D panoramic image display, the state of the individual teeth can be understood, but since the teeth are displayed in a state arranged in a flat shape, they are insufficiently grasped in three dimensions. Therefore, a technique able to display them in three dimensions is preferable.

The technique for obtaining a panoramic image by the actual image of an oral cavity, as described in for example WO2007/063980, is to form a frame which has a shape approximating an imaginary curve resembling the outline of an arch form of a row of teeth, arrange the camera device at its side surface, capture the rows of teeth as a whole, and convert the result to a 3D format so as to obtain a 3D panoramic image. True, it is possible to capture an image of rows of teeth in a 3D state, but it is hard to say this is a simple measurement technique due to the need for forming a frame provided with an imaginary curve resembling the outline of an arch form.

Figure 13:
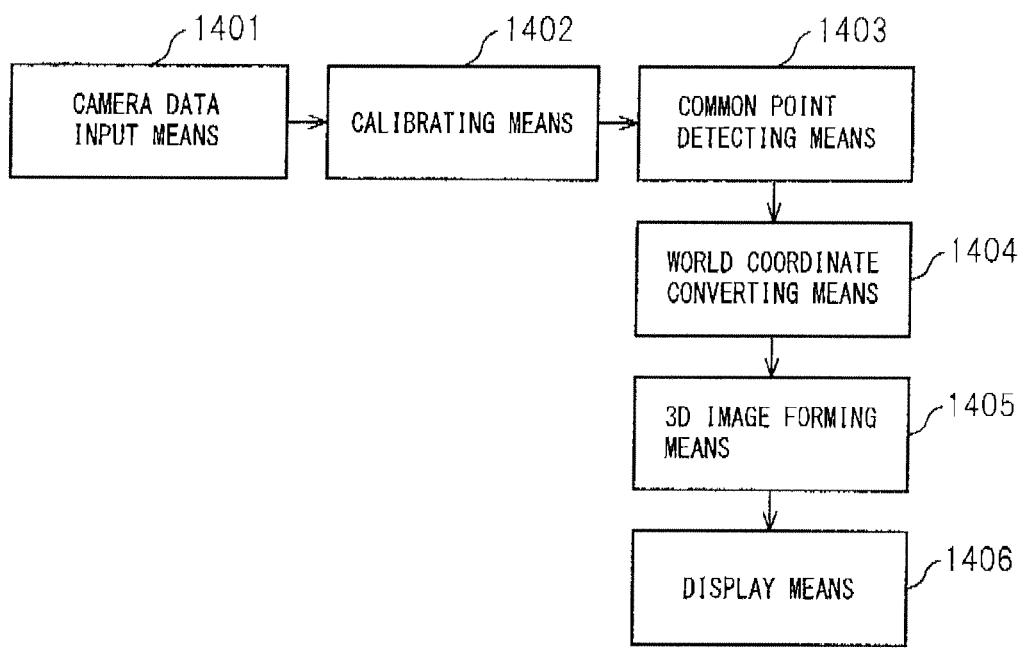
FIG. 13 is a block diagram for showing another embodiment of the present invention.

Next, an example of forming a 3D panoramic image by actual images will be explained with reference to FIG. 13. FIG. 13 is a block diagram for explaining a 3D panoramic tooth row image forming means.

Reference numeral 1401 indicates a camera data input means. This connects a stereo image capturing camera which is provided with a plurality of cameras such as shown in FIG. 14 and simultaneously forms the seine number of images as the number of cameras.

The camera data inputting means 1401 is of a type where the shutter is operated for each image or a type where the shutter is operated once to enable continuous capture of a plurality of photographs. Sometimes a plurality of pairs of still images are continuously output.

Reference numeral 1402 indicates a calibrating means. This corrects distortion due to the lens shape, handshaking, etc. and corrects the perspective distance etc. It is configured using the known technique of calibration.

The calibrating means 1402 calibrates the simultaneously captured images and deletes the peripheral parts where distortion is large.

Reference numeral 1403 indicates a common point detecting means. This for example detects common points of a pair of images. The common point detecting means 1403 uses the luminance of one pixel or one group of pixels of one image as the reference luminance, uses the luminance of one pixel or one group of pixels of the other image to obtain, for example, the sum of absolute difference (SAD) of luminance and the sum of squared difference (SSD) of luminance, and outputs the parts which match by the minimum values or maximum values or the parts estimated by subpixel estimation as common points.

More specifically, for example, it is possible to utilize the configuration shown by Motoki Arai at al., *Optimization of Correlation Functions and Subpixel Designation Formula in Block Matching of Images*, Research Reports of Information Processing Society of Japan, 2004, P 33-40 and other known techniques.

Reference numeral 1404 indicates a world coordinate converting means. This converts the coordinates of images of the common points obtained to 3D coordinates common to them all.

The world coordinate converting means 1404, for example, performs computer processing by the triangle method, 8-point algorithm method, triangulation method, or other arithmetic technique. It forms and outputs parallax values from coordinate values of photographic images of common points obtained by the common point detecting means 1403 and world coordinates (X, Y, Z) from characteristics of the camera (internal parameters of focal distance of lens, image center, and pixel size and external parameters of positions and postures of two cameras).

For example, the world coordinates (X, Y, Z) are found based on the generally known following formula (1) from the perspective projection matrixes P1 and P2 comprised of the internal parameters and external parameters of the different cameras and the local coordinates (u1, v1) and (u2, v2) of the common points M of the captured images:

$$\omega_i \begin{bmatrix} u_i \\ v_i \\ 1 \end{bmatrix} = P_i \begin{bmatrix} X \\ Y \\ Z \\ 1 \end{bmatrix} (i = 1, 2) \quad (1)$$

For the method of using the internal parameters and external parameters of the cameras to find perspective projection matrixes or finding the perspective projection matrixes $P_1$, $P_2$ and $\omega 1$, $\omega 2$ from the local coordinates of a plurality of common points obtained from still images and obtaining world coordinates based on the above formula (1), for example, the technique described in the Journal of the IEICE, Vol. 92, No. 6, 2009, 463-468 and other known techniques may be suitably used.

Another technique for obtaining 3D coordinates is described together with the closeup technique in, for example, *Dental Materials and Equipment*, Vol. 19, No. 3, 333-338 (2000) etc., but the invention is not limited to this. Other general techniques can be employed.

Reference numeral 1405 indicates a 3D image forming means which, for example, can display this world coordinate data in a 3D coordinate space virtually formed on a computer and connect this coordinate data by lines or curves to form a wire frame model and which, furthermore, can attach virtual surface data to parts surrounded by the lines so as to obtain more realistic panoramic 3D data. By making the 3D panoramic tooth row data three-dimensional on 3D coordinates, curved rows of teeth can be displayed.

Reference numeral 1406 indicates a display means which may be formed by a computer monitor, printer, etc. and may display a virtual 3D image on a usual computer monitor. Furthermore, it may display a curved panoramic tooth row image by projection to two dimensions.

FIG. 14 shows one example of a probe-shaped 3D measurement probe 1500 which is provided with two cameras at its tip end. Reference numeral 1501 indicates a camera part A. This has a lens 1501*a* at its center and has the form of a so-called "camera module". Reference numeral 1502 indicates a camera part B. This has a lens 1503*a* at its center and has the form of a so-called "camera module".

Reference numeral 1503 indicates a lighting beam emitter. This is preferably provided around the camera part A1501 and the camera part B1502. Light which is emitted by the light emitting means 1505 which is formed inside of the support member 1506 is guided through the light guide 1504 and fired from the lighting beam emitter 1503 to the surface of the tooth being captured. The lighting beam emitter 1503 is preferably shaped so that more uniform lighting is performed. It is not specified as being the shape which is shown in FIG. 14.

Reference numeral 1503*a* indicates a light source for instruction use and shows the captured surface. It provides output in a spotlight like manner. Red, blue, white, and other LEDs covered around them by a black tube are used. Since the light is of a spotlight nature, the area of the surface struck will differ depending on the distance. Therefore, the probe 1500 can be moved while maintaining this constant.

Reference numeral 1504 indicates a light guide which is formed inside of the support member 1506 and is preferably covered at its surface by a light reflecting member made of aluminum, silver, or other thin film. The light guide 1504 is connected with a lighting beam emitter 1503.

Reference numeral 1505 indicates a light emitting means which is attached inside of the support member 1506. A white LED or other light source may be illustrated. In the present embodiment, an intermittent flash drive like a strobe or continuous illumination drive etc. may also be used.

Reference numeral 1506 indicates a support member which, for example, is molded from a light weight, hard plastic material, has a camera part etc. at its front end, is rod shaped, and has a shape enabling it to be easily inserted to the back of the oral cavity.

Reference numeral 1507 indicates an operating switch which performs a shutter operation etc. The switches may be freely set in number in accordance with the operating specifications and objectives and may be configured in any way. A specification may also be employed where, when used as a shutter, the shutter is driven continuously at predetermined intervals while pressed.

Reference numeral 1508 indicates a holding part which is preferably configured integrally with the support member 1506 and is molded by a light weight, tough plastic material.

Reference numeral 1509 indicates an electric lead line which is connected to an outside power supply and connects with an outside data processing system etc. A cable utilizing a USB connector may be utilized. Note that, when the light source is a strobe-type light emitter and the continuous shooting data can be temporarily stored inside of the camera, if Zigbee® wireless communication front end circuit is used for wireless connection etc., sometimes a connecting means becomes unnecessary.

Next, the operation of the present embodiment which is shown in FIG. 13 and FIG. 14 will be explained.

In the camera data inputting means 1401 of FIG. 13, the user holds the holding part 1508 shown in FIG. 14 and, in the state such as shown in FIG. 8 where the upper and lower teeth are engaged with each other, brings the camera part A1501 and the camera part B1502 at the front end of the support member 1506 close to the captured portion, and, while viewing the size and position of the spotlight emitted by the instruction use light source 1503*a*, presses the operating switch 1507 to start the continuous capture operation.

Sometimes rather than a continuous capture operation, it is better to press the shutter use operating switch 1507 for every capture operation, but to prevent hand shaking etc., continuous capture where the number of times the switch is depressed is reduced is preferable. In this pressed state, images are captured up to the same position as in FIG. 8A, then images are captured up to the same position in the same state as FIG. 10A.

FIG. 15 shows images forming pairs in the group of images which were obtained by a single continuous image capture operation. Note that, when more precisely measuring the surface shapes of the teeth in the oral cavity, it is preferable to capture the images in the proximity state. The focal distance of the camera is also preferably set at a state which enables close-up photography. These captured images are calibrated against distortion due to the curvature of the lens, tilt, etc. by the calibrating means 1402 of FIG. 13 and are output to the common point detecting means 1403.

At the time of 3D processing, as shown in FIG. 9 and FIG. 11, the combination is preferably performed from the center in consideration of the combination from near the center to the left-right direction, but the invention is not particularly limited to this technique.

Figure 15A:
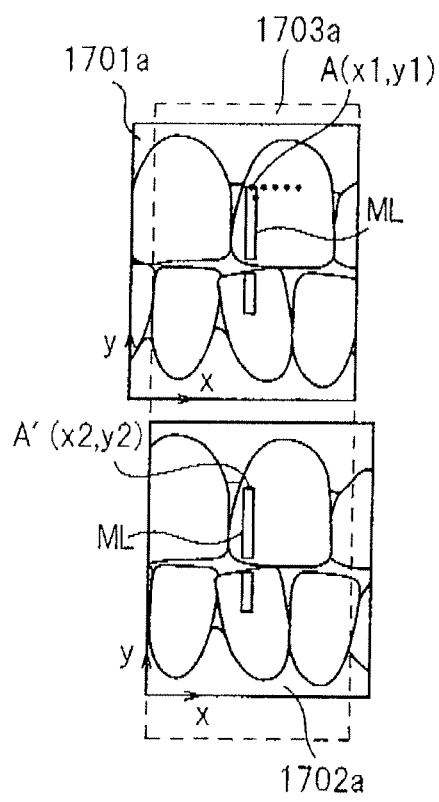
FIG. 15 is a schematic view for explaining an embodiment.

FIG. 15A is a front view of teeth and shows an image capturing a location near the center. This is also data which is obtained by capture by the camera data inputting means 1401 which has the probe 1500 of FIG. 14 as a constituent requirement.

Reference numeral 1701*a* indicates the image of the camera part B1502, while 1701*b* indicates the image of the camera part A1501. These images are assigned coordinates having center points of the same part. For example, any point A (x1, y1) of the image 1701*a* of FIG. 15A captured by the camera part B1502 is set and the point A' (x2, y2) showing the same position as this is searched for. The average luminance is found using the point A as for example one pixel block. From near the position envisioned as the point A' of the image data 1702*a* of FIG. 15A, a pixel block of the same size as the point A is found. The sum of the difference of luminance of the two or the squared sum is obtained and gradually similar operations are performed in the direction of the point A' along with movement to form a match evaluation curve.

The subpixel estimation technique which sets the part where the sum of the differences or the squared sum of the differences becomes the smallest or becomes the largest on the match evaluation curve as the point A' is preferable, but the invention is not particularly limited to this so long as a technique obtaining common points.

Next, a similar operation is performed on the pixel block next to the point A of 1701*a* to detect the common points from the image 1702*a*. This operation is performed repeatedly to find the coordinates of common points in the common range 1703*a* minus the range of occlusion of the images 1701*a* and 1702*a*. In this case as well, formation of common point coordinates centered at the position of the newly added mark ML enables high precision common points to be obtained. Further, by making this block smaller, common points can be detected in a state of a high precision, but the processing time becomes long, so the size of the block etc. are suitably selected.

Next, the world coordinate converting means 1404 of FIG. 13 converts, for example, the coordinate values measured by taking several of the above-mentioned common points to a 3D word coordinate system based on the parallax, focal distance, and other parameters inherent to the camera and formula 1. For this specific technique, the usual methods shown in the above-mentioned literature etc. may be suitably employed.

Figure 15B:
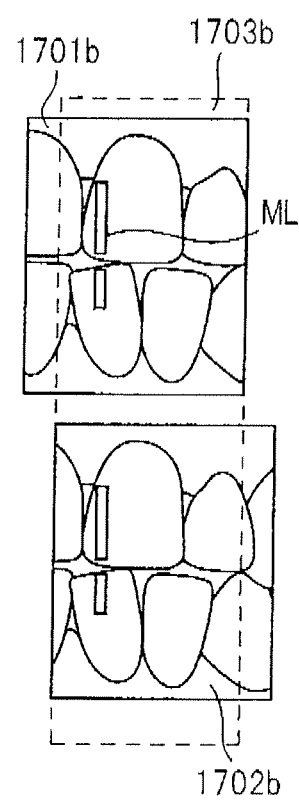

It finds the common points from a pair of images of FIG. 15A, then uses the image pair 1701*b* and 1702*b* shown in the next FIG. 15B to convert the common range 1703*b* minus the range of occlusion to 3D world coordinates A (X, Y, Z). In the state of 3D world coordinates, it prepares, for example, an image formed into the wire frame shown in FIG. 15D.

Furthermore, it finds the 3D world coordinates of common points of the common range 1703*c* minus the range of occlusion of the image pair 1701*c* and 1702*c* shown in FIG. 150.

Next, the 3D image forming means 1405 which is shown in FIG. 13 superposes the 3D coordinates which were converted to world coordinates and found from FIG. 15A with FIG. 15B not by planar superposition, but in a virtual 3D coordinate space. It further superposes the 3D world coordinates shown in FIG. 15C with this superposed image. If this superposition is superposition in a virtual 3D space, it is possible to use the data converted to 3D world coordinates as the basis to virtually display wire frame like rows of teeth such as for example shown in FIG. 15D on a computer monitor and possible to try to superpose them visually while operating a mouse or other computer interface, but to raise the precision of the superposition, sometimes it is preferable to use either of the 3D values for comparison as a reference and use differential comparison etc. so that the difference becomes the smallest in the combination. The subpixel estimation technique using block matching may also be used to obtain common points.

Figure 15C:
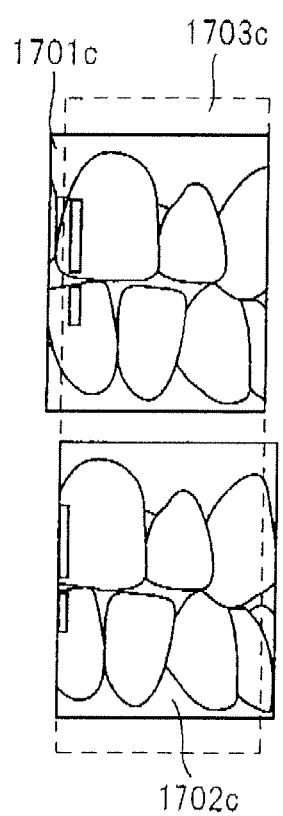
Figure 15D:
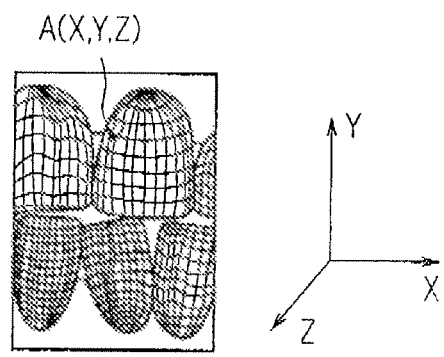

FIG. 15A to FIG. 15C show the formation of rows of teeth based on data obtained by converting the right side rows of teeth to 3D world coordinates toward the front surface, but next the left side rows of teeth are converted to 3D world coordinates. The conversion to world coordinates may be performed using the above-mentioned known technique. For example, it is possible to obtain 3D coordinates based on the two images, the convert them to common coordinates, that is, world coordinates.

After obtaining the 3D world coordinates of the left and right rows of teeth, it is sometimes sufficient to combine the rows by 3D virtual display on a computer or by approximate match by numerical superposition of the coordinate values. In this case, it is preferable to superpose them based on the 3D coordinate data of the mark part. According to this technique, not only with 2D, but also with 3D coordinates, panoramic display of the rows of teeth without offset becomes possible by the display means 1406 shown in FIG. 13.

The superposition is performed by the technique of superposing numerical values of data of the same shape parts and, when they do not match, taking the average of two coordinate values while performing superposition, the method of superposing images on the screen by the manual technique of dragging and dropping them while operating the computer mouse, then finding the coordinate values, etc.

Note that, even if images which have mutually common portions, if images with poor degrees of superposition due to the image capture circumstances even after calibration, it is sometimes sufficient to select one of the common images. Sometimes it is possible to use the image of the not superposed part as required for preparing the panoramic image.

By combination by conversion to three dimensions based on world coordinates, it becomes possible for the entire rows of teeth to be displayed in a so-called "denture" state.

A 2D display of a panoramic digital image of the side surfaces of the teeth and a 3D display of a panoramic digital image of the side surfaces of the teeth enable a patient to easily understand the state of his or her entire rows of teeth, so, for example, the 2D panoramic image tooth row data and 3D panoramic image tooth row data may respectively be processed for simulation of straightening and virtual whitening to as to form virtual rows of teeth. The image of this state may be displayed together on the computer monitor to form a state impressing upon the patient the effect of treatment etc.

"Simulation of straightening" indicates for example, in the case of a 2D panoramic tooth row image, preparing a database of various shapes of single teeth in advance in accordance with the portion, processing the images of the teeth on the 2D panoramic tooth row image by having an orthodontist operate a computer mouse in graphic software to copy and paste images, and thereby forming a virtual straightened panoramic image of the rows of teeth.

In the case of a panoramic 3D tooth row image, since the 3D coordinates have already been set, existing CAD software may be used by an orthodontist etc. to adjust the 3D coordinates of the panoramic 3D tooth row image so as to form a virtual straightened 3D panoramic image of the rows of teeth. The technique of displaying such a straightened panoramic image is an illustration. Other techniques may also be employed.

A virtual display after virtual whitening of one's own panoramic 2D and 3D tooth row images or display of these images after being adjusted in color by the dentist in graphic software are also possible alongside. By providing a display of a panoramic image of a patient's own rows of teeth after treatment for virtual straightening and virtual coloring in this way alongside on the screen, it is possible to increase the depth of the patient's understanding of treatment.

[Means for Firing Sighting Beam]

FIG. 16 is a view which shows one embodiment of the present invention. In the figure, A10 indicates a reflecting mirror unit. This is formed by a hard plastic etc. At the front end, a reflecting mirror A10K set at a predetermined angle (for example 45 degrees) is provided. At the back end, a tubular mounting part A10S able to be connected to the outer circumference of the camera unit A14 is formed. The shape between them is opened.

The mounting part A10S and the camera unit A14 are connected by being shaped to allow one to be pushed into the other. They can be detached by just pulling them apart as well. To prevent rotation, the two may be provided with relief shapes or may be formed in elliptical shapes or other asymmetric shapes.

A11 indicates a housing. This is formed by a plastic or resin and is shaped as a tube like a ball pen which has a large caliber and is easy to grip by the hand. At the front end, the camera unit A14 is arranged sticking out. At the back end, a cable A15 for connection with an outside processing system is connected.

A12 is the direction of observation when a dentist, dental hygienist, etc. directly views the reflecting mirror A10K which is arranged at the front end of the reflecting mirror unit A10 at a predetermined angle.

A13 indicates a surface struck by the sighting beam. This is one example of the surface struck by the sighting beam when the sighting beam which is output from the sighting use light source A142 is reflected at the reflecting mirror A10K and strikes the tooth surface.

The sighting use light source A142 (see FIG. 16O) may be positioned at any location. So long as a position enabling the range of the captured image to be determined, it may be another position as well. That portion may be, for example, the front end of the reflecting mirror unit A10 at a portion lighting up the image capture range. In this case, the light path becomes short, so sometimes even if the directional angle is somewhat wide, the range of the captured image can be lighted up.

Figure 16A:
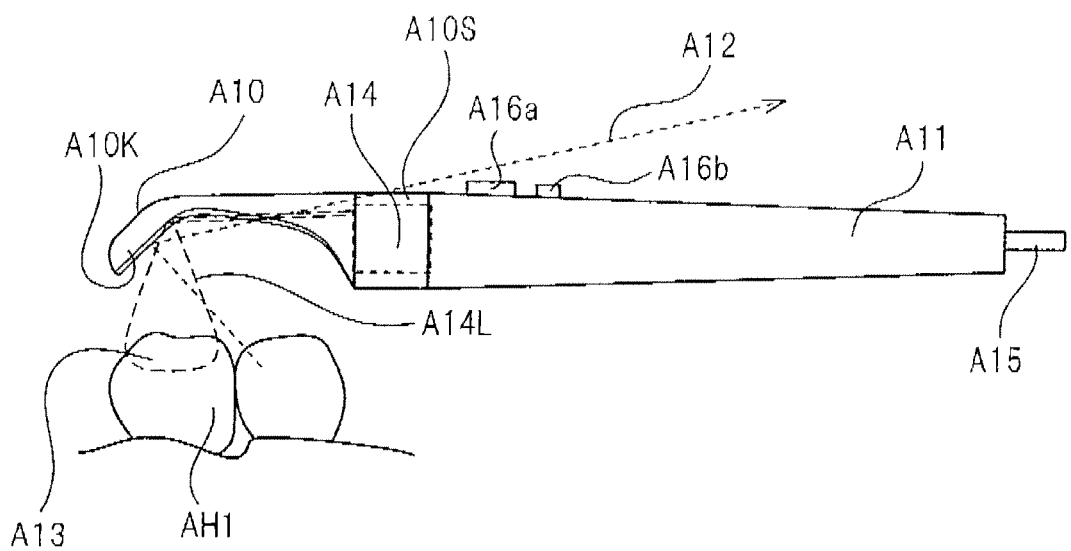
FIG. 16 is a schematic view for explaining an embodiment.
Figure 16B:
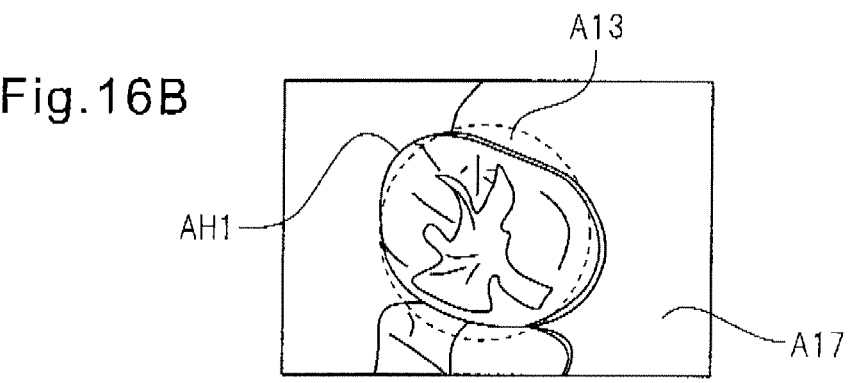
Figure 16C:
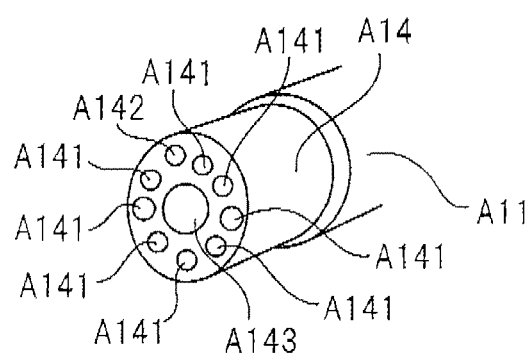

FIG. 16C shows the state of the camera unit A14 enlarged. In the figure, A141 is the illumination use light source. An LED with a wide directional angle or a combination of a lens and an LED may be illustrated as an example. A plurality of illumination use light sources A141 are arranged in the vicinity of the camera member A143.

A142 indicates a sighting use light source. An LED with a small directional angle or a combination of a lens and an LED may be used to output light to give a predetermined spread on the illuminated surface as an example. Alternatively, in the case of a light source with a small directional angle, arrangement of a plurality at predetermined intervals is preferable.

A143 indicates a camera member. This is formed by a CCD or CMOS camera. One with a larger number of pixels is preferable.

Returning again to FIG. 16A, A15 indicates a cable for connection with an external image display device. It may be formed by a general use cable such as a USB cable or also by a dedicated cable.

A16a and A16b respectively indicate operating buttons A and B. These are configured by push types, pull types, turn types, etc. If pushing the operating button A16a among these buttons, the sighting use light source A142 emits light for a predetermined time and lights up important parts for exactly a certain time through the reflecting mirror A10K. The "certain time" is at least the time by which the user can recognize the sighting beam as it strikes a key part in the oral cavity and is preferably until the timing of image capture, for example, when the operating button A16a is pressed.

At the time of image capture, a lighted part with a different color arrangement is formed in the still image. This is not preferable from the viewpoint of obstructing observation. If not obstructing observation, there is no particular need to erase the sighting beam. This may also be turned on and off to draw the attention of the user.

Next, the operation of the embodiment which is shown in FIG. 16 will be explained.

The light output of the illumination use light source A141 which is attached around the camera member A143 of the camera unit A14 lights up the tooth AH1 of the oral cavity through the reflecting mirror A10K. MAL is the light path of the sighting beam. In addition, the illumination use light source also emits light through the reflecting mirror A10K. In this state, the surface A13 struck by the sighting beam is formed in part of the surface which is lighted up.

The camera member A143 captures the portion of the oral cavity which is lighted up through the reflecting mirror A10K and displays it through the cable A15 at an external monitor device.

The dentist or other user can obtain a grasp of the image capturing position by the image which is displayed on an external monitor device, but when shortening the diagnosis and treatment time, when treatment is included, etc., this is often used in the same way as a dental mirror. Sometimes the observation direction differs from the captured image such as shown by A12. At this time, for example, the operating button A16a is pressed. If the operating button A16a is pressed, the sighting use light source A142 emits light. The light is emitted for a predetermined time, preferably until before starting to capture the image, and is of an extent enabling the observer to confirm the observed position and image capturing position. The observer moves the reflecting mirror A10K to match the capture position and the observation position and again presses the operating button A16a so as to adjust the capture position and the observation position.

When the positioning ends, the operating button A16a or operating button B16b is depressed again to record the still image or moving image. The contents of the operations of the above-mentioned operating button A16a and operating button B16b are illustrations and are suitably selected according to the case. One example is shown in FIG. 16B.

A17 indicates an example of an image. A tooth AH1 targeted for capture is captured. The range of firing of the sighting beam is the range of the circle shown by the surface A13 struck by the sighting beam. Almost the entirety of the key part targeted for capture is included.

The range of the surface A13 struck by the sighting beam changes depending on movement of the combination of the housing A11 and reflecting mirror unit A10 up and down with respect to the tooth H1, so the user may adjust this by moving the housing A11 and reflecting mirror unit A10 up and down. The surface becomes larger than or smaller than the image capture range, but never becomes offset from the key part of the image capture range. Further, the key part of the image capture range is sufficiently shown compared with a point light source.

Due to the above operation, the captured surface and the observed surface are adjusted and an accurate still image or moving image is recorded.

The housing A11 which is shown in FIG. 16A is held and the reflecting mirror A10K is made to move up and down with respect to the observed portion of the oral cavity so as to observe and capture the target portion.

The intraoral camera is inserted to the narrow back portion of the upper jaw or lower jaw of the oral cavity. The image capture range of the reflecting mirror extends over a wide range. At the same time, the oral cavity can be captured with the reflecting mirror in the inverted state. Capture is also possible in the tilted state or laid flat state etc. Therefore, the captured image also becomes tilted or inverted. Accordingly, the present invention is provided with an image correcting means for detecting the image capture state by position sensors and correcting images in an up-down inverted state or tilted state to a horizontal state.

[Means for Correcting Captured Image]

Figure 17:
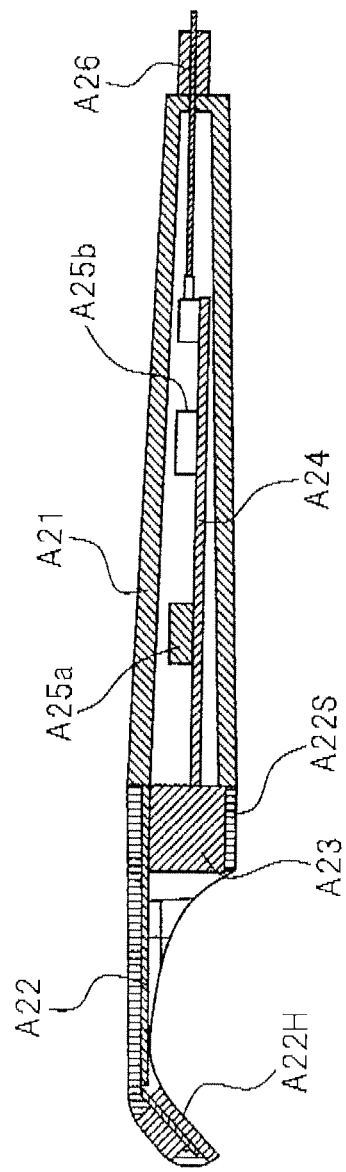
FIG. 17 is a schematic view for explaining an embodiment.

FIG. 17 shows an example of an intraoral camera which is used for explaining one embodiment of the present invention. It is shown as a partial cross-sectional view. In the figure, A21 indicates a housing for holding use. This has a cylindrical shape which is provided with an internal space. At the front end, an elliptical tubular shaped camera unit A23 which is comprised of a camera and illumination use light sources formed around the camera is connected in a state sticking out from the housing A21. At the back end, a cable A26 for connection with an external display device is connected.

One example of the illumination unit is shown in FIG. 17. In the figure, A22 indicates a reflecting mirror unit. At its front end, a reflecting mirror A22H which is arranged at a predetermined angle is attached. At the back end, a tubular mounting part A22S which can be attached to cover the circumference of the camera unit A23 is formed. The ret is open in state.

A24 indicates a circuit board. This is mounted inside of the housing A21 and mounts an image processing use IC etc. A25a and A25b indicate position sensors. These have IC chips etc. which are mounted on the circuit board. The numbers and mounting portions of the position sensors are examples. Depending on the types of the sensors, they are sometimes not mounted.

Figure 19:
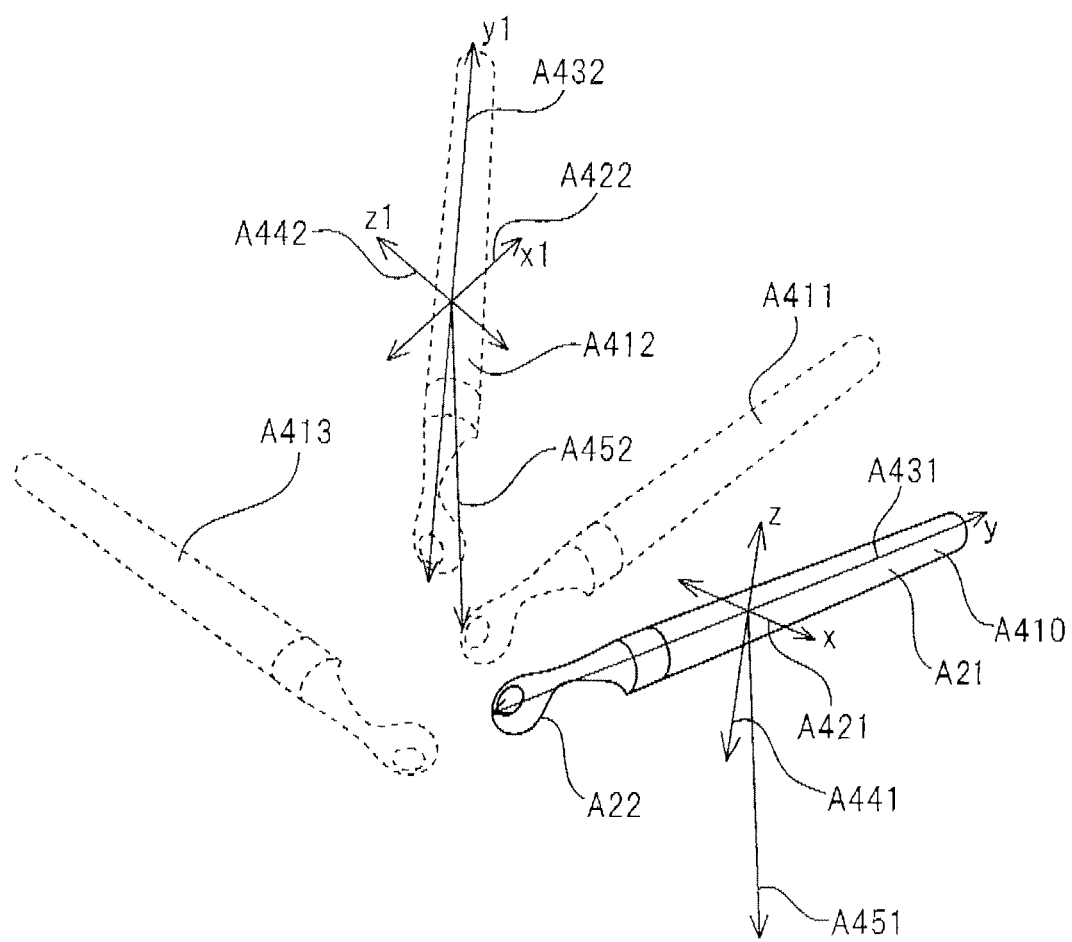
FIG. 19 is a schematic view for explaining an embodiment of the present invention.

The position sensors A25a and A25b employed are acceleration sensors, angular acceleration sensors, or other sensor devices which can sense the state of movement of the intraoral camera over a wide range and therefore will not be disabled from measurement due to the angle. The number of the position sensors is shown here as two, but this is an illustration. The number of chips changes depending on the number of axes. If a unit for three axes, sometimes a single one is sufficient. The acceleration sensors and angular acceleration sensors are illustrated as three-axis sensors. The number of the position sensors also may be adjusted by the number of axes. The x-axis, y-axis, and z-axis of the position sensors A25a, A25b . . . are for example the axes which are shown in FIG. 19.

When the position sensors A25a and A25b are made angular acceleration sensors (gyro sensors), the angular acceleration sensors, for example, respectively output the amount of change of the angle due to movement about the x-axis, the amount of change of the angle due to movement about the y-axis, and the amount of change of the angle due to movement about the z-axis. In the case of angular acceleration sensors, the initial states of the x-axis, y-axis, and z-axis are freely set, then the amounts of change along these axes are added to thereby detect the image capture state of the camera.

As opposed to this, the acceleration sensors respectively output the x-axis direction acceleration component, y-axis direction acceleration component, and z-axis direction acceleration component. Furthermore, the combined vector of these acceleration components gives a posture vector. In the still state, the respective gravity acceleration vectors are shown. The image capturing state of the camera can be obtained from this posture vector.

For example, an acceleration sensor outputs the state of the gravity acceleration vector A451 as the posture vector when still, so it is possible to use the x-axis direction, y-axis direction, and z-axis direction vectors in this state as the reference posture and then use the angular acceleration sensors to add the amounts of change by rotation of these axes and perform other operations, so it is also possible to combine both acceleration sensors and, angular acceleration sensors to detect various states of a camera.

Figure 18:
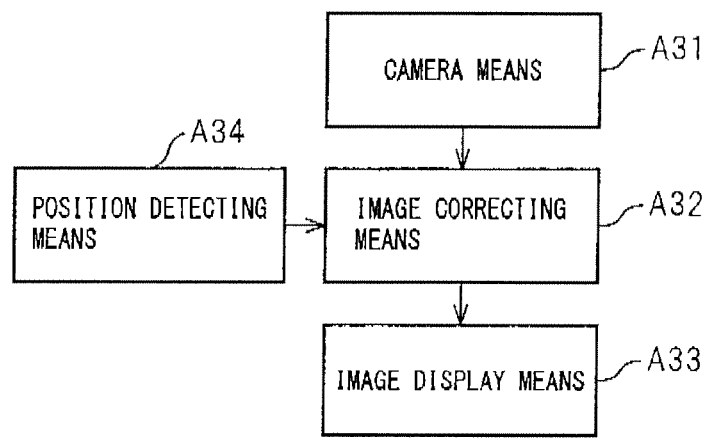
FIG. 18 is a block diagram for showing an embodiment of the present invention.

FIG. 18 is a block diagram which shows an example of means for using position sensors to correct the image display state. The configuration which is shown by the block diagram may have parts which are realizable by a program if involving computer processing. In the figure, A31 indicates a camera means which uses a camera which is arranged at the center of the camera unit A23 of FIG. 17 to capture a moving image or still image.

A32 indicates an image correcting means which is comprised of an image recording memory, CPU, etc. It temporarily records an image which is obtained by the camera means A31 and uses the camera angle information of the position detecting means A34 as the basis to rotate the image and form image data in a state which can be easily viewed.

For example, when the camera unit A23 captures an image, the reference posture of the image displayed on the monitor is determined, the housing is moved with respect to that reference posture, and thereby the reference posture image rotates, for example, the angular acceleration sensors etc. detect the amounts of change of the rotational angles from the angular accelerations of the respective axes to enable display of the images rotated by exactly the angles minus the amounts of change of the rotational angles whereby an easily viewable image can be formed.

Note that, sometimes the image can be corrected by just rotation about the y-axis which is shown in FIG. 19. When capturing an image of the oral cavity which is reflected by the reflecting mirror, since the camera of the camera unit A23 is constantly facing the reflecting mirror direction, the image rotates mainly due to rotation accompanying rotation of the housing about the y-axis coordinate shown in FIG. 19. Therefore, at the very least, in the state where the housing A11 and reflecting mirror unit A10 are changed in the x-axis, y-axis, and z-axis directions, it is sometimes preferable that the image which is displayed at the xz plane be corrected to a state facing a certain direction at the image display unit.

Reference numeral 33 indicates an image display means. This shows a computer monitor or other dedicated monitor. It is sufficient that it be one which displays the output image of the image correcting means A32.

Reference numeral 34 indicates a position detecting means. This is comprised of the position sensors A25a, A25b, etc. of FIG. 17. Specifically, rate gyros which output angular acceleration, rate integrating gyros which, output angle, posture gyros, MEMS type and other mechanical type, optical type, and other angular acceleration sensors, piezoresistance type, electrostatic capacity type, and heat sensing type MEMS sensors, and other acceleration sensors can be utilized.

Next, the operation of FIG. 18 will be explained with reference to FIG. 17 and FIG. 19.

The coordinate axes which are shown in FIG. 19 indicate the case where a single position sensor deals with three axes. When the position sensors respectively deal with single axes, two axes, etc., coordinate axes are set corresponding to the individual portions of the position sensors.

The housing A21 which is shown in FIG. 17 is held and the reflecting mirror A22H is inserted into the oral cavity to capture an image of the target portion. At this time, a switch which is attached on the housing A21 is operated to record the initial posture state. One example of the coordinates at the initial posture state is shown by A410 of FIG. 19.

By installing the position sensors, coordinate axes are formed. In the present embodiment, A421 is designated as the x-axis, A431 as the y-axis, and A441 as the z-axis. Note that, AA51 indicates a gravity acceleration vector. This is one example of a posture vector obtained by combination when the acceleration sensor is stationary. Therefore, the gravity acceleration vector sometimes cannot be utilized when not using an acceleration sensor.

The coordinates are shown in a state where the intraoral camera is in a state close to vertical for capturing the side surfaces of for example the back teeth. A422 is the x-axis, A432 is the y-axis, and A442 is the z-axis. When using an acceleration sensor, A452 can indicate a gravity acceleration vector.

The reflecting mirror 22H is made to move the target portion of the oral cavity. One example of the method of movement is shown in FIG. 19. The intraoral camera which is comprised of the reflecting mirror 22H and the housing is moved to the positions such as shown by A411, A412, and A413. The camera means A31 captures the intraoral images in those states as still images or moving images and outputs them to the image correcting means A32.

The position detecting means A34, for example, outputs the initial posture information to the image correcting means A32 for the x-, y-, and z-directions. Further, when, as in the present embodiment, configuring the system to display the image of the reflecting mirror, the camera faces the reflecting mirror direction, so the camera image inverts and becomes hard to view in state usually due to rotation about the y-axis, so sometimes it is also possible to use only single-axis type position sensors. The image correcting means A32 links this initial posture information and image for output to and display at the image display means A33.

As shown in FIG. 19, when moving the intraoral camera like A411, A412, and A413 to capture an image of the oral cavity, the camera means A31 outputs images corresponding to those postures. If the camera rotates about the y-axis, the image is captured upside down and an image corresponding to the captured state is output.

The position detecting means A34 detects the angular accelerations about the x-axis, y-axis, and z-axis from the position sensors A25a and A25b (for example in the case of gyro sensors) and detects the amount of change of the angle about the x-axis ($\Delta\theta yz$), the amount of change of the angle about the y-axis ($\Delta\theta xz$), and the amount of change of the angle about the z-axis ($\Delta\theta xy$) from the angular accelerations.

These amounts of change are output to the image correcting means A32. The image correcting means A32 uses the image data which was input from the camera means A31 and the position information which was output from the position detecting means 34 as the basis, for example, uses the amounts of change of the angles as the basis, to make the image rotate and return it to the initial state of the image.

Therefore, in the image display means A33, even if capturing the same intraoral object as a moving image or still images while rotating the camera, images can constantly be displayed as in the initial set state with the images of the displayed content changed.

Note that, when using a convex mirror to capture all teeth of the upper jaw and lower jaw, it is also possible to use the fisheye lens correcting means of the technique described in the Literature (Design Wave Magazine, 2008 December, P 113-115).

[Means for Adjusting Capture Operation Timing]

The present invention adjusts the time until the actual capture operation by the method of pressing the switch which is operated when obtaining an actual image, for example, by the number of times pressed in a certain time like the "double click" performed when operating a computer, and therefore help stabilize camera operation when the dentist performs treatment, performs diagnosis, or provides an explanation to the patient. Alternatively, it is possible to adjust the capture operation timing by operating a camera switch on the monitor image and designating an icon showing the timing of display (for example, for two operations in two seconds and then continuous capture of several images) so as to determine the timing.

Further, when displaying coordinates etc. on the screen, by adjusting the number of times the operating button is depressed, the way it is depressed, etc., it is possible to adjust the timing of the display and therefore provide an explanation while inserting the camera into the oral cavity or otherwise adjust the timing of display of the image. The specifications of the specific timing may be input and adjusted from the screen of a mobile terminal.

One example of the timing adjusting means will be explained in detail with reference to FIG. 20. In FIG. 20, B7001 indicates an inputting means. For example, it shows pushbuttons 101d and 101e forming the operating interface of FIG. 1.

B7002 indicates an input count detecting means. This is comprised of a counter, flipflop, etc. and counts the number of times a pushbutton is depressed. This count is preferably counted within a predetermined time interval.

B7003 indicates a delaying means. This is for setting a delay time by multiplying the number of times the pushbutton is depressed with the delay time for each time. After the elapse of the delay time, a single pulse is output.

B7004 is an image capture output setting means. At the rising and trailing edges of the delay pulse of the delaying means B7003, a signal for starting the capture operation is output to the camera means B7005.

The camera means B7005 uses the signal of the start of capture as the basis to continuously capture several to several dozen still images or capture a moving image. The images obtained by this capture operation are input to the image inputting means B7006. Furthermore, the image selecting means B7007 selects the focused images and stores them at the storage and display means B7008 or displays them on the display 104 shown in FIG. 1.

The image inputting means B7006 is for fetching an image obtained by the camera means B7005 as digital data and outputting it to the image selecting means B7007. Further, the image selecting means B7007 is, for example, a means for selecting only focused images.

B7009 indicates a display means which shows the time from when a button of the inputting means B7001 is pressed to when the operation is performed in a visual manner while changing the position of blinking. The display means B7009 is set at a location highly visible to the dentist at time of treatment and shows how many seconds after the operating button is pressed the operation will be started. It is sometimes displayed on the monitor of a computer constituting one of the display means B7009.

Further, by providing an LED which gives off a red color during the delay time and which changes to a white color when the delay time ends or a light source which continuously emits light or intermittently emits light only during the delay time or other indicator by which the user can discern that the delay time is in progress, relaxed button operation becomes possible and the extent of intraoral work can be expanded.

[Means for Capturing X-Ray Image]

Figure 21A:
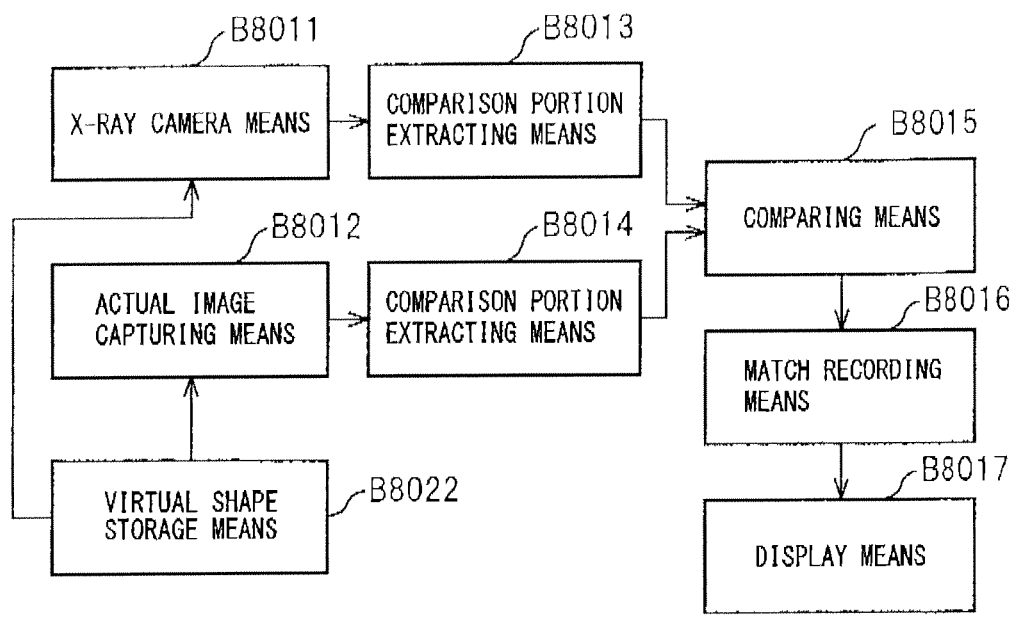
FIG. 21 is a block diagram for explaining an embodiment of the present invention.
Figure 21B:
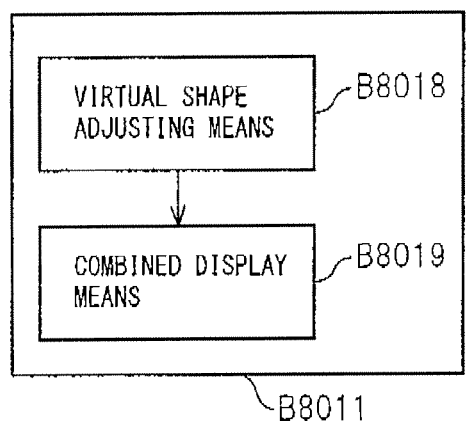

FIG. 21A is a block diagram which shows an embodiment of the present invention. In the figure, B8011 indicates an X-ray image capturing means. A combination of an X-ray output device and an X-ray CCD sensor or a combination of an X-ray output device and X-ray phosphor plate and CMOS or CCD camera are illustrated. Specifically, FIG. 21B shows one example.

The X-ray image capturing means B8011 includes the existing panoramic image X-ray camera device, X-ray CT, digital X-ray device, etc. It is sufficient that it enable data to be displayed on a computer monitor. When X-ray image data cannot be directly obtained, it is also possible to obtain visualized data of the X-ray image on the computer, hard copy data of the screen, data in a shared state on the monitor screen, data obtained by capturing an X-ray image on the monitor by an intraoral camera, or other X-ray image data. Furthermore, sometimes the configuration of FIG. 21B is also included.

Figure 21C:
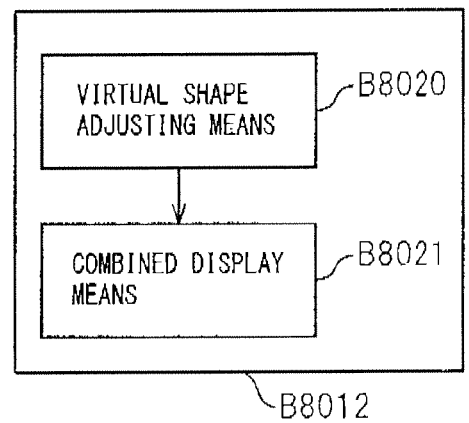

B8012 indicates an actual image capturing means. For example, a reflection type intraoral camera is preferably used. The actual image capturing means B8012 sometimes further includes the configuration which is shown in FIG. 21C.

B8013 is a comparison portion extracting means. It is formed by the block matching technique and subpixel estimation technique and extracts parts matching with the image captured by the X-ray image capturing means B8011 and extracts comparison portions. For example, it extracts contours of the captured image, extracts a plurality of pixel values, and outputs the X-ray image extracted data.

B8014 indicates a comparison portion extracting means. It is formed by the block matching technique, subpixel estimation technique, etc. and extracts parts matching with the image captured by the actual image capturing means B8012 and extracts comparison portions. For example, it extracts contours of the captured image, extracts a plurality of pixel values, and outputs the actual extracted data.

B8015 indicates a comparing means. It compares extracted data which is output from the comparison portion extracting means and outputs portions which match, substantially match, or are estimated as matching as matched parts. At the time of comparison, the images are sometimes enlarged or reduced, but for example the actual image and X-ray image data need only be enlarged or reduced by general use graphic software after conversion to the BM, JPEG, GIF, or other general formats.

B8016 indicates a matched part recording means. This records the matched portions, substantially matched portions, or estimated matched portions and transmits them to the display means B8017.

The display means B8017 may be a computer monitor (display) device, mobile phone display part, etc., but it is sufficient if it be of a size of an extent enabling side-by-side display of an X-ray image and an actual image and superposed display and have a resolution of an extent whereby the X-ray image can be displayed clearly.

The present embodiment is realized by computer software, but may also be formed by hardware.

The X-ray camera means and the actual image capturing means may be separate devices, but preferably they are a single device with parts changed and shared.

Next, the operation of the present embodiment will be explained.

The X-ray camera means B8011 is used to capture a measured portion by a moving image or still images. The portion which is measured by the X-ray camera means B8011 may be selected as a single tooth, a plurality of teeth, or all teeth of the upper jaw and lower jaw.

Next, the actual image capturing means B8012 is used to capture the portion captured by the X-ray camera means B8011 as a moving image or still images. In capture, the same portion may be accurately positioned to for capture, but it may also be used as a general measure for capture.

Distortion of the image obtained from the two is corrected. As the technique for the correction, for example, the calibration technique may be used. A grid serving as a reference is captured in advance to calculate the distortion value due to the lens and to correct the data.

Next, the comparison portion extracting means B8013 and B8014 calculate the characterizing portions. The characterizing portions are, for example, contours. Part or all of the contours of teeth in the case of X-rays and the contours of teeth in the case of actual images are extracted.

Next, the contours of the two are compared. At that time, the X-ray image and the actual image have parts of the contours matched in state or substantially matched in state and the superposed portions of the two images are taken out.

The comparing means B8015 outputs the two superposed images to the matching part recording means B8016, whereupon the matching part recording means B8016 records the two images. The display means B8017 displays the two images in accordance with the selection of the user to superpose them in a transparent state or place them side by side.

FIG. 23 shows one example of images captured by the X-ray image capturing means and the actual image capturing means. FIG. 23A indicates an X-ray image which shows a tooth b101 captured by X-rays. FIG. 23B shows an actual image of a tooth b101 captured at the same portion as FIG. 23A. FIG. 23O shows a superposed image b103 displaying these superposed. The comparison of the X-ray image and the actual image can be used to facilitate understanding of the X-ray image. In particular, the display of the actual image enables the color and any swelling or inflammation of the gums to be displayed, so comparison with the X-ray image enables the degree of advance of any periodontal disease or tooth decay to be displayed in a manner easily understandable by the patient.

Next, a specific example of the X-ray camera means will be shown in FIG. 22 and explained in detail. In FIG. 22, B9101 indicates a housing for gripping use. This is preferably molded from a plastic material etc. containing lead to make it impenetrable to X-rays.

B9102 indicates an X-ray output device. An existing device of a portable type for general dental use is preferable, but the invention is not particularly limited to this. Any X-ray output device which is used in dental diagnosis and treatment can be used if sufficient functionally, but a portable type is effective for home diagnosis and treatment etc. as well and is suitable for use for X-ray images used with actual images. Even if a portable type, use mounted on a stand is possible.

B9103 indicates an electrical lead line. A general use USB cable may be used. In addition, a dedicated cable etc. may be utilized.

B9104 indicates an X-ray phosphor member. One comprised of a glass substrate which is coated with a crystal of a phosphor material such as CsI, CaWO, $Gd_2O_2S:Tb^{3+}$, 549 nm(f-f), and (Zn, Cd)s:Ag is used.

B9105 indicates a member passing visible light. This is formed by a transparent member which contains lead and passes only visible light.

B9106 indicates a camera unit. In this case, this need only be a camera. A higher resolution one is preferably used.

B9107 indicates a support member for X-ray capture. This is formed by a member including lead and impenetrable by X-rays. At the front end, a reflecting mirror B9108, an X-ray phosphor member B9104, etc. are mounted. The other end is formed into an open tubular shape which is inserted over the camera unit B9106 for fastening.

The reflecting mirror B9108 is, for example, formed in a state tilted 45 degrees. It is formed by a flat type mirror. It is for reflecting a visualized image after removing the X-rays and transferring it to the camera unit B9106.

Figure 22A:
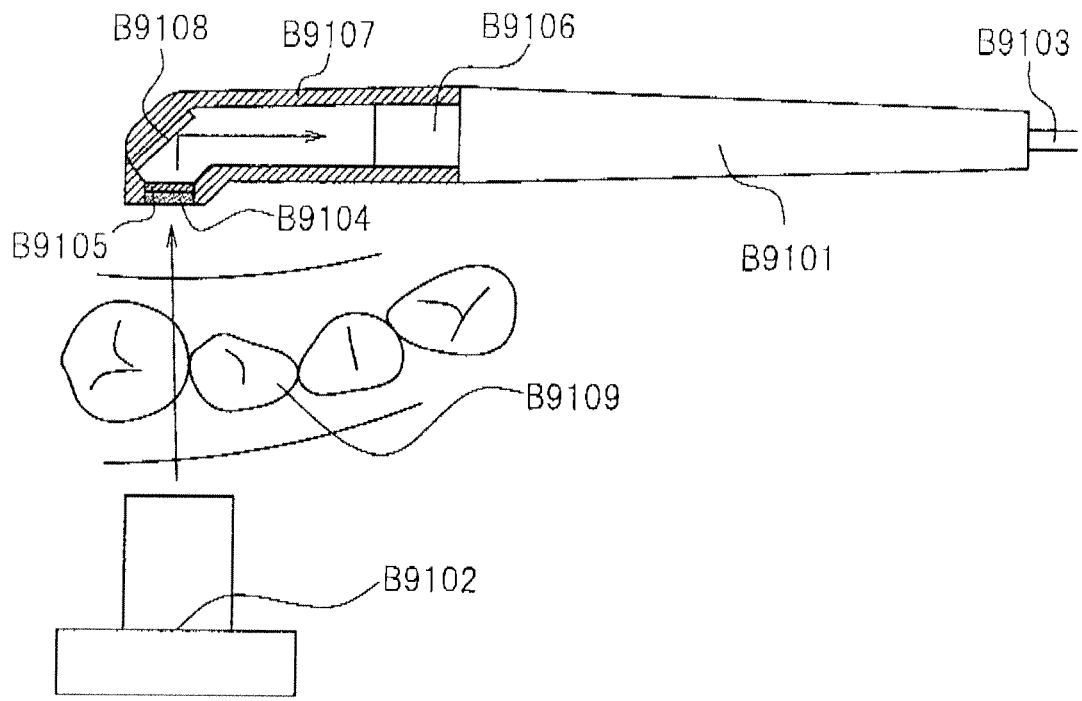
FIG. 22 is a schematic view for explaining an embodiment of the present invention.

In FIG. 22A, the X-rays which are output from the X-ray output device are converted to visible light by the X-ray phosphor member B9104, then the X-ray component is removed, then the light is reflected at the reflecting mirror B9108, then input to the camera unit. B9109 is a schematic view of a row of teeth in the oral cavity at the portion captured.

Figure 22B:
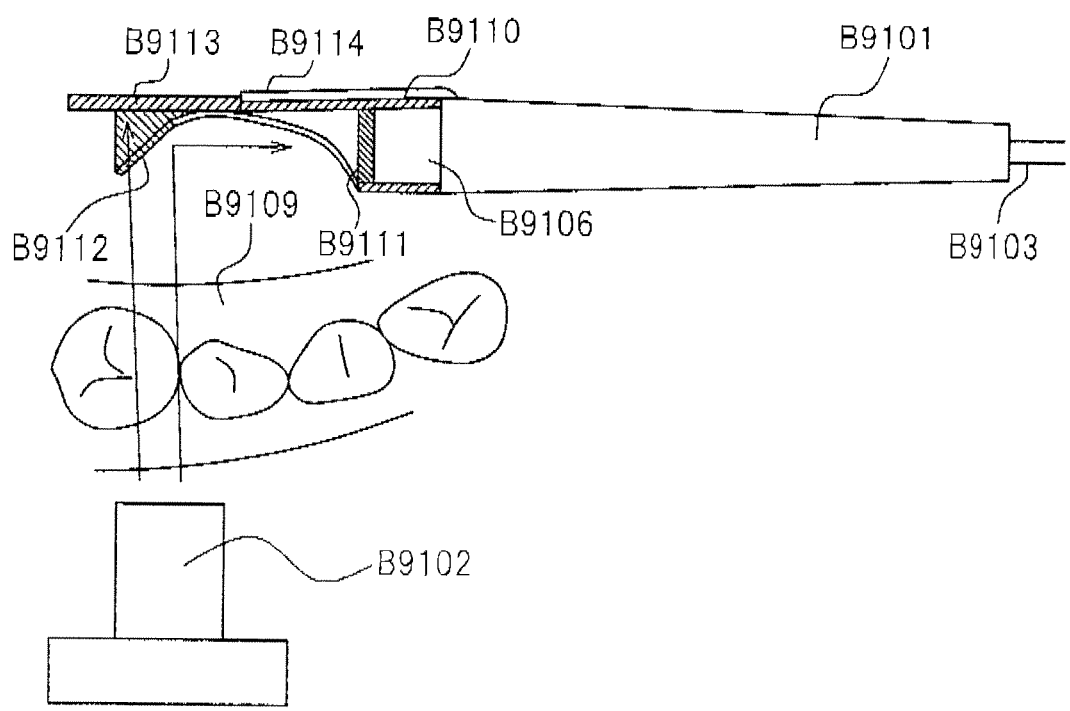

FIG. 22B shows an example of combination of an X-ray photographic image which is obtained by an X-ray sensor and an actual image which is obtained by a reflecting mirror. B9110 is a support member for capturing X-rays and is formed by an X-ray impermeable member in the same way as the support member B9107 for capturing X-rays which is shown in FIG. 2A.

B9111 indicates a visible light passing member which is comprised of a filter which is formed from a light transmitting member containing lead, which removes X-rays, and which transmits the visible light to the camera unit B9106.

B9112 indicates a reflecting mirror comprised of a flat mirror, while B9113 is an X-ray sensor which is formed by an existing X-ray CCD (CMOS) sensor or imaging plate. B9114 is a lead line which transmits a sensor signal of the X-ray sensor to the outside. This is also preferably covered by a resin containing lead.

The present embodiment is configured to use only an X-ray sensor B9113 and also jointly use a combination of a reflecting mirror unit and a camera unit B9106 so as to output an X-ray visible image and an actual image at the same timing.

The configuration combining the reflecting mirror B9112 and the X-ray sensor B9113 enables the actual image to show the back side of the teeth, but comparison against an image separately capturing the front of the teeth becomes easy. The same portion can be simultaneously obtained at the actual image and the X-ray image, so this is preferable from the viewpoint of easy acquisition without image processing for finding the range of match.

An X-ray image of the oral cavity is difficult for a patient to understand, but displaying the actual image of the same captured portion on a computer monitor, paper, etc. side-by-side or superposed transparently enables the X-ray image to be more easily understood and facilitates the explanation to the patient.

In an X-ray image, in the case of a dental X-ray, several teeth, are captured as a single image or single set of data by a single shot. In this case, X-ray sensor and the X-ray output device are shifted while for example continuously capturing images so as to obtain a plurality of X-ray images of the entire jaw, then the contours are extracted as digital data. Further, it is possible to detect the common parts of the images with little distortion at the adjoining X-ray images, detect the points of match and estimated match by the block matching method or superposition, and form a panoramic image. Furthermore, a panoramic image is formed in the same way by the actual images. These images can be displayed on the monitor screen or printed out on paper to form data easy for comparison.

Figure 23A:
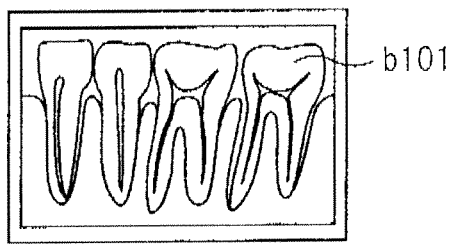
FIG. 23 is a schematic view for explaining an embodiment of the present invention.
Figure 23C:
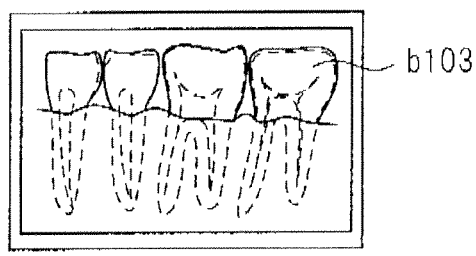
Figure 23B:
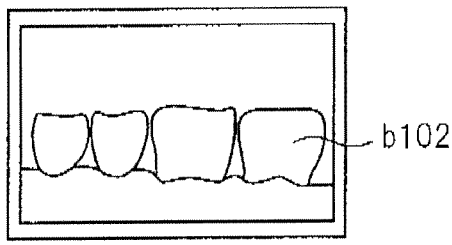
Figure 23D:
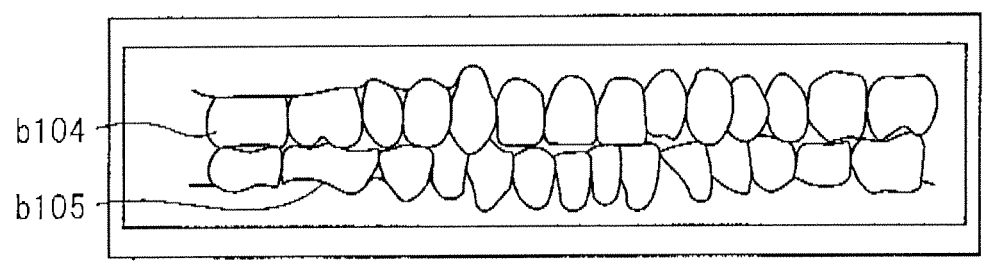
Figure 23E:
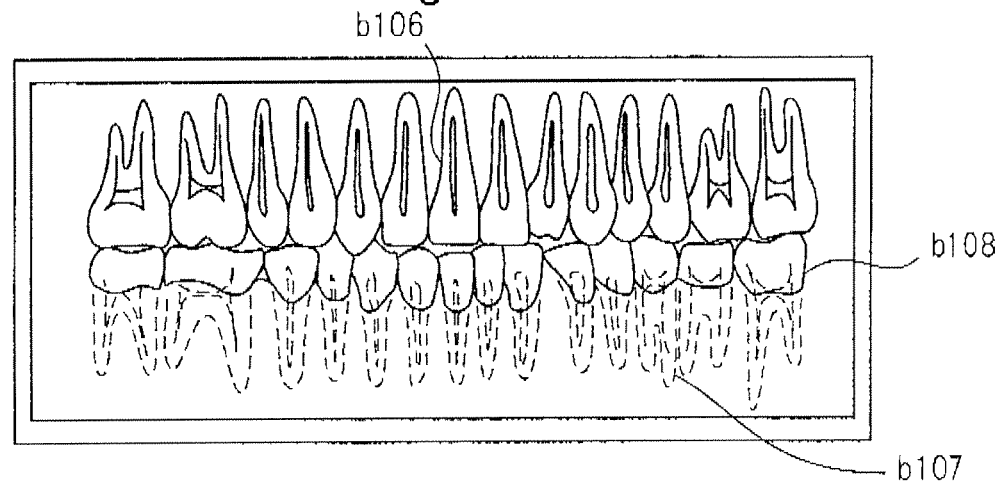

One example of the data is shown in FIG. 23D and FIG. 23E. FIG. 23D shows the state where the actual image data is spliced together by digital processing. b104 is the upper jaw data, while b105 is the lower jaw data. The upper jaw data b104 is obtained, for example, by continuous capture by the intraoral camera which is shown in FIG. 1 while shifting the position bit by bit and splicing together the common parts of the images by superposition. The lower jaw data b105 is also similarly prepared. The method of forming a single image is shown, but it is also possible to simultaneously capture the upper jaw and lower jaw and splice the common parts together by superposition. With continuous capture, the images are displayed continuously. They are also continuous in terms of size. Therefore, it is easy to find the connecting portions. Sometimes, little size adjustment is required.

When obtaining such a panoramic actual image, the intermediate luminance method, block matching method, optical flow method, etc. may be used.

FIG. 23E shows the upper jaw X-ray data b106 and the lower jaw X-ray data b107 which are prepared by splicing together X-ray images in the same way. Furthermore, at the lower jaw, lower jaw data b108 obtained from the actual image is superposed to facilitate viewing by the patient.

The present embodiment enables comparison of the intraoral actual image, X-ray image Y, virtual corrected panoramic tooth row image, virtual colored panoramic tooth row image, etc. by display on a computer monitor or printing on paper Co make the oral cavity "visible" to the patient and therefore promote on-going treatment, effective preventive care, and proactive treatment for increasing the ratio of care at the patient's own cost.

Further, it is possible to display portions at the gums and jawbone where care is required by X-ray and actual images and combine the state of the jawbones as conditions for implanting an artificial root and the state of a virtual prosthetic shown by actual image based on the X-ray image and possible to display areas for regeneration by bone regenerating means.

An actual image, X-ray image, and microscope image can be summarized for easy viewing in a multiperspective image list. By editing this and displaying or printing out the result, it is possible to show the patient the order of treatment and prevention based on the intraoral situation in an easily understandable manner.

An actual image can be captured by, for example, coloring the plaque by phloxine etc. to enable the state of deposition of plaque to be visually observed, then forming the image shown in FIG. 23D, recording it at the recording device, then observing the state of deposition of plaque and state of the gums. Furthermore, based on the state of the gums, the plaque may be sampled and a microscope used to form an image of periodontal bacteria and edit the image in a state related to the sampled portion.

Furthermore, together with use of the X-ray image, an intraoral map which easily shows the state of periodontal disease in five rankings may be formed as image data and print data to enable suitable prevention of periodontal disease and prevention of tooth decay.

By using an actual image forming means which obtains a photographic image of all or part of the teeth by the above-mentioned panoramic image specification, it is possible to use a red color dye to show the plaque in the image data obtained.

The degree of depth of the red color of this image data is detected as a depth value by a software-based detecting means using for example the luminance detection technique. When this depth value exceeds a certain value, for example, when the value of the deepness based on the thickness in the state where the plaque has accumulated to an extent where periodontal bacteria can easily proliferate exceeds a value converted to luminance, a caution mark (symbol formed on the screen etc.) is attached to that portion of the image data. By providing this means, if outputting the image after dyeing the oral cavity to a computer monitor or printer, the parts with large amounts of deposition of plaque can be automatically displayed. This output display and the state of the gums can be viewed from the images and therefore periodontal disease can be efficiently discovered, prevented, and treated.

[Virtual Prosthesis Treatment Display of Oral Cavity]

The present invention can combine an X-ray image and an actual image side by side to form an easily understandable image, but it is further possible to superpose the virtual shape or color information of a prosthesis on this image and display the virtual state after treatment in a readily understandable form.

As one example, the X-ray camera means B8011 which is shown in FIG. 21A is given a means for displaying in combination the virtual shape which is shown in FIG. 21B, while the actual image capturing means B8012 which is shown in FIG. 21A is given a means for displaying in combination the virtual shape which is shown in FIG. 21C.

Furthermore, it is preferable to provide a virtual shape etc. storing means B8022 for storing virtual shapes in advance to enable them to be called up for use when displaying the virtual shapes in combination. As the virtual shapes etc., shape information of dentures, bridges, clasps, nonclasps, implants, inlays, crowns, and, other prosthetic and orthodontic devices are included. Further, the virtual shapes include color information. For example, shade guides comprised of color samples providing a large number of tooth shapes used when deciding on the hue are stored in advance or converted to data at the time of use. Ones storing color information of all teeth or single teeth are also included. This data may be successively stored when taking X-ray images or actual images of the oral cavities of patients while adding corrective and management data to the images as required.

In FIG. 21B, B8018 indicates a virtual shape adjusting means for X-ray image use. In the X-ray image capturing means B8011, this adjusts the virtual shape which is called up from the virtual shape etc. storing means B8022 by designation by the user or automatically to the size of the X-ray image captured or adjusts it to a color which is easily recognizable on the X-ray image but not disturbing so as to adjust it to a state enabling combination. B8019 indicates a combined display means for the X-ray image which combines the X-ray image and virtual state for display on the monitor screen.

FIG. 21B and FIG. 21C added virtual combined display means as ancillary members to the respective camera means, but these are not limited to ancillary members. They may also be set as main components in accordance with the objective. Alternatively, it is not necessary to superpose the actual image and X-ray image of FIG. 21. It is also possible to combine respectively independent virtual displays of the actual image and X-ray image. This combination may be performed by converting the images to the BMP, JPEG, GIF, or other general, format and, in the same way as a grid display etc., using the superimposition technique or using the transparency technique or superposition technique used in general graphic software.

In FIG. 21C, B8020 is a virtual shape adjusting means for real image use. This has a configuration the same as the virtual shape adjusting means for X-ray image use. B8021 indicates a combined display means. This has a function and configuration similar to the combined display means for X-ray image use.

Next, the configuration for combination of virtual displays shown in FIG. 21 will be explained in detail.

Figure 28A:
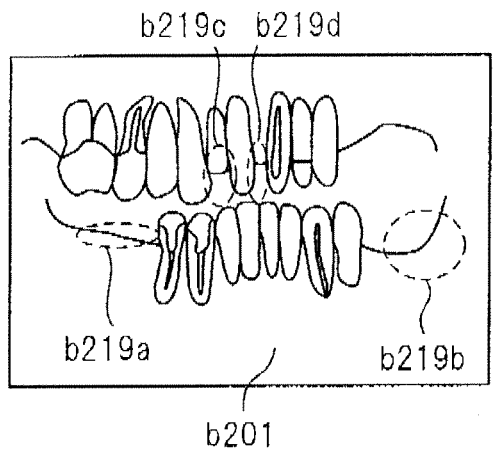
FIG. 28 is a schematic view for explaining an embodiment of the present invention.

In FIG. 21A, the X-ray camera means B8011 captures and forms a full tooth X-ray image b201 shown in FIG. 28A. This is, for example, a panoramic image which is obtained from an existing X-ray panoramic image camera system or all teeth captured several at a time by X-rays to obtain images, converting these to digital images, then processing these images to for example extract contours, then detect the common parts.

Figure 28B:
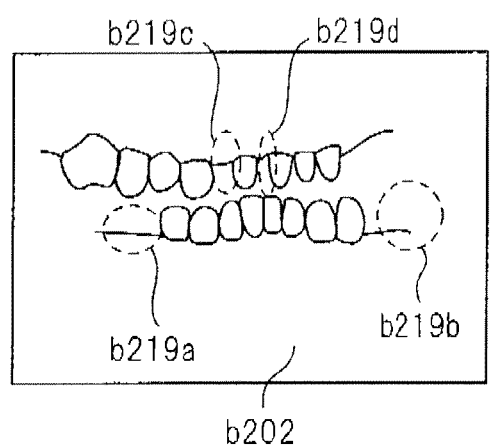

It is also possible to connect individual images at common parts to form a panoramic image of all teeth. Similarly, the actual image capturing means B8012 forms a panoramic actual image b202 of all teeth shown in FIG. 28B. Further, this full tooth image is not limited to this technique. It is also possible to use the technique of continuously capturing images then selecting and splicing together suitable images.

The treatment portions are found from the image. For example, in the image b201, there are a lost back tooth part b219a and lost back tooth part b219b and a lost part b219c of the front teeth and a gap b219d of the front teeth. The same is true in the panoramic actual image b202.

Figure 28C:
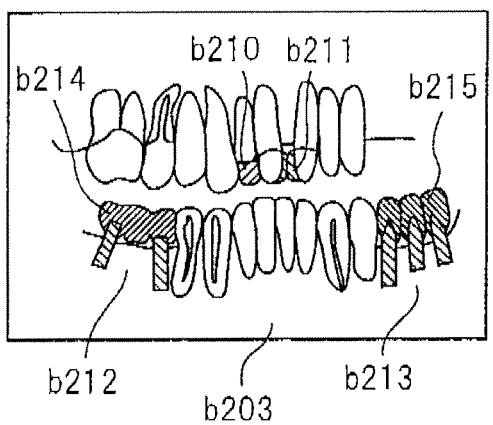

Each lost part is studied as to what kind of prosthetic is necessary. For example, if a front tooth prosthetic, the virtual shape adjusting means B8018 searches through the virtual shape etc. storing means B8022 to select a candidate for the front tooth of a shape enabling prosthesis. After selection, the selected image is read out and is displayed on the display monitor combined at the combined display means B8019 while selecting the size and color on the screen. FIG. 28C shows the image b203 which is obtained by for example combining virtual configurations. In the combined image b203, when artificial roots are deemed suitable for the lost back tooth parts b291a and b219b of the back tooth lower jaw, if bridging several artificial tooth roots b213 and superstructures b215, the bridge use implant b212 and bridge superstructure b214 are selected from the virtual shape etc. storing means B8022. The virtual shape adjusting means B8018 adjusts the size and color and combines the images at the combined display means B8019 for display on the monitor screen or mobile terminal monitor screen.

In the same way for the panoramic actual image b202 which is obtained by the actual image capturing means, the actual image use prosthetic teeth, inlay data, etc. are called up from the virtual shape etc. storing means B8022. The virtual shape adjusting means B8020 adjusts the size and color for display at the combined display means B8021.

In FIG. 28, b216 indicates the bridge superstructure b214 of FIG. 28C, while b219 indicates the superstructure b215 of FIG. 28C. b217 indicates a crown for a front tooth and corresponds to b210 of FIG. 28C. b218 indicates a gap prosthetic part b211 of FIG. 28C.

For formation of the gap prosthetic part b211, for example, if the teeth are crowns, formation is possible by enlarging the sizes of the crowns and making the two crowns contact in state. In the case of natural teeth, the technique is shown of grinding away some of the two teeth for insertion of the prosthetic.

In the combined images b203 and b204, the prosthetics are shown by hatching. For example, in the bridge use implant b212 and bridge use superstructure b214 in the combined image b203, when strength etc. is not preferable, three artificial roots and superstructures similar to the lower jaw right side are read out from the virtual shape etc. storing means B8022 and displayed replaced to allow adjustment of the state of the one at the lost part and the possible range of an implant while viewing the image.

Further, it is possible to call up tooth color data from the virtual shape etc. storing means and compare and, adjust the relationship of color with the adjoining teeth to make a decision. For example, for the front tooth prosthetic b210, it is possible to refer to general use models and adjust the shape and color with the adjoining teeth for combination and decision.

As the method of treating a gap b219d as well, it is possible to select the type of prosthetic which can be used, such as an inlay, crown, etc., from the virtual shape etc. storing means B8022, apply it to the image while adjusting it by the virtual shape adjusting means B8018, view the extent of combination by the combined display means B8019, and study the virtual shape as well. When this virtual shape is formed as a 3D shape, the virtual shape is made to rotate on the screen and a more realistic combined image can be obtained even with a planar intraoral image.

Figure 28D:
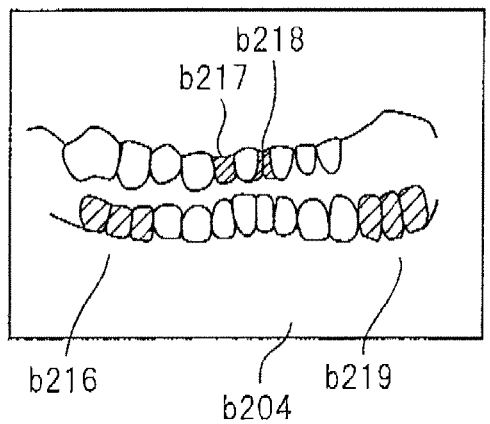

There is sufficient information for study even in the state giving the images of FIG. 28C and FIG. 28D, but the comparison portion detecting means B8013 of FIG. 21A designates a characterizing portion in the portions before combination out of the combined image shown in FIG. 28C, the comparison portion extracting means B8014 designates a characterizing portion in the portions before combination out of the image shown in FIG. 28O, and the comparing means B8015 compares the two comparison portions and temporarily records and displays the matched state.

Figure 28E:
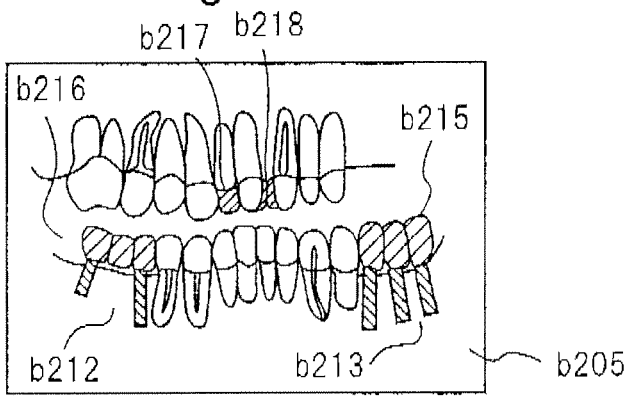

An image showing this displayed state is shown in FIG. 28E. The combined image b205 consists of the actual image and the X-ray image superposed. The number is the prosthetic state shown by the combined images b203 and b204. An X-ray image is hard to view. In particular, the gum portion is hard to view, but with such a combined image, the gum part of the X-ray image is displayed in an easily understandable manner. Further, the superstructures or teeth and the balance of the root parts can be displayed to be easily understood.

By virtually attaching the prosthetic on the screen, it is possible to display to the patient the oral cavity in a manner enabling the actual results of treatment to be imagined. Alternatively, it is attempted to realize a prosthesis suitable for the patient by presenting the patient with a virtual lineup of suitable colored or silver teeth or ceramic or other teeth. At the time of treatment, the virtual attachment to the X-ray image also becomes of reference in treatment to the dentist. For the virtual data, it is possible to use already available data as it is or enlarged or reduced for combination. In addition, after combination, it is possible to convert the actual distance to prosthetic data and obtain color information and whitening and corrective data.

By combining a virtual shape with a prosthetic portion, it is possible to find part of the size of the actual prosthetic, so the virtual shape or other data can sometimes be used as is as data for prosthetic production.

Further, this technique is performed by a computer. Part of the size of an actual prosthetic is quickly learned. This can sometimes be used as production data as is for the prosthetic.

[Mobile Terminal Type Information Inputting/Outputting Means]

Next, an embodiment of the present invention will be explained in detail with reference to FIG. 24. In the figure, 1a01 indicates a small sized battery of a button type, tube type, sheet type, pin type, etc. Further, either a primary cell or a secondary cell may be used. 1a02 indicates a voltage boosting means such as a DC-DC converter, chopper, or switching regulator which, for example, has the function of boosting a voltage of 1.5V 3D to around 3V, 1a03 indicates a control means such as a one-chip type computer or ASIC or other control chip. 1a04 indicates a display means formed by a liquid crystal panel etc. which can display a 2D image.

1a05 indicates a terminal side communicating means which is suitably provided by the type of the wireless medium 1a0C. If a radio wave, a circuit which includes a carrier wave output means for use up to several GHz, an FM, AM, PCM, or other modulating means, and a transmission and reception antenna is used. If light, a combination of an LED, laser, and CDS or other light receiving element is used. Among these, Zigbee Module (brand name) using radio waves etc. can be suitably used. In addition, sometimes a USE connection or other general use cable, dedicated cable, or other cable communicating means is also possible.

1a06 indicates an inputting means such as a keypad, touchpad, or other means which is depressed, touched, etc. to convert the portion intended by the user to an electrical signal. Sometimes a liquid crystal panel which has a touch panel function or other device which doubles as the display means 1a04 and the inputting means 1a06 is used.

1a07 indicates a storing means which stores a program for editing patient data and displaying it on a display. The patient data is mainly recorded at the host device side, so temporary storage is also possible. It need only be stored up to the capacity. 1a08 indicates an electrical line which directly connects the inputting means 1a06 and the terminal side communicating means 1a05. This exhibits the function of direct transmission of a signal through the terminal side communicating means 1a05 if a key is pushed and may be configured in the same way as a circuit line between a keyboard and computer. When a control means 1a03 acts in its stead, it is sometimes unnecessary.

1a0B indicates a host device which is configured by a combination of a recording means loll which stores patient data, patient intraoral data, patient health data, attendance records and other dental employee related data, dental diagnosis and treatment data, electronic patient chart data, patient reservation data, etc. in a database and all other data relating to the dental practice, a host computer 1a10, and a communicating means 1a09.

1a09 indicates a host side communicating means which is configured paired with the mobile terminal side terminal side communicating means 1a05. It is not uncommon for a plurality of mobile terminals to be utilized for a plurality of patients, so the mobile terminals or communicating means 1a09 preferably can be set to multiple channels and input from only specific mobile terminals can be made to be accepted.

1a10 indicates a host computer which is configured by a combination of a display device for display use, a keyboard, mouse, printer, and other peripheral devices. 1a11 indicates a recording means such as a hard disk, SD, DVD, USB memory, or other recording medium which can be housed in the host computer 1a10. The communicating means 1a09 may be similarly connected at the outside and may be built in 1a12 indicates a communication network such as the Internet, an in-house LAN, Intranet, etc. 1a13 indicates another host device which is configured in the same way as the host computer 1a10 of the host device 1a0B and may store patient data etc. which the host device 1a0B does not hold. Further, for example, by sending treatment data from a distant location to a mobile terminal, it becomes possible to assist the diagnosis and treatment of a dentist operating it.

Figure 24:
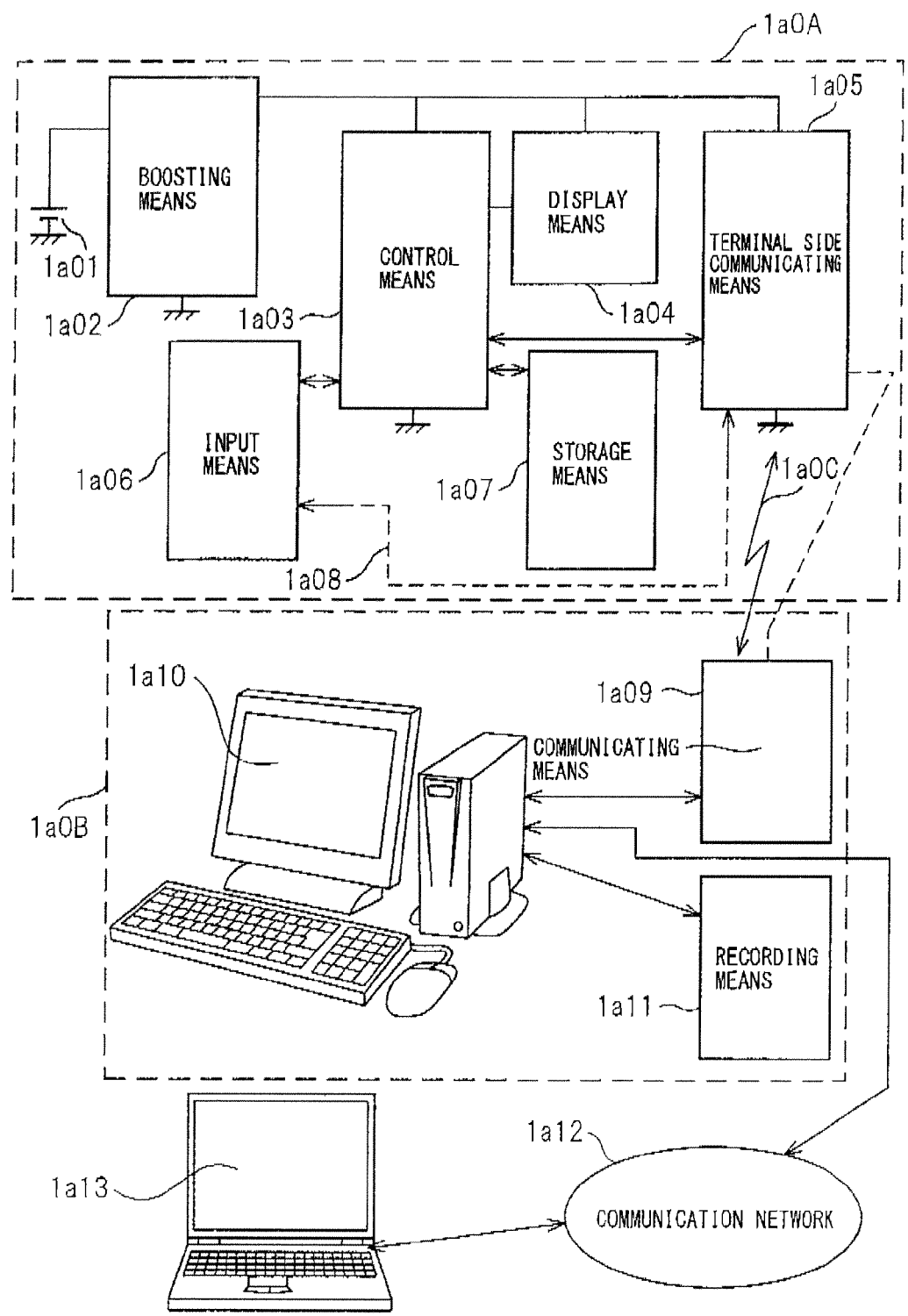
FIG. 24 is a block diagram for explaining an embodiment of the present invention.

Next, the operation of the embodiment which is shown in FIG. 24 will be explained.

The voltage of the battery 1a01 is boosted by the voltage boosting means 1a02 and supplied to the different means. This voltage boosting means 1a02 is used to, for example, boost the battery voltage of 1.5V to 3V or more to enable the CMOS control device etc. to be driven.

The control means 1a03 may call up, run, and display on the display means 1a04 a diagnostic data processing program at the time of dental diagnosis and treatment from the storing means 1a07. Otherwise, data which is sent from the host computer 1a10 may be displayed as it is on the display means 1a04.

Since a wireless communicating means is used, first, or in the middle of operation, the state of communications is examined and the communication situation is confirmed. Further, even if the wireless connection is broken in the middle, the control means 1a03 may be configured to enable provisional input and output while it is broken.

In accordance with the display of the display means 1a04, the operator pushes, touches, or otherwise operates the input buttons of the inputting means 1a06. In this case, for example, if pushing the key "1" of the inputting means 1a06, "1" is output and displayed through the control means 1a03 on the display means 1a04 and is sent through the terminal side communicating means 1a05, wireless medium 1a0C, and communicating means 1a09 to the host computer 1a10. If the executed button signals reach the host computer 1a10, for example, when the patient name is sent from the inputting means 1a06 to the host computer 1a10, a search is conducted in the database in the host computer 1a10 receiving it and the data is sent to the mobile terminal 1a0A. The sent data is adjusted for display use at the control means 1a03 through the terminal side communicating means 1a05 and is displayed at the display means 1a04.

Further, the system may be configured so that the data which is transmitted from the host computer 1a10 to the mobile terminal is displayed as is at the display means 1a04 of the mobile terminal 1a0A. Alternatively, the controlling means 1a03 may call up and run a program from the storing means 1a07, process data which is sent from the host computer 1a10 by the program, and display the results on the display means 1a04.

As the data which is transferred by a wire communication means, sign data, numeric data, symbol data, and other text data and image data are sent. When the host computer 1a10 does not have the required content, sometimes the data is acquired from another host device 1a13 through the communication network 1a12.

The input from the inputting means 1a06 is further recorded at a host device side recording means 1a11. For example, when a periodontal pocket depth value is obtained and is manually input from the inputting means 1a06, it is recorded as is through the host computer 1a10 in the recording means 1a11, but to confirm the input value, the display means 1a04 may also be provided with a circuit for displaying it.

Next, the operation of an embodiment of the present invention will be explained in more detail while referring to FIG. 24 and FIG. 25.

Figure 25:
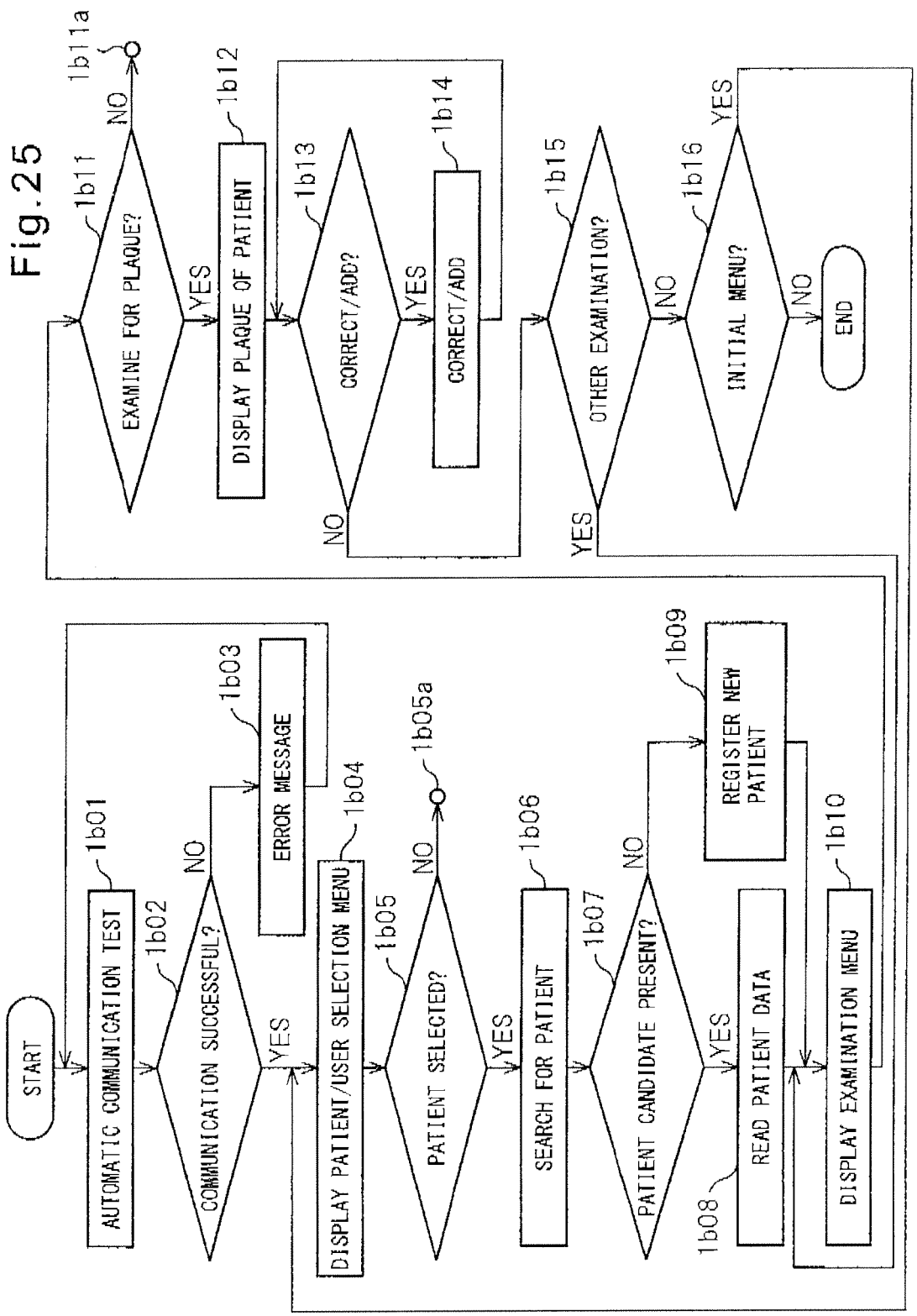
FIG. 25 is a block diagram for explaining an embodiment of the present invention.

At the time of start of use, as shown by step 1b01 shown in FIG. 25, an automatic communication test is run. If the communication test fails (NO) (step 1b02 shown in FIG. 25), an error message is displayed (step 1b03 shown in FIG. 25) and an automatic communication test is run again at step 1b01 shown in FIG. 25.

If the automatic communication test succeeds (YES), the host computer 1a10 which is shown in FIG. 24 outputs the patient selection menu display data through the communicating means 1a09, wireless medium 1a0C, and terminal side communicating means 1a05 to the control means 1a03. The control means 1a03 to which this data is input outputs this to the display means 1a04. In this case, what the host computer 1a10 outputs is display use data. When displaying this display use data at the display means 1a04, a display use program which is read out from the storing means 1a07 is run by the control means 1a03 to form this in this illustration.

Note that, the patient selection menu may also be recorded as a program in the storing means 1a07 of the mobile terminal. Alternatively, the data may sometimes be directly displayed at the display means 1a04 without going through the control means 1a03.

The display means 1a04 shown in FIG. 24 displays the patient/user selection menu (step 1b04 shown in FIG. 25).

The case where, at step 1b05 shown in FIG. 25, the patient selection menu number is input by depressing the keypad (yes) will be explained. If something else is selected (no), the operation shifts to the terminal 1b05a. There, a similar operation is repeated, so illustration and explanation will be omitted.

The patient selection (for example, depression of "1" on the keypad) and the signal of "1" are sent as they are through the wireless communicating means to the host computer 1a10 where a program operates which displays a patient name input box on the display means 1a04. At step 1b06 shown in FIG. 25, if a patient name or patient code is input by depressing the keypad, each time depressed, a code and text data corresponding to the depressed key of the keypad are sent to the host computer 1a10. If the enter key is depressed, the stored data in the recording means 1a11 of the host computer 1a10 is searched.

For this search, in addition to a full match search for the entire name, a partial match search where only the surname and first name are input etc. may be utilized, so a list of patients obtained in the case of a partial match search is displayed.

Whether or not there is a patient candidate is displayed. If there is, a key showing that there is pressed. The pressed information is sent directly to the host computer 1a10. The host computer 1a10 then calls up the patient data from the database and sends it to the mobile terminal 1a0A.

This patient data is displayed on the display means 1a04. In this case, the control means 1a03 lists the data for display as it is for each paragraph code.

Furthermore, when displaying patient data, the control means 1a03 may read out a display use program from the storing means 1a07 and run it so that the display means 1a04 displays an array in accordance with the program.

If there is a patient candidate (yes) at step 1b07 shown in FIG. 25, the host computer 1a10 shown in FIG. 24 sends the patient data to the mobile terminal 1a0A (step 1b08 shown in FIG. 25). If there is no patient candidate (no) at step 1b07 which is shown in FIG. 25, the patient is registered as new or a search is conducted again, but display of the routine for the repeated search is omitted. Only the step for new registration of a patient (step 1b09 shown in FIG. 25) is shown.

In the case of new patient registration, if operating the keypad of the inputting means 1a06 to input data, the keypad input is sent as is to the host computer 1a10 where it is registered in the database of the recording means 1a11. Further, in the case of registering a new patient, in addition to input from the inputting means 1a06, input from the host computer 1a10 is also possible. Whatever the input, the patient is newly added to the patient information which is recorded in the recording means ball of the host computer 1a10 (step 1b09 shown in FIG. 25).

If the patient is identified and the records are displayed, next, at step 1b10 which is shown in FIG. 25, a menu for examination is displayed at the display means 1a04 of the mobile terminal 1a0A. This menu display shows the data which the host computer 1a10 outputs and displays or the data which is processed by running a program which is called up from the storing means 1a07 and is displayed by the display means 1a04 by the control means 1a03 as an example.

When the examination menu related information is displayed as text sentences, it is displayed from host device 1a03 through the wireless medium 1a0C and the control means 1a03 as is. In the case of a display having a pattern of arrangement distinctive to the database, an application program may be read out from the storing means 1a07 and run (step 1b10 shown in FIG. 25).

FIG. 25 shows the case where plaque examination is designated. Other options (1b11a) are omitted. If designating plaque examination at step 1b11 which is shown in FIG. 25, the signal which is obtained by pressing the inputting means 1a06 to designate input is directly sent to the host computer 1a10. The host computer then outputs the past plaque data.

The past plaque data which the host computer 1a1 calls up from the recording means 1a11 and outputs to the mobile terminal 1a0A is data of numerical values, symbols, text, moving images, still images, etc. The control means 1a03 runs a plaque display program which was called up from the storing means 1a07 and uses the data which is output from the host computer 1a10 as the basis for display.

Data as what stage of plaque to add at what side surface of what tooth is sent to the host computer 1a10 shown in FIG. 24 by operation of the keypad at the mobile terminal side. The host computer 1a10 records data to this effect in the recording means 1a11.

If, at step 1b12 shown in FIG. 25, the plaque of the patient is displayed, the routine proceeds to step 1b13 shown in FIG. 25 for determination of whether to make corrections or additions to the same. If making corrections or additions, the above-mentioned corrections or additions (step 1b14 shown in FIG. 25) are performed.

When the modifications and corrections or additions are completed, at step 1b15 shown in FIG. 25, it is judged whether to perform another examination. If performing another examination, an examination menu of step 1b10 shown in FIG. 25 is displayed. If not performing another examination, whether to return to the initial menu is displayed (step 1b16 shown in FIG. 25). If returning to the initial menu, the patient and user selection menu of step 1b04 shown in FIG. 25 is displayed and the processing is continued. If not returning to the initial menu, for example, the routine may be ended.

Note that the above configuration is only one example. For example, smart phones and mobile phones may sometimes also be used as they are as mobile terminals for managing dental information. At the very least, the dental employee can carry the device and operate it to input, display, and record intraoral information, dental office information, dental employee information, and other related information. If necessary, he or she can read out information from the host terminal and record information there. The devices need only be ones by which dental employees can display and input necessary information in a shared manner. They may be configured in accordance with the purpose of use.

The above operation enables wireless communication of keypad codes and numerical values, text, symbols, text data, images, moving images, and other data. Real time display is possible, so even if using the terminal at the same time as diagnosis and treatment, stress-free use is possible. Alternatively, when wearing the host device on the waist or back or when there is no problem even if connecting the host device and the mobile terminal by cables, sometimes wireless communication is not necessary and communication by cables is possible.

The present invention enables centralized management of dental information by the above-mentioned mobile terminal. As the information to be managed, for example, dental office information, patient information, patient chart information, account information, diagnosis and treatment fee information, etc. handled by reservation management systems for dental diagnosis/treatment, electronic patient chart systems, reception computer systems for preparing reception data from accounting information and diagnosis and treatment information, recall management systems relating to repeat patients, etc. can be input. For example, dental office information which is handled by a business management system which is provided with the function of preparing and displaying graphed reports, digital X-ray information, dental microscope information, dental CT information, intraoral camera and other examination information, treatment use dental unit information, patient chair and other data information, probes for periodontal pocket examination use, and intraoral information from other devices, and attendance and other information on dental employees such as dentists, dental hygienists, dental staff, reception and administration staff, dental technicians, and other employees may be shown. In addition, toothpaste information, plaque related information, periodontal bacteria information, etc., preventive information, lifestyle disease related information, and other such information which is not limited to the oral cavity, but relates to diseases relating to periodontal diseases and other indirect diseases, for example, blood pressure and blood information etc. is sometimes also included.

Further, useful information about the clinic, useful information about the patients, questionnaire information, business information, etc. may be centrally managed, but the centralized management may not only cover all information related to the dental practice, but also just the required part of the information.

For example, when, like in the case of an analog X-ray camera device, data can only be obtained by analog photographs or images or in the case of handwritten data, an image scanner, digital camera, hard copy of the computer screen, or other digital converting means is preferably used to convert this to a digital signal for management.

The data may be centrally managed by the above mobile terminal, but a tablet type, notebook type, desktop type, or other dental computer may also be used for centralized management. In particular, a network specification terminal used primarily for the Internet or a mobile terminal may be utilized. A mobile terminal which is connected, to the Internet by a wireless LAN may also be utilized.

Further, the present invention can provided centralized information and can provide data processing etc. using the cloud computing technique. For example, a mobile terminal or host terminal may use application software which is provided by one or more center organizations through the Internet and input and output data by dedicated or general use browser software at the terminal side. The terminal side need not install the centralized management application software. By just installing Internet Explorer®, Firefox®, or other browser software and using this browser software to run software for centralized management of dental information of a center, it can input and output data. It is therefore possible not to worry about the capacity of the recording device at the terminal side and provide both small size and simple design.

Note that, rather than a general use browser, it is also possible to use dedicated software for starting up software for centralized management of dental information. Further, the terminal side may sometimes store all information at the cloud side resources and sometimes store part of the information requiring secure management such as personal information at the terminal side.

As the type of the cloud, for example, a system which is constructed as a private cloud of just an in-house system, just a center organization, or a group of participating dentists where leakage of information would be a problem is preferred, but so long as security is reliable, it may be configured by a public cloud which is constructed by outside computer information service organizations. Sometimes, the entire part may be made a private cloud or a public cloud.

This mobile terminal may be carried for use by not only dentists, but also dental hygienists, dental reception and administrative staff, dental technicians, and other related staff and sometimes patients. Data can therefore be shared with other staff. Alternatively, by providing a function of switching IC cards or other carriers for identifying individuals, a single terminal may be alternately used exclusively.

For centralized management of the data, it is preferable that there be compatibility between the data which the different systems handle, but compatibility is not necessarily required. For example, when using hard copy data of the screen etc., it is sufficient that the data be displayed on the mobile terminal and be able to be operated there.

In the present embodiment, use in real time where the server provided with the external database and mobile terminal can communicate is preferable, but the invention is not limited to this. The operation may be temporarily recorded in the mobile terminal and, when communication with the server is enabled, the temporarily recorded data may be automatically transferred to the database by the batch method.

For example, when operating a patient reservation system on a mobile terminal, when determining the schedule of visits to the clinic for patient treatment and preventive care, if inputting a candidate reservation date from the terminal, the reservation status data is read out from the database and compared. It is possible to display overlapping scheduled dates on the screen of the mobile terminal and prompt change. Alternatively, it becomes possible to enter the schedule into a plurality of treatment and preventive care screens in an input display field of the mobile terminal screen and send a print command from the mobile terminal so as to print out the schedule of treatment and preventive care by a related printer. This can be then given to the patient.

The mobile terminal may be connected with a host device wirelessly or by cable and also may be connected with an intraoral camera by cable or wirelessly. In this case, it is possible to perform suitable positioning for capturing a tooth or tooth surroundings which require treatment or preventive care.

Not only is it possible to centralize information between a mobile terminal and host terminal, but also when using a host terminal as a server when providing each dental diagnosis and treatment chair with a terminal as a dental computer, it is possible to achieve centralized management of information between the host terminal and the computers of the individual chairs.

For input of data to the mobile terminal, in the above-mentioned way, use may be made of operating buttons or rotary dials of the pressing type, sliding type, or type which are operated by bringing a finger or pen or other such object into contact with screen. In addition, virtual buttons or virtual keyboards on the screen and, when an intraoral camera or other peripheral device, is connected, the above mentioned buttons or dials on the peripheral devices may be used. In addition, audio input and recording by an integrally provided microphone or a scanning and recording function by a camera which is integrally or separately provided may be provided to facilitate free input. Further, the scanning and recording function may use a dental camera to record a photographic image.

When inputting text or a handwriting image by an electromagnetic induction type pen or resistance film pen when inputting information onto the screen of a tablet type computer, mobile terminal, etc., it is also possible to fetch handwritten input data. For example, when providing an explanation to the patient, when explaining a treatment technique to a dental hygienist, and when otherwise display on the screen by handwriting is suitable, if inputting information directly from a mobile terminal by handwriting, it is possible to have this displayed as it is or have it displayed synchronously on the monitor screen of the host terminal to allow explanation to the patient or explanation to another employee or to have it recorded as is and used later. In particular, when entering information into the intraoral image by handwriting, the information can be used as is as patient data.

Furthermore, it is also possible to input and output audio data to obtain an accurate grasp of the intraoral situation. With the audio data, for example, when talking with a user of another mobile terminal, it is possible to designate a window on the mobile terminal screen and simultaneously display the audio and image. Alternatively, the audio data is converted as is to text data or the handwriting text is converted to text data so as to reduce the required storage capacity. In particular, when diagnosing the oral cavity, specialized terms relating to the state of tooth decay etc. can be recorded in advance as audio data and compared against audio which is input through the mobile terminal for conversion to text data. This enables data which had been previously entered to automatically be made electronic data.

By recording prerecorded audio samples and text data of specialized terms as tables in a recording device, comparing the input audio data and audio sample data, and converting the matching or substantially matching audio sample data to corresponding text data, it is possible to record accurate dental information.

The present embodiment enables input of electronic patient charts and other patient information, input of diagnosis and treatment fee information, and input and output of information relating to other dental administration under centralized management, but in this case, the host terminal and the mobile terminal may be synchronized in at least the input state. That there is input from the host terminal, that input is displayed on the mobile terminal. The output display is also performed synchronously in the same way. The screen synchronization software can be run by a mobile terminal which has a built-in general use computer by utilizing the commercially available software Sync+®. Alternatively, the mobile terminal is one shown in a state which utilizes a function built in advance or connects with a USB terminal which is provided with a LAN function to as to be able to utilize a wireless LAN. This enables sharing not only between the host terminal and mobile terminal but also with another mobile terminal through the host terminal or direct sharing between host terminals. The "direct sharing" may be sharing utilizing electromagnetic waves, infrared rays, and other wireless media and also through relay terminals.

In the case of home dental treatment, if the storage capacity and processing ability of the mobile terminal are low and data cannot be recorded, it is also possible to use a separate storage device or e-mail etc. to clean up the part which cannot be stored as data and use a dedicated or public line to transmit it to the host terminal sequentially or every certain stored amount.

Such synchronization of display between terminals enables input from a host terminal provided with a keyboard, mouse, or other input interface and thereby enables quick input since when dental diagnosis and treatment is for example performed on a common room, complicated input from the mobile terminals takes time.

Further, in centralized management of dental information using a mobile terminal or other terminal, it is also possible to automatically process time series data. For example, the date and time of the end of treatment or suspension of treatment of a patient after treatment is read out from a database and compared with the current date and time. When a preset time period has elapsed after treatment, that fact is displayed an the mobile terminal or host terminal. Alternatively, it is also possible to automatically print out e-mails directly.

The host terminal may automatically notify the mobile terminal when the time for preparing diagnosis and treatment fees and may automatically notify and adjust attendance figures for days where there are no reports etc.

The mobile terminal may connect with an X-ray image capturing system, intraoral camera, microscope, or other peripheral devices directly or through a host terminal so as to, for example, display the camera outputs by these peripheral devices in real time on the mobile terminal and record them in patient data folders identified by the patient names etc. These peripheral devices and dental chairs, lighting equipment, etc. may also be controlled in operation from the mobile terminal. At that time, records of the control operation may be logged into the patient chart.

The patient data folder is preferably recorded mainly in the host terminal in a nonredundant state and can be read by a search from individual terminals. There may be several copies of patient data folders such as at the individual terminals in the case of temporary use, but when recording it continuously, presence in a single storage area is preferable. This storage area may be not only the host terminal, but also a distant location through a network.

The mobile terminal may further be able to swap audio, image, or text information with the patient. In particular, as use of mobile terminals becomes generalized, the patient may also carry such a mobile terminal. If the patient carries one, preferably he or she can only view information required for himself or herself as a patient. This is because, for example, if developing application software for using smart phones and other mobile phones as the above-mentioned dental management terminal, a patient need only install a specialized application to enable such use.

[Dental Explaining Means]

The present embodiment explains dental diagnosis and treatment by for example displaying a panoramic image of the entire row of teeth of a patient and an image of the treatment portion on a computer monitor (display) screen and combines subdivided moving images in accordance with the objective for reproduction as a combined moving image so as to enable individual patients to easily understand explanations of treatment. The dentist may use an existing sequence of moving images obtained by combining the subdivided moving images in advance or may select, edit, and combine images in advance.

For the technique by which the dentist selects and edits images in advance, a semicustom or existing combined moving image sequence is selected for use, but an example of combining all explanatory data to prepare at least one moving image sequence will be explained in detail with reference to FIG. 26.

Figure 26:
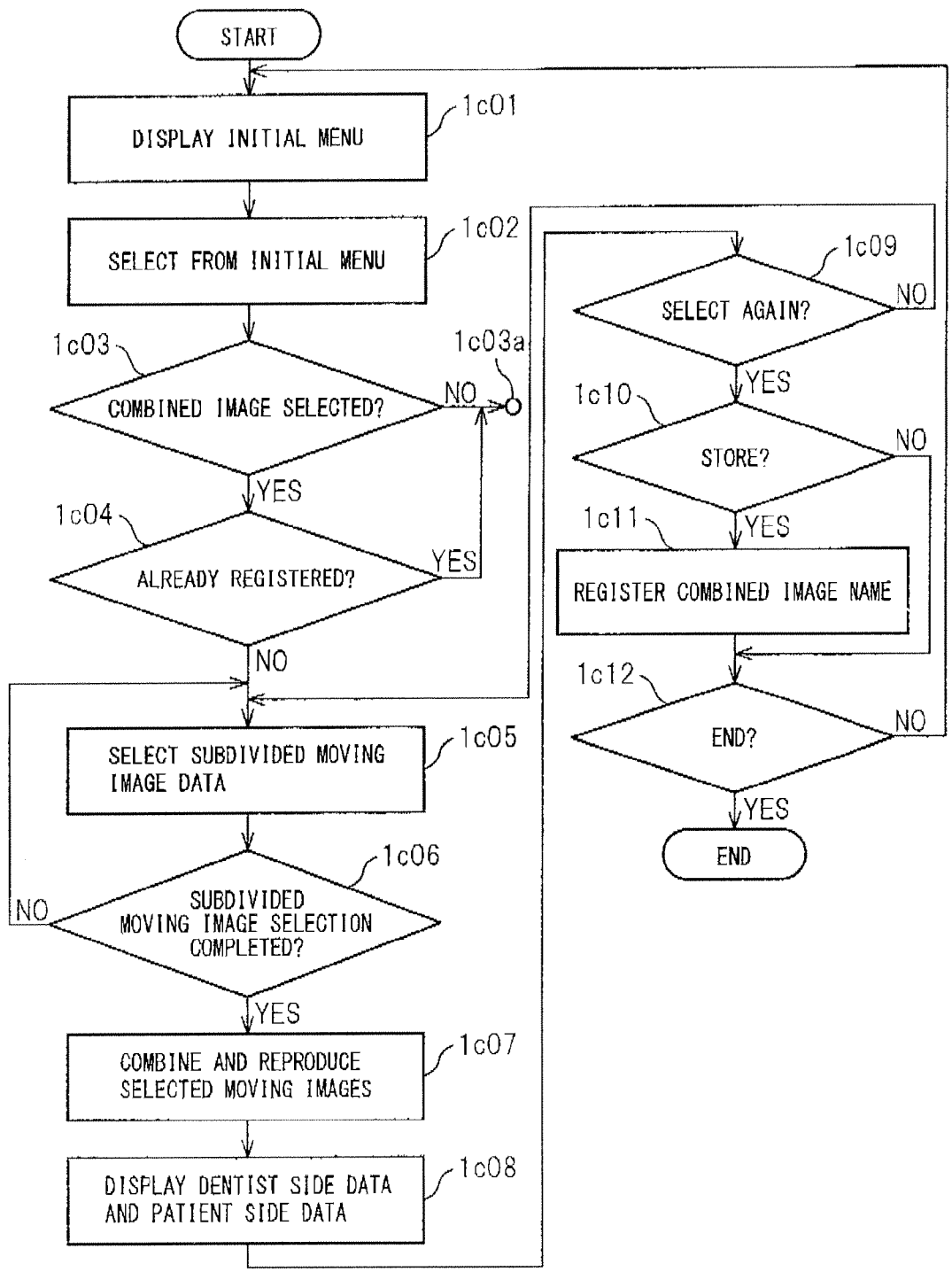
FIG. 26 is a block diagram for explaining an embodiment of the present invention.

FIG. 26 is a view for explaining the operation in the case where the dentist sets one combined moving image in advance. In the figure, 1c01 is the display of the initial menu. A list which shows the existing moving image sequences, a list enabling semicustom connection and editing, and a list of individually subdivided moving images are displayed and are selected in accordance with the objective.

1c02 is the step of selecting one of the initial menu displays.

1c03 is the step where the steps to be executed are branched according to which is selected. In the case of NO, the routine proceeds to selection of another combined moving image (not shown) through the terminal 1c03a. In the case of YES, the routine proceeds to the step (1c04) of judging whether an image is already registered among the combined moving images by the technique of searching through the names of moving images or searching for combinations of distinctive codes assigned to the subdivided moving image data. If provisionally registered (YES), the routine proceeds to selection of another combined moving image through the terminal 1c03a.

When not registered, a list of the subdivided data is displayed and furthermore editing regions are displayed. The list of the subdivided data may be broken down by objectives or may be formed into an array or formed into a tree.

In the selection 1c05 of the subdivided moving image data, the data is moved from the list to the editing region by the copy and paste or drag and drop technique to edit the time-series explanatory data.

In FIG. 26, when selection of the subdivided moving images has ended (1c06), the selected combined moving image sequence is reproduced on a test basis (1c07).

Figure 27:
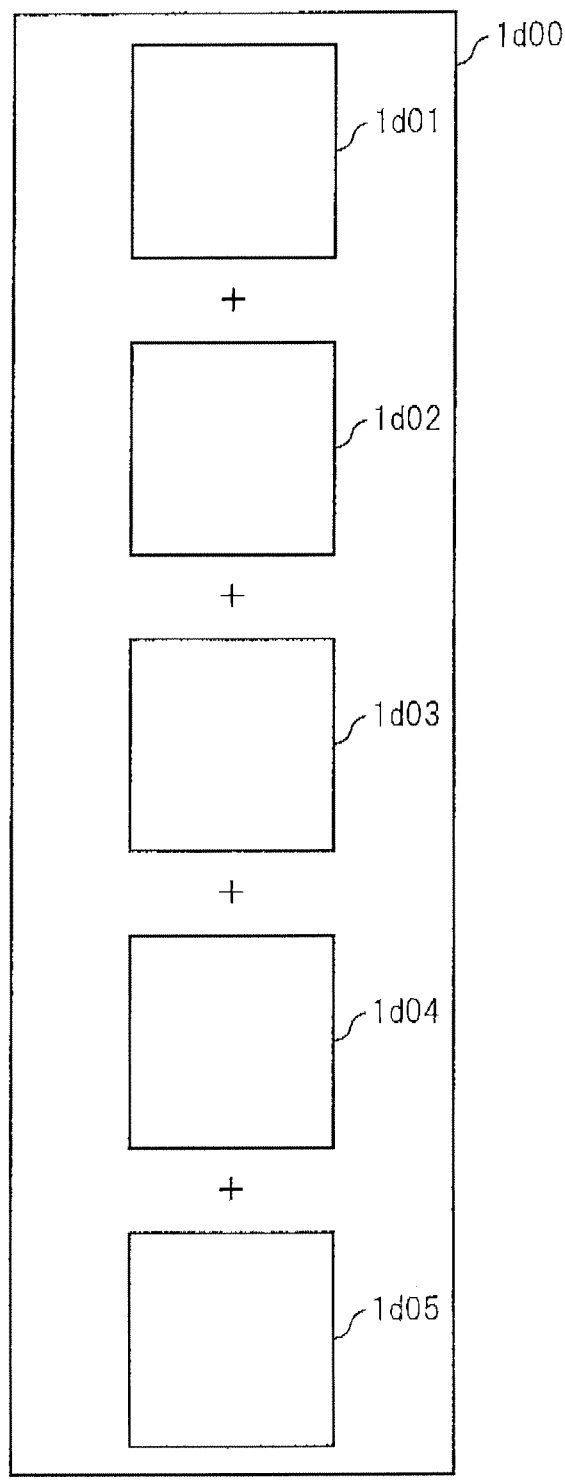
FIG. 27 is a schematic view for explaining an embodiment of the present invention.

FIG. 27 shows an example of combination of the combined moving image. In the figure, 1d01 indicates a moving image of recovery of the gums after tooth extraction, 1d02 indicates a slanted moving image of the adjoining teeth, 1d03 indicates a moving image of elongation of a facing tooth, 1d04 indicates a moving image of formation of a support tooth, and 1d05 indicates a moving image explaining the dental work shown in FIG. 1 and a moving image showing the setting of the dental work. These individual moving images are preferably not single, but a plurality of moving images.

The series of moving images from 1d01 to 1d05 are made the combined moving image 1d00 which is named and is recorded in a recording device. Code sequences assigned to the individual subdivided moving image data in advance are recorded by the recording device, then the combined moving image 1d00 is displayed on the computer screen as a single icon.

The combined moving image 1d00 is comprised of moving images which are successively combined to form one moving image which can be continuously reproduced. The individual moving images are subdivided. They are preferably respectively set with patient capacities and dentist capacities. The individual moving images are, for example, the WMV, AVI, or MPEG format. They may be selected and successively combined by existing moving image editing software.

Furthermore, at step 1c08, the dentist side data and patient side data are displayed, and the time and cost are displayed. Preferably, the use of another technique for lower cost, shorter time, and higher profit is explained in the display as an alternative.

At step 1c09, even if the combined moving image has already been prepared, if desiring to reselect it, the routine is made to proceed to selection of the subdivided moving image data. 1c10 is the step of selecting whether to store this menu list. If storing it (YES), at step 1c11, the name of the combined moving image is input and registered for storage. When not storing it, the routine returns to the end step it is selected whether to perform editing or to end the routine as it is (1c12).

FIG. 26 explains the operation when a dentist prepares a combined moving image, but there is a large number of actual subdivided data, so depending on the selected data, sometimes time is taken. Therefore, it is also possible to form samples in the manner of an editing box for each type of explanation in advance. This embodiment may further register the intraoral image of the patient itself in the subdivided moving image for utilization as part of an explanation of treatment, prevention, etc. unique to the patient.

The present embodiment is mainly utilized for obtaining informed consent. From the viewpoint of shortening the treatment time for the patient and for making the explanation more efficient, more efficient viewing is preferable, but in this case, subdivided moving images of durations of several seconds to several minutes are presented by the dentist while explaining them to the patient. An auxiliary screen which explains terms used by the dentist may also be displayed to make the explanation easier for the patient to understand.

For example, a list of the subdivided data is displayed on a computer screen by icons, tables, etc. The data is given simple titles easy for the patient to understand. This list is edited by displaying it on the above-mentioned mobile terminal and having the dentist select from it. The selected state is displayed on the screen which is viewed by the patient.

Further, it is also possible to discuss treatment with a patient while using a simple mobile terminal to prepare a combined sequence of moving images selected for the patient and display this to the patient on an immediate basis. That is, a mobile terminal provided with a display unit and input interface which is mainly carried by a dental employee and a terminal provided with a display monitor by which a patient or person desiring preventive treatment (referred to as "patient etc.") can view the information is used by the dental employee to search for and edit moving images, subdivided moving images, or combined moving images which include content to be informed to the patient etc. on the mobile terminal. When the editing ends, the image is transmitted to the patient viewing terminal. Further, in this case, moving image data may also be transmitted, but it is also possible to transmit identification data attached to the moving image data, have the terminal for patient viewing receive this identification data, and process the moving image based on this identification data sequence in real time for display on a screen.

Furthermore, the dentist etc. can carry a mobile terminal and in that state play back a moving image on the screen display of the terminal which the patient etc. views, stop it, display or not display the patient data, and perform other remote operations.

Further, the image and data which the patient is viewing can be synchronously displayed on a mobile terminal which a dental employee carries. In particular, when using the intraoral camera which is shown in FIG. 1 to display and explain the oral cavity of a patient, the explanation and case studies match and become easier to understand.

Furthermore, in the present embodiment, the mobile terminal which is shown in FIG. 24 may be used to edit the moving image data and to output and display the edited image on a computer monitor which the patient can view.

Further, the mobile terminal may be used to enable operation of display of a moving image on a monitor which is connected to a dental computer which a patient can view.

[Gum and Tooth Boundary Detecting Means]

The present invention includes a configuration for enabling the boundary between teeth and the gums to be clearly set.

The image of an intraoral camera is usually captured while lighting up a dark narrow space, so, for example, in the means for forming a panoramic image by computer image processing which is shown in FIG. 8 and FIG. 10, if detecting the common parts between images, when explaining dental treatment to the patient, etc., it is sometimes difficult to discern the boundary between the gums and teeth and the like due to the close color and the effects of saliva etc.

Therefore, a combination configuration which is comprised of a contour extracting means for extracting contours of teeth in an actual image, a color component image converting means for converting an actual image to component colors to clarity the shapes of the teeth and the gums, and a combined image forming means for combining the image which was converted by the color component image converting means and the contour extracted image is used to enable extraction of the contours of the teeth and gums even at locations of staining of the teeth or poor illumination.

The contour extracting means is for example comprised of a means for applying a 3D Fourier transform to an image and a means for detecting only a phase signal in a frequency region which shows changes in contrast of a image after the Fourier transform and applying an inverse Fourier transform. In addition, a Z-transform system and Laplace transform system etc. may also be utilized in some cases.

The color component image converting means, for example, is a means for forming images broken down into component colors shown by the RGB color system, La*b* color system, HSV color system, XYZ color system, xyY color system, L*u*v* color system, Munsell color system, Ostwald color system, NCS (Natural Color System), DIN color system, or other color system, selecting from among these a component color by which the shape can be clearly seen, and forming an image based on this component color or a means for combining component colors without regard to the color system to form a component color by which the shape can be more clearly seen and form an image based on that component color. This selection is preferably performed by measuring and determining a component color suitable for the intraoral image, but, for example, combination of any one of the L component image, a* component image, or b* component image of the La*b* color system and any one of the H (hue) component image, S (saturation chroma) component image, and V (brightness lightness value) component image of the HSV color system is shown. Combination of component colors of different color systems is sometimes preferable. The component colors need only be selected and combined for conversion to a component color by which the shape can be clearly seen or for combination of a plurality of component colors. Further, a "component image" includes an image which enhances the component obtained by adjusting the values showing the component values in for example a program.

Further, in addition to selecting a component image by which the shape can be clearly recognized, a combination of colors by which a person can recognize the boundaries more is used for coloring. For example, application of a R (red) component image to the gums and application of a G (green) component image to the teeth is shown.

Further, the component colors which are shown here not only include ones which are detected from an image, but also ones obtained by newly coloring while using colors which clarify the boundaries.

Further, the combined image forming means combines the contour image which was obtained by the contour extracting means and the image which was obtained by the color component image converting means and, for example, like the chroma key technique, makes the parts of the contour image other than the contour part the same color system and makes the color component image transparent etc. for combination. Alternatively, after that combination, to further enhance the color component image, means may be employed to change the color of the gum parts or more deeply enhance them to a red color system and to change the color of the teeth or more deeply enhance them to green so that the boundaries become more differentiated visually to people or mechanically. Further, depending on the color component, if converting the gum color to red and the tooth color to green, those color component images may be converted to. These means are preferably all realized by computer software, but sometimes are comprised of gate arrays and PLD (Programmable Logic Devices) and other custom and semicustom ICs.

Figure 29:
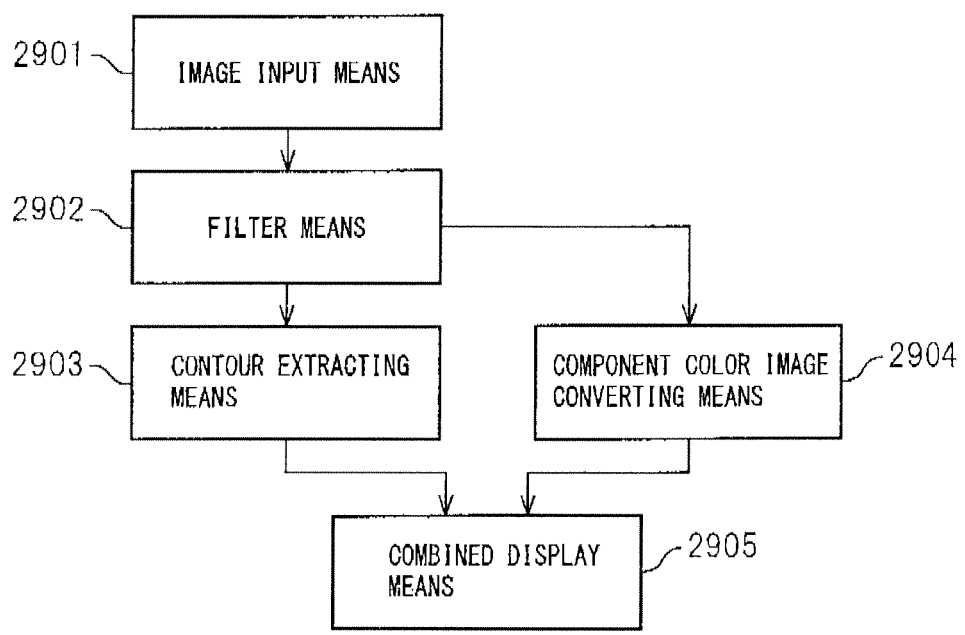
FIG. 29 is a block diagram for explaining an embodiment of the present invention.

Next, the embodiment which is shown in FIG. 29 will be explained. In the figure, reference numeral 2901 is an image inputting means. For example, it is a means for inputting a still image which was captured by an intraoral camera. The still image which was input by the image inputting means is output to a filtering means 2902. The filtering means 2902 is shown as an unsharp filter or other edge enhancement filter, but in addition sometimes a filter which enhances the contrast of the image may also be used.

The image which is filtered by the filtering means 2902 is output to the contour extracting means 2903 and the component color image converting means 2904. The contour extracting means 2903 is a comprised of a 2D Fourier transform means, a phase signal detecting means, and an inverse Fourier transform means, but these means are for example realized by combining program modules in a software library such as the "open-CV" (made by Intel).

Reference numeral 2904 is a component color image converting means. In the same way as explained above, it is comprised of a means for forming an image which is converted to the a* component color or b* component color or the H component color, S component color, or V component color of the La*b* color system or the HSV color system and a component color combining means for combining these component colors. The colors change, but an image with clear shapes of the teeth and the gums is formed. Furthermore, the changes in the color sometimes allow staining of teeth and tooth cavities to be found.

The contour image which is obtained by the contour extracting means 2903 and the images converted to component color images by the component color image converting means 2904 are output to the combined display means 2905. The combined display means 2905 combines the contour image which was output from the contour extracting means 2903 and the component color images which were output from the component color image converting means. This combination, for example, makes parts of the image other than the contours the same color system, makes the system of color transparent, and combines this with the component color image forming the background image. The combined image is displayed, on a computer monitor.

Sometimes this series of processing for composition can give an image with a clear boundary between the gums and teeth. Alternatively, the present embodiment is suitably used when detecting the boundary KL of two teeth at for example the center as a general measure for when combining images (for example, image 906e and image 1102f) where the mark ML becomes the center of the image in the left and right rows of teeth shown in FIG. 12. Alternatively, a contour image which is obtained by detecting the phase signal by a Fourier transform and the actual image can be combined as they are. Further, even if using only component color images, images of clear shapes can be obtained, so even with only the images obtained by the component color image detecting means, an image with a clear boundary of the gums and teeth is obtained. Such an image with a clear boundary between the teeth and the gums can be utilized as mark for various types of combining operations or may be used for explanations to the patient and for dental treatment.

INDUSTRIAL APPLICABILITY

The present invention provides a dental system which promote intraoral health in dental diagnosis and treatment by providing a patient with intraoral information in a readily understandable format and thereby enabling patient intraoral information to be refreshed. It is effectively utilized in the field of dental medicine.

REFERENCE NOTATIONS LIST 11 intraoral image inputting means
12 diagnosis and treatment portion detecting means
13 unit image forming means
14 diagnosis and treatment order setting means
15 diagnosis explanation forming means
16 display and output means
17 recording means

The invention claimed is:

1. A system for capturing and displaying an image of an entire oral cavity, the system comprising:
   (i) a handheld intraoral camera comprising
      a reflecting mirror arranged at a predetermined angle at a front end of the intraoral camera,
      a camera for continuously capturing rows of teeth in an oral cavity, and
      illumination devices arranged around the camera, an output of the illumination devices being reflected by the reflecting mirror and used to illuminate an observed portion of the oral cavity;
   (ii) a storing medium having installed therein a graphic software configured to combine a left panoramic tooth row image and a right panoramic tooth row image to form a full panoramic tooth row image;
   (iii) a computer processor programmed to operate the graphic software of the storing medium to combine the left panoramic tooth row image and the right panoramic tooth row image to form the full panoramic tooth row image; and
   (iv) a monitor configured to display the full panoramic tooth row image combined at the computer processor; wherein
   the intraoral camera is introduced into the oral cavity between and is manually moved and operated, the intraoral camera being configured to capture digital still images from a back tooth position to a front tooth position of an exterior surface of a tooth row by using a continuous capture technique, wherein a left set of continuously captured digital still images is obtained in an area ranging from a left back tooth to a center of front teeth of a tooth row, and a right set of continuously captured digital still images is obtained in an area ranging from a right back tooth to a center of the front teeth of the tooth row, and
   the computer processor is programmed to:
      (a) generate the left panoramic tooth row image by combining digital still images from the left set of continuously captured digital still images, wherein
         a first left digital still image including the center of the front teeth is combined with a second left digital still image taken adjacent to the first left digital still image and having an overlapping portion with the first left digital still image, to form a first left combined image,
         the first left combined image is combined with a third left digital still image taken adjacent to the second left digital still image and having an overlapping portion with the second left digital still image, to form a second left combined image, and
         a previous left combined image is repeatedly combined with an adjacent left digital still image until a last left combined image is combined with a last left digital still image positioned at the left back tooth adjacent to the last left combined image and having an overlapping portion with the last left combined image, thereby forming the left panoramic tooth row image,
      (b) generate the right panoramic tooth row image by combining digital still images from the right set of continuously captured digital still images, wherein
         a first right digital still image including the center of the front teeth is combined with a second right digital still image taken adjacent to the first right digital still image and having an overlapping portion with the first right digital still image, to form a first right combined image,
         the first right combined image is combined with a third right digital still image taken adjacent to the second right digital still image and having an overlapping portion with the second right digital still image, to form a second right combined image, and
         a previous right combined image is repeatedly combined with an adjacent right digital still image until a last right combined image is combined with a last right digital still image positioned at the right back tooth adjacent to the last right combined image and having an overlapping portion with the last right combined image, thereby forming the right panoramic tooth row image, and
      (c) generate the full panoramic tooth row image by detecting a digital still image of the center of the front teeth in each of the left panoramic tooth row image and the right panoramic tooth row image, superposing the two digital still images of the center of the front teeth to combine the left panoramic tooth row image and the right panoramic tooth row image, thereby forming the full panoramic tooth row image.

2. The system as set forth in claim 1, further comprising:
   a marking device configured to deposit or draw a mark that is recognizable on the digital still images at a predetermined position in a row of teeth, the mark configured to indicate a position of a digital still image.

3. The system as set forth in claim 1, wherein the monitor is further configured to display an X-ray image of teeth visible in the full panoramic tooth row image, the X-ray image being superposed or in parallel with the full panoramic tooth row image.

4. The system as set forth in claim 1, wherein the monitor is further configured to display a virtual image of a virtual tooth row obtained by virtually correcting, whitening, or coloring teeth visible in the full panoramic tooth row image.

5. The system as set forth in claim 1, further comprising:
   an image forming device configured to convert an image of the oral cavity to corresponding image data for each region of diagnosis and treatment in the oral cavity, and
   a setting device configured to set diagnosis and treatment order information for images of the image data obtained in the image forming device,
   wherein the images are displayed on the monitor in a list including the diagnosis and treatment order information.

6. The system as set forth in claim 1, further comprising:
   a portable data processing terminal having an input configured to input data relating to a dental practice, and
   a communicating device configured to communicate data with an external data processing terminal and a server that manages work attendance or dental diagnosis and treatment,
   wherein the monitor is configured to display the full panoramic tooth row image and the data relating to the dental practice.

7. The system as set forth in claim 1, further comprising:
   a dental treatment explanatory data providing device that includes a storage device for storing subdivided moving image data comprising moving images which have been prepared in advance, and
   a device for selecting the subdivided moving image data from the storage device and linking and connecting the moving image data at a computer device with the monitor so as to form the data for explaining dental treatment and display it on the monitor.

8. The system as set forth in claim 1, wherein the intraoral camera is a pencil type camera.

* * * * *